(12) United States Patent
Marlière

(10) Patent No.: US 9,017,977 B2
(45) Date of Patent: Apr. 28, 2015

(54) METHOD FOR THE ENZYMATIC PRODUCTION OF 3-HYDROXY-3-METHYLBUTYRIC ACID FROM ACETONE AND ACETYL-COA

(75) Inventor: Philippe Marlière, Mouscron (BE)

(73) Assignee: Scientist of Fortune S.A., Luxembourg (LU)

( * ) Notice: Subject to any disclaimer, the term of this patent is extended or adjusted under 35 U.S.C. 154(b) by 0 days.

(21) Appl. No.: 13/395,293

(22) PCT Filed: Sep. 14, 2010

(86) PCT No.: PCT/EP2010/063560
§ 371 (c)(1),
(2), (4) Date: May 16, 2012

(87) PCT Pub. No.: WO2011/032934
PCT Pub. Date: Mar. 24, 2011

(65) Prior Publication Data
US 2012/0220001 A1 Aug. 30, 2012

(30) Foreign Application Priority Data
Sep. 15, 2009 (EP) .................... 09170312

(51) Int. Cl.
*C12P 7/42* (2006.01)
*C12P 7/52* (2006.01)
*C12N 9/10* (2006.01)
*C12N 9/88* (2006.01)

(52) U.S. Cl.
CPC ................. *C12P 7/52* (2013.01); *C12N 9/1025* (2013.01); *C12N 9/88* (2013.01); *C12P 7/42* (2013.01); *C12Y 203/0301* (2013.01); *C12Y 401/03004* (2013.01)

(58) Field of Classification Search
CPC ........... C12P 7/42; C12P 7/52; C12N 9/1025; C12Y 203/0301
USPC ................... 435/141, 146, 193, 252.3, 252.7
See application file for complete search history.

(56) References Cited

U.S. PATENT DOCUMENTS

2008/0274523 A1* 11/2008 Renninger et al. ............ 435/157

OTHER PUBLICATIONS

Sang, H., Mechanisms of Development 121:1179-1186, 2004.*
Ezeji et al., World J. Microbiol. Biotechnol. 19:595-603, 2003.*
Bermejo et al., "Expression of *Clostridium acetobutylicum* ATCC 824 Genes in *Escherichia coli* for Acetone Production and Acetate Detoxification", Appl. Environmen. Microbiol. 64:1079-1085, 1998.*
The International Search Report and Written Opinion received in the parent international Application No. PCT/EP2010/063460, dated Dec. 6, 2010.
Crouch, et al., "A Mechanistic Rationalisation for the Substrate Specificity of Recombinant Mammalian 4-Hydroxyphenylpyruvate Dioxygenase (4-HPPD).", *Tetrahedron*, vol. 53, No. 20, 1997, pp. 6993-7010.
Lee, et al., "Conversion of β-Methylbutyric Acid to β-Hydroxy-β-Methylbutyric Acid by *Galactomyces reessi*", *Applied and Environmental Microbiology*, Nov. 1997, pp. 4191-4195.
Middleton, "The Kinetic Mechanism of 3-Hydroxy-3-methylglutaryl-Coenzyme A Synthase for Baker's Yeast", *Biochem J.*, vol. 126, 1972, pp. 35-47.

* cited by examiner

Primary Examiner — David J Steadman
(74) Attorney, Agent, or Firm — Foley & Lardner LLP

(57) ABSTRACT

Described is a method for the production of 3-hydroxy-3-methylbutyric acid by enzyme-catalyzed covalent bond formation between the carbon atom of the oxo group of acetone and the methyl group of a compound which provides an activated acetyl group. Also described are recombinant organisms which produce 3-hydroxy-3-methylbutyric acid, and related compositions and methods.

8 Claims, 7 Drawing Sheets

SEQUENCE LISTING

<160> NUMBER OF SEQ ID NOS: 25

<210> SEQ ID NO 1
<211> LENGTH: 462
<212> TYPE: PRT
<213> ORGANISM: Caenorhabditis elegans

<400> SEQUENCE: 1

Met Ser Leu Gly Gln Leu Ser Tyr Thr Pro Val Thr Asp Val Gly Ile
1               5                   10                  15

Gly Ala Ile Glu Leu Tyr Phe Pro Gln Asn Phe Val Asp Gln Asn Asp

```
                20                  25                  30
Leu Glu Lys Phe Asn Asn Val Ser Ser Gly Lys Tyr Thr Ile Gly Leu
            35                  40                  45
Gly Gln Gln Gln Met Gly Phe Cys Ser Asp Asn Glu Asp Ile Val Ser
        50                  55                  60
Ile Ser Leu Thr Val Thr Arg Lys Leu Ile Glu Thr Tyr Lys Ile Ser
65                  70                  75                  80
Thr Asp Ser Ile Gly Cys Leu Val Val Gly Thr Glu Thr Met Ile Asp
                85                  90                  95
Lys Ser Lys Ser Val Lys Thr Ala Leu Met Asp Leu Phe Pro Gly Asn
            100                 105                 110
Ser Asp Ile Glu Gly Val Asp Ile Lys Asn Ala Cys Phe Gly Gly Ala
        115                 120                 125
Gln Ala Leu Leu His Ala Ile Asp Trp Val Thr Val Asn His Pro Leu
    130                 135                 140
Asp Lys Lys Asn Ala Ile Val Val Ala Asp Ile Ala Ile Tyr Glu
145                 150                 155                 160
Glu Gly Pro Ala Arg Cys Thr Gly Gly Ala Gly Ala Ile Ala Phe Leu
                165                 170                 175
Ile Cys Pro Asp Ala Ser Ile Pro Ile Asp Arg Gln Phe Ser Ala Cys
            180                 185                 190
His Met Lys Asn Thr Trp Asp Phe Phe Lys Pro Ile Thr Pro Ile Pro
        195                 200                 205
Ser Glu Tyr Pro Val Val Asp Gly Ser Leu Ser Leu Ser Ser Tyr Leu
    210                 215                 220
Glu Ala Val Arg Met Thr Tyr Thr Tyr Phe Ile Ser Lys Val Asn Arg
225                 230                 235                 240
His Thr Thr Gly Ile Asp Gly Leu Asn Ser Phe Asp Gly Val Phe Leu
                245                 250                 255
His Ser Pro Phe Thr Lys Met Val Gln Lys Gly Leu Ala Val Met Asn
            260                 265                 270
Tyr Thr Asp Ser Gln Leu Arg His Lys Gln Leu Asn Gly Asn Gly Val
        275                 280                 285
Asp His Lys Leu Asp Glu Asn Asp Arg Ala Gly Leu Ala Lys Met Ile
    290                 295                 300
Glu Leu Ser Ala Gln Val Trp Lys Glu Lys Thr Asp Pro Tyr Leu Val
305                 310                 315                 320
Phe Asn Arg Arg Ile Gly Asn Met Tyr Thr Pro Ser Leu Phe Ala Gln
                325                 330                 335
Leu Leu Ala Tyr Leu Ala Ala Asp Asp Cys Val Thr Gly Glu Lys Ser
            340                 345                 350
Ile Leu Phe Phe Ala Tyr Gly Ser Gly Leu Ala Ser Ala Ile Phe Pro
        355                 360                 365
Gly Arg Val Arg Gln Thr Ser Asn Leu Asp Lys Ile Arg Gln Val Ala
    370                 375                 380
Ile Arg Ala Ile Lys Arg Leu Asp Asp Arg Ile Gln Phe Thr Pro Glu
385                 390                 395                 400
Glu Phe Thr Glu Thr Leu Gln Lys Arg Glu Val Phe Leu Arg Ser Lys
                405                 410                 415
Glu Ile Pro Lys Ser Pro Ser Glu Thr Ser Leu Phe Pro Asn Thr Tyr
            420                 425                 430
Phe Leu Asp Asn Met Asp Lys Leu Tyr Arg Arg Ser Tyr Thr Leu His
        435                 440                 445
```

```
Glu Glu Pro Asn Gly Val Gln Asn Gly Asn Gly Ile His His
    450                 455                 460

<210> SEQ ID NO 2
<211> LENGTH: 447
<212> TYPE: PRT
<213> ORGANISM: Schizosaccharomyces pombe

<400> SEQUENCE: 2

Met Ser Phe Asp Arg Lys Asp Ile Gly Ile Lys Gly Leu Val Leu Tyr
1               5                  10                  15

Thr Pro Asn Gln Tyr Val Glu Gln Ala Ala Leu Glu Ala His Asp Gly
            20                  25                  30

Val Ser Thr Gly Lys Tyr Thr Ile Gly Leu Gly Leu Thr Lys Met Ala
        35                  40                  45

Phe Val Asp Asp Arg Glu Asp Ile Tyr Ser Phe Gly Leu Thr Ala Leu
    50                  55                  60

Ser Gln Leu Ile Lys Arg Tyr Gln Ile Asp Ile Ser Lys Ile Gly Arg
65                  70                  75                  80

Leu Glu Val Gly Thr Glu Thr Ile Ile Asp Lys Ser Lys Ser Val Lys
                85                  90                  95

Ser Val Leu Met Gln Leu Phe Gly Asp Asn His Asn Val Glu Gly Ile
            100                 105                 110

Asp Cys Val Asn Ala Cys Tyr Gly Gly Val Asn Ala Leu Phe Asn Thr
        115                 120                 125

Ile Asp Trp Ile Glu Ser Ser Ala Trp Asp Gly Arg Asp Gly Ile Val
    130                 135                 140

Val Ala Gly Asp Ile Ala Leu Tyr Ala Lys Gly Asn Ala Arg Pro Thr
145                 150                 155                 160

Gly Gly Ala Gly Cys Val Ala Leu Leu Val Gly Pro Asn Ala Pro Ile
                165                 170                 175

Val Phe Glu Pro Gly Leu Arg Gly Thr Tyr Met Gln His Ala Tyr Asp
            180                 185                 190

Phe Tyr Lys Pro Asp Leu Thr Ser Glu Tyr Pro Tyr Val Asp Gly His
        195                 200                 205

Phe Ser Leu Glu Cys Tyr Val Lys Ala Leu Asp Gly Ala Tyr Ala Asn
    210                 215                 220

Tyr Asn Val Arg Asp Val Ala Lys Asn Gly Lys Ser Gln Gly Leu Gly
225                 230                 235                 240

Leu Asp Arg Phe Asp Tyr Cys Ile Phe His Ala Pro Thr Cys Lys Gln
                245                 250                 255

Val Gln Lys Ala Tyr Ala Arg Leu Leu Tyr Thr Asp Ser Ala Ala Glu
            260                 265                 270

Pro Ser Asn Pro Glu Leu Glu Gly Val Arg Glu Leu Leu Ser Thr Leu
        275                 280                 285

Asp Ala Lys Lys Ser Leu Thr Asp Lys Ala Leu Glu Lys Gly Leu Met
    290                 295                 300

Ala Ile Thr Lys Glu Arg Phe Asn Lys Arg Val Ser Pro Ser Val Tyr
305                 310                 315                 320

Ala Pro Thr Asn Cys Gly Asn Met Tyr Thr Ala Ser Ile Phe Ser Cys
                325                 330                 335

Leu Thr Ala Leu Leu Ser Arg Val Pro Ala Asp Glu Leu Lys Gly Lys
            340                 345                 350

Arg Val Gly Ala Tyr Ser Tyr Gly Ser Gly Leu Ala Ala Ser Phe Phe
```

```
                355                 360                 365
Ser Phe Val Val Lys Gly Asp Val Ser Glu Ile Ala Lys Lys Thr Asn
370                 375                 380

Leu Val Asn Asp Leu Asp Asn Arg His Cys Leu Thr Pro Thr Gln Tyr
385                 390                 395                 400

Glu Glu Ala Ile Glu Leu Arg His Gln Ala His Leu Lys Lys Asn Phe
                405                 410                 415

Thr Pro Lys Gly Ser Ile Glu Arg Leu Arg Ser Gly Thr Tyr Tyr Leu
            420                 425                 430

Thr Gly Ile Asp Asp Met Phe Arg Arg Ser Tyr Ser Val Lys Pro
        435                 440                 445

<210> SEQ ID NO 3
<211> LENGTH: 491
<212> TYPE: PRT
<213> ORGANISM: Saccharomyces cerevisiae

<400> SEQUENCE: 3

Met Lys Leu Ser Thr Lys Leu Cys Trp Cys Gly Ile Lys Gly Arg Leu
1               5                   10                  15

Arg Pro Gln Lys Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190

Tyr Asp Lys Gly Ala Ala Arg Pro Thr Gly Gly Ala Gly Thr Val Ala
        195                 200                 205

Met Trp Ile Gly Pro Asp Ala Pro Ile Val Phe Asp Ser Val Arg Ala
    210                 215                 220

Ser Tyr Met Glu His Ala Tyr Asp Phe Tyr Lys Pro Asp Phe Thr Ser
225                 230                 235                 240

Glu Tyr Pro Tyr Val Asp Gly His Phe Ser Leu Thr Cys Tyr Val Lys
                245                 250                 255

Ala Leu Asp Gln Val Tyr Lys Ser Tyr Ser Lys Lys Ala Ile Ser Lys
            260                 265                 270

Gly Leu Val Ser Asp Pro Ala Gly Ser Asp Ala Leu Asn Val Leu Lys
        275                 280                 285
```

```
Tyr Phe Asp Tyr Asn Val Phe His Val Pro Thr Cys Lys Leu Val Thr
    290                 295                 300
Lys Ser Tyr Gly Arg Leu Leu Tyr Asn Asp Phe Arg Ala Asn Pro Gln
305                 310                 315                 320
Leu Phe Pro Glu Val Asp Ala Glu Leu Ala Thr Arg Asp Tyr Asp Glu
                325                 330                 335
Ser Leu Thr Asp Lys Asn Ile Glu Lys Thr Phe Val Asn Val Ala Lys
            340                 345                 350
Pro Phe His Lys Glu Arg Val Ala Gln Ser Leu Ile Val Pro Thr Asn
        355                 360                 365
Thr Gly Asn Met Tyr Thr Ala Ser Val Tyr Ala Ala Phe Ala Ser Leu
    370                 375                 380
Leu Asn Tyr Val Gly Ser Asp Leu Gln Gly Lys Arg Val Gly Leu
385                 390                 395                 400
Phe Ser Tyr Gly Ser Gly Leu Ala Ala Ser Leu Tyr Ser Cys Lys Ile
                405                 410                 415
Val Gly Asp Val Gln His Ile Ile Lys Glu Leu Asp Ile Thr Asn Lys
            420                 425                 430
Leu Ala Lys Arg Ile Thr Glu Thr Pro Lys Asp Tyr Glu Ala Ala Ile
        435                 440                 445
Glu Leu Arg Glu Asn Ala His Leu Lys Lys Asn Phe Lys Pro Gln Gly
    450                 455                 460
Ser Ile Glu His Leu Gln Ser Gly Val Tyr Tyr Leu Thr Asn Ile Asp
465                 470                 475                 480
Asp Lys Phe Arg Arg Ser Tyr Asp Val Lys Lys
                485                 490

<210> SEQ ID NO 4
<211> LENGTH: 461
<212> TYPE: PRT
<213> ORGANISM: Arabidopsis thaliana

<400> SEQUENCE: 4

Met Ala Lys Asn Val Gly Ile Leu Ala Met Asp Ile Tyr Phe Pro Pro
1               5                   10                  15
Thr Cys Val Gln Gln Glu Ala Leu Glu Ala His Asp Gly Ala Ser Lys
            20                  25                  30
Gly Lys Tyr Thr Ile Gly Leu Gly Gln Asp Cys Leu Ala Phe Cys Thr
        35                  40                  45
Glu Leu Glu Asp Val Ile Ser Met Ser Phe Asn Ala Val Thr Ser Leu
    50                  55                  60
Phe Glu Lys Tyr Lys Ile Asp Pro Asn Gln Ile Gly Arg Leu Glu Val
65                  70                  75                  80
Gly Ser Glu Thr Val Ile Asp Lys Ser Lys Ser Ile Lys Thr Phe Leu
                85                  90                  95
Met Gln Leu Phe Glu Lys Cys Gly Asn Thr Asp Val Glu Gly Val Asp
            100                 105                 110
Ser Thr Asn Ala Cys Tyr Gly Gly Thr Ala Ala Leu Leu Asn Cys Val
        115                 120                 125
Asn Trp Val Glu Ser Asn Ser Trp Asp Gly Arg Tyr Gly Leu Val Ile
    130                 135                 140
Cys Thr Asp Ser Ala Val Tyr Ala Glu Gly Pro Ala Arg Pro Thr Gly
145                 150                 155                 160
Gly Ala Ala Ala Ile Ala Met Leu Ile Gly Pro Asp Ala Pro Ile Val
                165                 170                 175
```

Phe Glu Ser Lys Leu Arg Ala Ser His Met Ala His Val Tyr Asp Phe
            180                 185                 190

Tyr Lys Pro Asn Leu Ala Ser Glu Tyr Pro Val Val Asp Gly Lys Leu
        195                 200                 205

Ser Gln Thr Cys Tyr Leu Met Ala Leu Asp Ser Cys Tyr Lys His Leu
    210                 215                 220

Cys Asn Lys Phe Glu Lys Ile Glu Gly Lys Glu Phe Ser Ile Asn Asp
225                 230                 235                 240

Ala Asp Tyr Ile Val Phe His Ser Pro Tyr Asn Lys Leu Val Gln Lys
                245                 250                 255

Ser Phe Ala Arg Leu Leu Tyr Asn Asp Phe Leu Arg Asn Ala Ser Ser
            260                 265                 270

Ile Asp Glu Ala Ala Lys Glu Lys Phe Thr Pro Tyr Ser Ser Leu Thr
        275                 280                 285

Leu Asp Glu Ser Tyr Gln Ser Arg Asp Leu Glu Lys Val Ser Gln Gln
    290                 295                 300

Ile Ser Lys Pro Phe Tyr Asp Ala Lys Val Gln Pro Thr Thr Leu Ile
305                 310                 315                 320

Pro Lys Glu Val Gly Asn Met Tyr Thr Ala Ser Leu Tyr Ala Ala Phe
                325                 330                 335

Ala Ser Leu Ile His Asn Lys His Asn Asp Leu Ala Gly Lys Arg Val
            340                 345                 350

Val Met Phe Ser Tyr Gly Ser Gly Ser Thr Ala Thr Met Phe Ser Leu
        355                 360                 365

Arg Leu Asn Asp Asn Lys Pro Pro Phe Ser Ile Ser Asn Ile Ala Ser
    370                 375                 380

Val Met Asp Val Gly Gly Lys Leu Lys Ala Arg His Glu Tyr Ala Pro
385                 390                 395                 400

Glu Lys Phe Val Glu Thr Met Lys Leu Met Glu His Arg Tyr Gly Ala
                405                 410                 415

Lys Asp Phe Val Thr Thr Lys Glu Gly Ile Ile Asp Leu Leu Ala Pro
            420                 425                 430

Gly Thr Tyr Tyr Leu Lys Glu Val Asp Ser Leu Tyr Arg Arg Phe Tyr
        435                 440                 445

Gly Lys Lys Gly Glu Asp Gly Ser Val Ala Asn Gly His
    450                 455                 460

<210> SEQ ID NO 5
<211> LENGTH: 482
<212> TYPE: PRT
<213> ORGANISM: Dictyostelium discoideum

<400> SEQUENCE: 5

Met Thr Lys Pro Glu Asn Ile Gly Ile His Gly Ile Glu Val Tyr Phe
1               5                   10                  15

Pro Ser Thr Tyr Val Ala Gln Glu Asp Leu Glu Lys Phe Asp Gly Val
            20                  25                  30

Ser Gln Gly Lys Tyr Thr Leu Gly Leu Gly Gln Thr Asn Met Ala Phe
        35                  40                  45

Cys Gly Asp Arg Glu Asp Ile Tyr Ser Leu Ser Leu Asn Ala Val Asn
    50                  55                  60

Asn Leu Met Asp Lys Phe Asn Val Asp Pro Asn Ser Ile Gly Arg Leu
65                  70                  75                  80

Glu Val Gly Thr Glu Thr Val Ile Asp Lys Ser Lys Ser Val Lys Thr

```
                       85                  90                  95
Val Leu Met Asp Leu Phe Ala Lys His Gly Asn Thr Ser Ile Asp Gly
                100                 105                 110

Ile Asp Thr Ile Asn Ala Cys Tyr Gly Gly Thr Ser Ala Leu His Asn
            115                 120                 125

Ala Leu Gln Trp Met Glu Ser Ser Tyr Trp Asp Gly Arg Asn Ala Ile
        130                 135                 140

Val Val Ala Gly Asp Ile Ala Val Tyr Glu Lys Gly Pro Ala Arg Pro
145                 150                 155                 160

Thr Gly Gly Ala Gly Val Val Ala Met Leu Ile Gly Pro Asn Ala Pro
                165                 170                 175

Ile Thr Phe Glu Ser Gly Leu Arg Gly Val His Met Glu Asn Val Tyr
                180                 185                 190

Asp Phe Tyr Lys Pro Asp Met Asp Ser Glu Tyr Pro Arg Val Asp Gly
            195                 200                 205

Lys Leu Ser Ile Ser Cys Tyr Phe Arg Ala Ile Asp Asn Cys Tyr Asn
        210                 215                 220

Arg Tyr Ala Lys Ala Phe Glu Lys Lys Tyr Gly Lys Ser Phe Ser Leu
225                 230                 235                 240

Asp Gln Val Asp Phe Ala Leu Phe His Ser Pro Tyr Asn Lys Leu Val
                245                 250                 255

Gln Lys Ser Phe Gly Arg Met Leu Tyr Asn Asp Phe Leu Asn Asn Pro
                260                 265                 270

Asn Asp Ser Arg Tyr Ala Ser Leu Glu Ala Tyr Lys Asn Val Lys Pro
            275                 280                 285

Glu Asp Thr Tyr Phe Asp Ser Val Leu Glu Lys Ala Leu Ser Ala Ile
        290                 295                 300

Thr Lys Asn Asp Tyr Ala Thr Lys Val Ala Pro Thr Thr Leu Leu Ala
305                 310                 315                 320

Lys Gln Leu Gly Asn Thr Tyr Cys Gly Ser Thr Tyr Ser Gly Leu Leu
                325                 330                 335

Ser Leu Leu Asp Glu Lys Ser Asn Asp Leu Val Gly Lys Arg Val Leu
                340                 345                 350

Thr Phe Ser Tyr Gly Ser Gly Leu Ala Ala Ser Ala Phe Ser Phe Lys
            355                 360                 365

Val Glu Lys Pro Ile Asn His Ile Val Glu Lys Val Asp Leu Lys Asn
        370                 375                 380

Arg Leu Ala Lys Arg Val Arg Val Glu Pro Glu Ile Phe Thr Glu Lys
385                 390                 395                 400

Leu Ser Leu Arg Glu Thr Arg His Asn Leu Lys Asn Tyr Val Pro Ser
                405                 410                 415

Asp Glu Thr Thr Asn Met Phe Pro Gly Ser Phe Tyr Leu Ser Ser Val
                420                 425                 430

Asp Asn Ala Gly Ile Arg Lys Tyr Asp Arg Thr Tyr Ser Thr Ser Ala
            435                 440                 445

Val Leu Gly Ala Phe Gln Arg Gln Gln Ile Ser Gln Ser Thr Ile
        450                 455                 460

Lys Ser Leu Asn Leu Phe Arg Ala Thr Lys Ser Val Leu Ser Ile Leu
465                 470                 475                 480

Lys Lys

<210> SEQ ID NO 6
<211> LENGTH: 453
```

<212> TYPE: PRT
<213> ORGANISM: Blattella germanica

<400> SEQUENCE: 6

```
Met Trp Pro Ser Asp Val Gly Ile Val Ala Leu Glu Leu Ile Phe Pro
1               5                   10                  15

Ser Gln Tyr Val Asp Gln Val Asp Leu Glu Val Tyr Asp Asn Val Ser
            20                  25                  30

Ala Gly Lys Tyr Thr Val Gly Leu Gly Gln Ala Arg Met Gly Phe Cys
        35                  40                  45

Thr Asp Arg Glu Asp Ile Asn Ser Leu Cys Leu Thr Val Val Ser Arg
    50                  55                  60

Leu Met Glu Arg Trp Ser Ile Pro Tyr Ser Gln Ile Gly Arg Leu Glu
65                  70                  75                  80

Val Gly Thr Glu Thr Leu Leu Asp Lys Ser Lys Ser Val Lys Thr Val
                85                  90                  95

Leu Met Gln Leu Phe Lys Asp Asn Thr Asp Ile Glu Gly Val Asp Thr
            100                 105                 110

Val Asn Ala Cys Tyr Gly Gly Thr Ser Ala Leu Phe Asn Ala Ile Ser
        115                 120                 125

Trp Val Glu Ser Ser Ser Trp Asp Gly Arg Tyr Ala Leu Val Val Ala
    130                 135                 140

Gly Asp Ile Ala Val Tyr Ala Lys Gly Ser Ala Arg Pro Thr Gly Gly
145                 150                 155                 160

Ala Gly Ala Val Ala Met Leu Val Gly Ala Asn Ala Pro Leu Val Phe
                165                 170                 175

Asp Arg Gly Val Arg Ser Ser His Met Gln His Ala Tyr Asp Phe Tyr
            180                 185                 190

Lys Pro Asp Leu Ser Ser Leu Tyr Pro Thr Val Asp Gly Lys Leu Ser
        195                 200                 205

Ile Gln Cys Tyr Leu Ser Ala Leu Asp His Cys Tyr Gln Leu Tyr Cys
    210                 215                 220

Ser Lys Ile Gln Lys Gln Leu Gly Glu Lys Phe Asp Ile Glu Arg Leu
225                 230                 235                 240

Asp Ala Val Leu Phe His Ala Pro Tyr Cys Lys Leu Val Gln Lys Ser
                245                 250                 255

Leu Ala Arg Leu Val Leu Asn Asp Phe Val Arg Ala Ser Glu Glu Glu
            260                 265                 270

Arg Thr Thr Lys Tyr Ser Ser Leu Glu Ala Leu Lys Gly Val Lys Leu
        275                 280                 285

Glu Asp Thr Tyr Phe Asp Arg Glu Val Glu Lys Ala Val Met Thr Tyr
    290                 295                 300

Ser Lys Asn Met Phe Glu Glu Lys Thr Lys Pro Ser Leu Leu Leu Ala
305                 310                 315                 320

Asn Gln Val Gly Asn Met Tyr Thr Pro Ser Leu Tyr Gly Gly Leu Val
                325                 330                 335

Ser Leu Leu Val Ser Lys Ser Ala Gln Glu Leu Ala Gly Lys Arg Val
            340                 345                 350

Ala Leu Phe Ser Tyr Gly Ser Gly Leu Ala Ser Ser Met Phe Ser Leu
        355                 360                 365

Arg Ile Ser Ser Asp Ala Ser Ala Lys Ser Ser Leu Gln Arg Leu Val
    370                 375                 380

Ser Asn Leu Ser His Ile Lys Pro Gln Leu Asp Leu Arg His Lys Val
385                 390                 395                 400
```

```
Ser Pro Glu Glu Phe Ala Gln Thr Met Glu Thr Arg Glu His Asn His
                405                 410                 415

His Lys Ala Pro Tyr Thr Pro Glu Gly Ser Ile Asp Val Leu Phe Pro
            420                 425                 430

Gly Thr Trp Tyr Leu Glu Ser Val Asp Ser Leu Tyr Arg Arg Ser Tyr
        435                 440                 445

Lys Gln Val Pro Gly
        450

<210> SEQ ID NO 7
<211> LENGTH: 522
<212> TYPE: PRT
<213> ORGANISM: Gallus gallus

<400> SEQUENCE: 7

Met Pro Gly Ser Leu Pro Val Asn Thr Glu Ser Cys Trp Pro Lys Asp
1               5                   10                  15

Val Gly Ile Val Ala Leu Glu Ile Tyr Phe Pro Ser Gln Tyr Val Asp
            20                  25                  30

Gln Thr Glu Leu Glu Lys Tyr Asp Gly Val Asp Ala Gly Lys Tyr Thr
        35                  40                  45

Ile Gly Leu Gly Gln Ser Lys Met Gly Phe Cys Ser Asp Arg Glu Asp
    50                  55                  60

Ile Asn Ser Leu Cys Leu Thr Val Val Gln Lys Leu Met Glu Arg Asn
65                  70                  75                  80

Ser Leu Ser Tyr Asp Cys Ile Gly Arg Leu Glu Val Gly Thr Glu Thr
                85                  90                  95

Ile Ile Asp Lys Ser Lys Ser Val Lys Thr Val Leu Met Gln Leu Phe
            100                 105                 110

Glu Glu Ser Gly Asn Thr Asp Val Glu Gly Ile Asp Thr Thr Asn Ala
        115                 120                 125

Cys Tyr Gly Gly Thr Ala Ala Leu Phe Asn Ala Ile Asn Trp Ile Glu
    130                 135                 140

Ser Ser Ser Trp Asp Gly Arg Tyr Ala Leu Val Val Ala Gly Asp Ile
145                 150                 155                 160

Ala Val Tyr Ala Thr Gly Asn Ala Arg Pro Thr Gly Gly Ala Gly Ala
                165                 170                 175

Val Ala Met Leu Val Gly Ser Asn Ala Pro Leu Ile Phe Glu Arg Gly
            180                 185                 190

Leu Arg Gly Thr His Met Gln His Ala Tyr Asp Phe Tyr Lys Pro Asp
        195                 200                 205

Met Val Ser Glu Tyr Pro Val Val Asp Gly Lys Leu Ser Ile Gln Cys
    210                 215                 220

Tyr Leu Ser Ala Leu Asp Arg Cys Tyr Ser Val Tyr Arg Asn Lys Ile
225                 230                 235                 240

His Ala Gln Trp Gln Lys Glu Gly Thr Asp Arg Gly Phe Thr Leu Asn
                245                 250                 255

Asp Phe Gly Phe Met Ile Phe His Ser Pro Tyr Cys Lys Leu Val Gln
            260                 265                 270

Lys Ser Val Ala Arg Leu Leu Leu Asn Asp Phe Leu Ser Asp Gln Asn
        275                 280                 285

Ala Glu Thr Ala Asn Gly Val Phe Ser Gly Leu Glu Ala Phe Arg Asp
    290                 295                 300

Val Lys Leu Glu Asp Thr Tyr Phe Asp Arg Asp Val Glu Lys Ala Phe
```

```
            305                 310                 315                 320
Met Lys Ala Ser Ala Glu Leu Phe Asn Gln Lys Thr Lys Ala Ser Leu
                325                 330                 335
Leu Val Ser Asn Gln Asn Gly Asn Met Tyr Thr Pro Ser Val Tyr Gly
                340                 345                 350
Cys Leu Ala Ser Leu Leu Ala Gln Tyr Ser Pro Glu His Leu Ala Gly
                355                 360                 365
Gln Arg Ile Ser Glu Phe Ser Tyr Gly Ser Gly Phe Ala Ala Thr Leu
            370                 375                 380
Tyr Ser Ile Arg Val Thr Gln Asp Ala Thr Pro Gly Ser Ala Leu Asp
385                 390                 395                 400
Lys Ile Thr Ala Ser Leu Ser Asp Leu Lys Ala Arg Leu Asp Ser Arg
                405                 410                 415
Lys Cys Ile Ala Pro Asp Val Phe Ala Glu Asn Met Lys Ile Arg Gln
                420                 425                 430
Glu Thr His His Leu Ala Asn Tyr Ile Pro Gln Cys Ser Val Glu Asp
                435                 440                 445
Leu Phe Glu Gly Thr Trp Tyr Leu Val Arg Val Asp Glu Lys His Arg
            450                 455                 460
Arg Thr Tyr Ala Arg Arg Pro Val Met Gly Asp Gly Pro Leu Glu Ala
465                 470                 475                 480
Gly Val Glu Val Val His Pro Gly Ile Val His Glu His Ile Pro Ser
                485                 490                 495
Pro Ala Lys Lys Val Pro Arg Ile Pro Ala Thr Thr Glu Ser Glu Gly
                500                 505                 510
Val Thr Val Ala Ile Ser Asn Gly Val His
            515                 520

<210> SEQ ID NO 8
<211> LENGTH: 520
<212> TYPE: PRT
<213> ORGANISM: Homo sapiens

<400> SEQUENCE: 8

Met Pro Gly Ser Leu Pro Leu Asn Ala Glu Ala Cys Trp Pro Lys Asp
1               5                   10                  15
Val Gly Ile Val Ala Leu Glu Ile Tyr Phe Pro Ser Gln Tyr Val Asp
                20                  25                  30
Gln Ala Glu Leu Glu Lys Tyr Asp Gly Val Asp Ala Gly Lys Tyr Thr
            35                  40                  45
Ile Gly Leu Gly Gln Ala Lys Met Gly Phe Cys Thr Asp Arg Glu Asp
        50                  55                  60
Ile Asn Ser Leu Cys Met Thr Val Val Gln Asn Leu Met Glu Arg Asn
65                  70                  75                  80
Asn Leu Ser Tyr Asp Cys Ile Gly Arg Leu Glu Val Gly Thr Glu Thr
                85                  90                  95
Ile Ile Asp Lys Ser Lys Ser Val Lys Thr Asn Leu Met Gln Leu Phe
                100                 105                 110
Glu Glu Ser Gly Asn Thr Asp Ile Glu Gly Ile Asp Thr Thr Asn Ala
            115                 120                 125
Cys Tyr Gly Gly Thr Ala Ala Val Phe Asn Ala Val Asn Trp Ile Glu
        130                 135                 140
Ser Ser Ser Trp Asp Gly Arg Tyr Ala Leu Val Val Ala Gly Asp Ile
145                 150                 155                 160
```

```
Ala Val Tyr Ala Thr Gly Asn Ala Arg Pro Thr Gly Gly Val Gly Ala
            165                 170                 175

Val Ala Leu Leu Ile Gly Pro Asn Ala Pro Leu Ile Phe Glu Arg Gly
        180                 185                 190

Leu Arg Gly Thr His Met Gln His Ala Tyr Asp Phe Tyr Lys Pro Asp
        195                 200                 205

Met Leu Ser Glu Tyr Pro Ile Val Asp Gly Lys Leu Ser Ile Gln Cys
    210                 215                 220

Tyr Leu Ser Ala Leu Asp Arg Cys Tyr Ser Tyr Cys Lys Lys Ile
225                 230                 235                 240

His Ala Gln Trp Gln Lys Glu Gly Asn Asp Lys Asp Phe Thr Leu Asn
                245                 250                 255

Asp Phe Gly Phe Met Ile Phe His Ser Pro Tyr Cys Lys Leu Val Gln
            260                 265                 270

Lys Ser Leu Ala Arg Met Leu Leu Asn Asp Phe Leu Asn Asp Gln Asn
        275                 280                 285

Arg Asp Lys Asn Ser Ile Tyr Ser Gly Leu Glu Ala Phe Gly Asp Val
    290                 295                 300

Lys Leu Glu Asp Thr Tyr Phe Asp Arg Asp Val Glu Lys Ala Phe Met
305                 310                 315                 320

Lys Ala Ser Ser Glu Leu Phe Ser Gln Lys Thr Lys Ala Ser Leu Leu
                325                 330                 335

Val Ser Asn Gln Asn Gly Asn Met Tyr Thr Ser Ser Val Tyr Gly Ser
            340                 345                 350

Leu Ala Ser Val Leu Ala Gln Tyr Ser Pro Gln Gln Leu Ala Gly Lys
        355                 360                 365

Arg Ile Gly Val Phe Ser Tyr Gly Ser Gly Leu Ala Ala Thr Leu Tyr
    370                 375                 380

Ser Leu Lys Val Thr Gln Asp Ala Thr Pro Gly Ser Ala Leu Asp Lys
385                 390                 395                 400

Ile Thr Ala Ser Leu Cys Asp Leu Lys Ser Arg Leu Asp Ser Arg Thr
                405                 410                 415

Gly Val Ala Pro Asp Val Phe Ala Glu Asn Met Lys Leu Arg Glu Asp
            420                 425                 430

Thr His His Leu Val Asn Tyr Ile Pro Gln Gly Ser Ile Asp Ser Leu
        435                 440                 445

Phe Glu Gly Thr Trp Tyr Leu Val Arg Val Asp Glu Lys His Arg Arg
    450                 455                 460

Thr Tyr Ala Arg Arg Pro Thr Pro Asn Asp Asp Thr Leu Asp Glu Gly
465                 470                 475                 480

Val Gly Leu Val His Ser Asn Ile Ala Thr Glu His Ile Pro Ser Pro
                485                 490                 495

Ala Lys Lys Val Pro Arg Leu Pro Ala Thr Ala Glu Pro Glu Ala
            500                 505                 510

Ala Val Ile Ser Asn Gly Val Trp
        515                 520

<210> SEQ ID NO 9
<211> LENGTH: 508
<212> TYPE: PRT
<213> ORGANISM: Homo sapiens

<400> SEQUENCE: 9

Met Gln Arg Leu Leu Thr Pro Val Lys Arg Ile Leu Gln Leu Thr Arg
1               5                   10                  15
```

```
Ala Val Gln Glu Thr Ser Leu Thr Pro Ala Arg Leu Leu Pro Val Ala
             20                  25                  30

His Gln Arg Phe Ser Thr Ala Ser Ala Val Pro Leu Ala Lys Thr Asp
         35                  40                  45

Thr Trp Pro Lys Asp Val Gly Ile Leu Ala Leu Glu Val Tyr Phe Pro
 50                  55                  60

Ala Gln Tyr Val Asp Gln Thr Asp Leu Glu Lys Tyr Asn Asn Val Glu
 65                  70                  75                  80

Ala Gly Lys Tyr Thr Val Gly Leu Gly Gln Thr Arg Met Gly Phe Cys
                 85                  90                  95

Ser Val Gln Glu Asp Ile Asn Ser Leu Cys Leu Thr Val Val Gln Arg
            100                 105                 110

Leu Met Glu Arg Ile Gln Leu Pro Trp Asp Ser Val Gly Arg Leu Glu
            115                 120                 125

Val Gly Thr Glu Thr Ile Ile Asp Lys Ser Lys Ala Val Lys Thr Val
130                 135                 140

Leu Met Glu Leu Phe Gln Asp Ser Gly Asn Thr Asp Ile Glu Gly Ile
145                 150                 155                 160

Asp Thr Thr Asn Ala Cys Tyr Gly Gly Thr Ala Ser Leu Phe Asn Ala
                165                 170                 175

Ala Asn Trp Met Glu Ser Ser Ser Trp Asp Gly Arg Tyr Ala Met Val
            180                 185                 190

Val Cys Gly Asp Ile Ala Val Tyr Pro Ser Gly Asn Ala Arg Pro Thr
            195                 200                 205

Gly Gly Ala Gly Ala Val Ala Met Leu Ile Gly Pro Lys Ala Pro Leu
210                 215                 220

Ala Leu Glu Arg Gly Leu Arg Gly Thr His Met Glu Asn Val Tyr Asp
225                 230                 235                 240

Phe Tyr Lys Pro Asn Leu Ala Ser Glu Tyr Pro Ile Val Asp Gly Lys
                245                 250                 255

Leu Ser Ile Gln Cys Tyr Leu Arg Ala Leu Asp Arg Cys Tyr Thr Ser
            260                 265                 270

Tyr Arg Lys Lys Ile Gln Asn Gln Trp Lys Gln Ala Gly Ser Asp Arg
            275                 280                 285

Pro Phe Thr Leu Asp Asp Leu Gln Tyr Met Ile Phe His Thr Pro Phe
290                 295                 300

Cys Lys Met Val Gln Lys Ser Leu Ala Arg Leu Met Phe Asn Asp Phe
305                 310                 315                 320

Leu Ser Ala Ser Ser Asp Thr Gln Thr Ser Leu Tyr Lys Gly Leu Glu
                325                 330                 335

Ala Phe Gly Gly Leu Lys Leu Glu Asp Thr Tyr Thr Asn Lys Asp Leu
            340                 345                 350

Asp Lys Ala Leu Leu Lys Ala Ser Gln Asp Met Phe Asp Lys Lys Thr
            355                 360                 365

Lys Ala Ser Leu Tyr Leu Ser Thr His Asn Gly Asn Met Tyr Thr Ser
370                 375                 380

Ser Leu Tyr Gly Cys Leu Ala Ser Leu Leu Ser His His Ser Ala Gln
385                 390                 395                 400

Glu Leu Ala Gly Ser Arg Ile Gly Ala Phe Ser Tyr Gly Ser Gly Leu
                405                 410                 415

Ala Ala Ser Phe Phe Ser Phe Arg Val Ser Gln Asp Ala Ala Pro Gly
            420                 425                 430
```

```
Ser Pro Leu Asp Lys Leu Val Ser Thr Ser Asp Leu Pro Lys Arg
            435                 440                 445

Leu Ala Ser Arg Lys Cys Val Ser Pro Glu Glu Phe Thr Glu Ile Met
    450                 455                 460

Asn Gln Arg Glu Gln Phe Tyr His Lys Val Asn Phe Ser Pro Pro Gly
465                 470                 475                 480

Asp Thr Asn Ser Leu Phe Pro Gly Thr Trp Tyr Leu Glu Arg Val Asp
                485                 490                 495

Glu Gln His Arg Arg Lys Tyr Ala Arg Arg Pro Val
            500                 505

<210> SEQ ID NO 10
<211> LENGTH: 468
<212> TYPE: PRT
<213> ORGANISM: Dictyostelium discoideum

<400> SEQUENCE: 10

Met Lys Lys Thr Lys Asp Ile Gly Ile Cys Ala Ile Asp Ile Tyr Phe
1               5                   10                  15

Pro Gln Thr Tyr Val Asn Gln Ser Glu Leu Lys Lys Tyr Asp Lys Val
                20                  25                  30

Ser Asn Gly Lys Tyr Thr Ile Gly Leu Gly Gln Thr Asn Met Ser Phe
            35                  40                  45

Val Gly Asp Arg Glu Asp Ile Val Ser Met Ala Met Thr Ser Val Lys
50                  55                  60

Met Met Met Ser Lys Tyr Ser Ile Asp Tyr Gln Ser Ile Gly Arg Leu
65                  70                  75                  80

Glu Val Gly Thr Glu Thr Ile Ile Asp Lys Ser Lys Ser Val Lys Ser
                85                  90                  95

Ser Ile Met Ser Leu Phe Gln Glu Tyr Gly Asn Thr Ser Leu Glu Gly
            100                 105                 110

Val Asp Thr Leu Asn Ala Cys Tyr Gly Gly Thr Asn Ala Leu Phe Asn
        115                 120                 125

Ser Leu Gln Trp Ile Glu Ser Ser Tyr Trp Asp Gly Arg Tyr Ala Leu
130                 135                 140

Val Val Thr Gly Asp Ile Ala Val Tyr Ser Lys Gly Ala Ala Arg Pro
145                 150                 155                 160

Thr Gly Gly Ala Gly Val Val Thr Met Leu Ile Gly Pro Asn Ala Thr
                165                 170                 175

Leu Ile Phe Asp Gln Ser Leu Arg Gly Thr His Met Glu Asn Val Asn
            180                 185                 190

Asp Phe Tyr Lys Pro Asp Leu Ser Ser Glu Tyr Pro Tyr Val Asp Gly
        195                 200                 205

Lys Leu Ser Ile Glu Cys Tyr Leu Arg Ala Leu Asp Lys Cys Tyr Leu
210                 215                 220

Glu Tyr Lys Lys Phe Glu Ser Ile Asn Asp Asn Lys Phe Ser
225                 230                 235                 240

Met Asp Ser Phe Asp Tyr Val Cys Phe His Ser Pro Tyr Asn Arg Leu
                245                 250                 255

Val Gln Lys Ser Tyr Ala Arg Leu Ile Tyr Asn Asp Phe Leu Gln Asn
            260                 265                 270

Pro Asn Asn Pro Lys Tyr Gln Asp Leu Leu Pro Phe Lys Asp Leu Ser
        275                 280                 285

Thr Gly Lys Asp Ser Tyr Ile Asn Ser Lys Leu Asp Gln Ile Thr Leu
290                 295                 300
```

```
Lys Leu Ser Leu Asp Asp Phe Lys Thr Lys Val Asn Pro Ser Thr Leu
305                 310                 315                 320

Leu Ser Lys Glu Cys Gly Asn Ser Tyr Cys Gly Ser Val Tyr Ser Gly
            325                 330                 335

Ile Leu Ser Leu Ser Asn Val Asn Asp Leu Asn Asn Lys Lys Val
            340                 345                 350

Leu Val Phe Ser Tyr Gly Ser Gly Leu Ala Ala Ser Leu Phe Ser Phe
            355                 360                 365

Arg Ile Asn Asn Asn Lys Asn Arg Asn Asn Asn Asn Asn Asn Asn Asn
                370                 375                 380

Cys Phe Phe Lys Thr Thr Asn Asp Ile Gly Lys Ile Ser Asn Ile Lys
385                 390                 395                 400

Glu Arg Leu Ser Asn Arg Val Lys Val Ser Pro Glu Glu Phe Thr Arg
                405                 410                 415

Ile Leu Asp Ile Arg Glu Lys Ser His Gln Met Val Gly Ala Arg Thr
                420                 425                 430

Pro Ile Asp Thr Leu Asp Tyr Ile Ser Ala Gly Thr Phe Tyr Leu Glu
            435                 440                 445

Lys Ile Asp Glu Lys Leu Ile Arg His Tyr Lys Ser Lys Pro Ile Ile
450                 455                 460

Ser Ser Lys Leu
465

<210> SEQ ID NO 11
<211> LENGTH: 388
<212> TYPE: PRT
<213> ORGANISM: Staphylococcus epidermidis

<400> SEQUENCE: 11

Met Asn Ile Gly Ile Asp Lys Ile Ser Phe Tyr Val Pro Lys Tyr Tyr
1               5                   10                  15

Val Asp Met Ala Lys Leu Ala Glu Ala Arg Gln Val Asp Pro Asn Lys
                20                  25                  30

Phe Leu Ile Gly Ile Gly Gln Thr Glu Met Thr Val Ser Pro Val Asn
            35                  40                  45

Gln Asp Ile Val Ser Met Gly Ala Asn Ala Ala Lys Asp Ile Ile Thr
    50                  55                  60

Glu Glu Asp Lys Lys Asn Ile Gly Met Val Ile Val Ala Thr Glu Ser
65                  70                  75                  80

Ala Ile Asp Asn Ala Lys Ala Ala Ala Val Gln Ile His His Leu Leu
                85                  90                  95

Gly Ile Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Leu Ala Gln Arg
        115                 120                 125

Pro Asn Glu Lys Val Leu Val Ile Ala Ser Asp Thr Ala Arg Tyr Gly
    130                 135                 140

Ile His Ser Gly Gly Glu Pro Thr Gln Gly Ala Gly Ala Val Ala Met
145                 150                 155                 160

Met Ile Ser His Asp Pro Ser Ile Leu Lys Leu Asn Asp Asp Ala Val
                165                 170                 175

Ala Tyr Thr Glu Asp Val Tyr Asp Phe Trp Arg Pro Thr Gly His Gln
            180                 185                 190

Tyr Pro Leu Val Ala Gly Ala Leu Ser Lys Asp Ala Tyr Ile Lys Ser
```

```
                    195                 200                 205
Phe Gln Glu Ser Trp Asn Glu Tyr Ala Arg Arg His Asn Lys Thr Leu
210                 215                 220

Ala Asp Phe Ala Ser Leu Cys Phe His Val Pro Phe Thr Lys Met Gly
225                 230                 235                 240

Gln Lys Ala Leu Asp Ser Ile Ile Asn His Ala Asp Glu Thr Thr Gln
                245                 250                 255

Asp Arg Leu Asn Ser Ser Tyr Gln Asp Ala Val Asp Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Thr Arg Asp Leu Lys Gly Gly Gln Thr Ile Gly Leu Phe Ser
290                 295                 300

Tyr Gly Ser Gly Ser Val Gly Glu Phe Phe Ser Gly Thr Leu Val Asp
305                 310                 315                 320

Gly Phe Lys Glu Gln Leu Asp Val Glu Arg His Lys Ser Leu Leu Asn
                325                 330                 335

Asn Arg Ile Glu Val Ser Val Asp Glu Tyr Glu His Phe Phe Lys Arg
            340                 345                 350

Phe Asp Gln Leu Glu Leu Asn His Glu Leu Glu Lys Ser Asn Ala Asp
        355                 360                 365

Arg Asp Ile Phe Tyr Leu Lys Ser Ile Asp Asn Asn Ile Arg Glu Tyr
370                 375                 380

His Ile Ala Glu
385

<210> SEQ ID NO 12
<211> LENGTH: 389
<212> TYPE: PRT
<213> ORGANISM: Lactobacillus fermentum

<400> SEQUENCE: 12

Met Lys Ile Gly Ile Asp Lys Leu Ala Phe Ala Thr Thr Pro Tyr Tyr
1               5                   10                  15

Leu Ala Met Glu Asp Leu Ala Gln Gly Arg Asn Val Asp Pro Asn Lys
                20                  25                  30

Tyr Leu Ile Gly Ile Gly Gln Ser Lys Gln Ala Val Val Pro Pro Thr
            35                  40                  45

Gln Asp Val Val Thr Leu Ala Ala Ala Ala Asp Lys Leu Leu Asp
        50                  55                  60

Pro Val Glu Arg Asp Gln Val Ser Thr Val Ile Val Ala Thr Glu Ser
65                  70                  75                  80

Gly Ile Asp Asn Ser Lys Ala Ala Ala Val Tyr Val Lys His Leu Leu
                85                  90                  95

Lys Leu Ser Asp Phe Thr Arg Ala Val Glu Val Lys Glu Ala Cys Tyr
            100                 105                 110

Ser Ala Thr Ala Ala Leu Gln Phe Ala Arg Gly Leu Val Ala Leu Asn
        115                 120                 125

Pro Gln Glu Lys Ile Leu Val Ile Ala Ser Asp Ile Ala Arg Tyr Gly
130                 135                 140

Leu Glu Thr Gly Gly Glu Val Thr Gln Gly Ala Gly Ala Val Ala Met
145                 150                 155                 160

Leu Ile Thr Ala Asn Pro Arg Val Leu Ala Ile Glu Pro Thr Ser Val
                165                 170                 175
```

```
Ala Tyr Thr Lys Asp Val Met Asp Phe Trp Arg Pro Leu Tyr Ala Glu
                180                 185                 190

Glu Ala Leu Val Asn Gly Lys Tyr Ser Thr Asn Val Tyr Ile Asp Phe
            195                 200                 205

Phe Lys Gln Cys Trp Thr Arg Tyr Gln Gln Leu Ala Gly Tyr Gly Leu
        210                 215                 220

Glu Asp Phe Ala Ala Leu Ala Phe His Leu Pro Phe Thr Lys Met Gly
225                 230                 235                 240

Lys Lys Ala Leu Glu Ala Glu Leu Gly Asp Arg Asp Gln Val Ala
                245                 250                 255

Thr Arg Leu Arg Ala Asn Leu Thr Ala Gly Gln Glu Ala Cys Arg Gln
                260                 265                 270

Val Gly Asn Leu Tyr Thr Gly Ser Leu Tyr Leu Gly Leu Met Ser Leu
            275                 280                 285

Leu Thr Glu Gly Asp Val Lys Pro Gly Glu Arg Ile Gly Leu Phe Ser
        290                 295                 300

Tyr Gly Ser Gly Ala Glu Gly Phe Phe Ala Gly Ile Leu Gln Pro
305                 310                 315                 320

Gly Tyr Gln Glu Gly Leu Gly Asp Leu Asn Glu Gln Leu Ala Ala Arg
                325                 330                 335

Thr Gln Val Ser Leu Ala Glu Tyr Glu Asp Leu Phe Asn Gln Gln Leu
            340                 345                 350

Gly Leu Lys Glu Glu Asp Val Thr Phe Lys Thr Pro Ala Ala Gly Gln
        355                 360                 365

Arg Phe Val Leu Val Gly Gln Lys Asp His Arg Gln Tyr Arg Asp
370                 375                 380

Leu Ala Glu Arg Asp
385

<210> SEQ ID NO 13
<211> LENGTH: 351
<212> TYPE: PRT
<213> ORGANISM: Hyperthermus butylicus

<400> SEQUENCE: 13

Met Pro Arg Gly Ser Gly Ile Val Gly Trp Gly Gly Tyr Val Pro Arg
1               5                   10                  15

Tyr Arg Ile Lys Ala Ala Glu Ile Val Arg Val Trp Gly Trp Glu Pro
                20                  25                  30

Ser Val Pro Ala Gly Leu Gly Val Lys Glu Lys Ala Val Glu Asn Val
            35                  40                  45

Asp Glu Asp Ser Val Thr Met Gly Tyr Glu Ala Ala Arg Asn Ala Ile
50                  55                  60

Ala Arg Ala Asn Val Asp Pro Arg Glu Ile Lys Ala Val Phe Phe Gly
65                  70                  75                  80

Thr Glu Ser Lys Pro Tyr Ala Val Lys Pro Ser Ala Thr Ile Ile Ala
                85                  90                  95

Glu Ala Leu Gly Ile Thr Pro Glu Thr Met Ala Ser Asp Leu Glu Phe
            100                 105                 110

Ala Cys Arg Ala Ala Ser Glu Gly Leu Arg Ala Ser Leu Ala Leu Val
        115                 120                 125

Glu Ala Gly Tyr Met Lys Tyr Ala Leu Val Val Ala Ser Asp Thr Ala
130                 135                 140

Gln Ala Asn Pro Gly Asp Val Leu Glu Phe Thr Ala Ala Ser Gly Ala
145                 150                 155                 160
```

```
Ala Ala Phe Val Val Gly Pro Ala Ser Glu Ser Val Ala Val Leu Glu
                165                 170                 175

Gly Val Tyr Thr Tyr Val Thr Asp Thr Pro Asp Phe Trp Arg Gly Gln
            180                 185                 190

His Ser Arg Tyr Pro Met His Gly Glu Ala Phe Thr Gly Glu Pro Ala
        195                 200                 205

Tyr Phe His His Ile Glu Ser Ala Val Lys Gly Leu Met Glu Lys Leu
    210                 215                 220

Gly Leu Lys Pro Glu Asp Phe Asp Tyr Ala Val Phe His Gln Pro Asn
225                 230                 235                 240

Gly Lys Phe Pro Leu Arg Val Gly Ala Arg Leu Gly Phe Pro Lys Glu
                245                 250                 255

Lys Ile Leu Pro Gly Leu Leu Thr Pro Ile Ile Gly Asn Thr Tyr Asn
            260                 265                 270

Ala Ser Ala Leu Leu Gly Phe Ala Arg Ile Leu Asp Gln Ala Lys Pro
        275                 280                 285

Gly Gln Arg Ile Leu Val Ala Pro Phe Gly Ser Gly Ala Gly Ser Asp
    290                 295                 300

Ala Tyr Ser Phe Ile Val Thr Asp Arg Ile Glu Glu Ala Arg Asn Arg
305                 310                 315                 320

Ala Pro Lys Val Asp Asp Tyr Val Asn Trp Lys Arg Tyr Ile Asp Tyr
                325                 330                 335

Ala Met His Ala Arg Met Arg Lys Leu Tyr Asp Arg Arg Pro Val
            340                 345                 350

<210> SEQ ID NO 14
<211> LENGTH: 349
<212> TYPE: PRT
<213> ORGANISM: Chloroflexus aggregans

<400> SEQUENCE: 14

Met Met Lys Pro Asn Gln Pro Val Gly Ile Ile Gly Tyr Gly Val Tyr
1               5                   10                  15

Ile Pro Arg Tyr Arg Ile Ala Ala Arg Glu Ile Ala Arg Ile Trp Thr
                20                  25                  30

Asp Gly Gln Asn Gly Val Pro Val Glu Ala Lys Ser Val Pro Gly Pro
            35                  40                  45

Asp Glu Asp Thr Ile Thr Met Ala Ile Glu Ala Ala Arg Asn Ala Leu
        50                  55                  60

Val Arg Ala Asp Ile Pro Ala Ser Ala Leu Gly Ala Val Trp Ile Gly
65                  70                  75                  80

Ser Glu Ser His Pro Tyr Ser Val Lys Pro Ser Gly Thr Val Val Ala
                85                  90                  95

Asp Ala Leu Gly Ala Gly Pro Trp Val Ser Ala Ala Asp Trp Glu Phe
            100                 105                 110

Ala Cys Lys Ala Gly Ser Glu Ala Leu Thr Ala Ala Met Ala Leu Val
        115                 120                 125

Gly Ser Gly Met Gln Arg Tyr Ala Leu Ala Ile Gly Ala Asp Thr Ala
    130                 135                 140

Gln Gly Arg Pro Gly Asp Ala Leu Glu Tyr Thr Ala Ser Ala Gly Ala
145                 150                 155                 160

Ala Ala Leu Ile Val Gly Pro Ala Thr Glu Ala Leu Ala Thr Ile Asp
                165                 170                 175

Ala Thr Val Ser Tyr Val Thr Asp Thr Pro Asp Phe Tyr Arg Arg Ala
```

```
                        180                 185                 190
Asp Arg Pro Tyr Pro Val His Gly Asn Arg Phe Thr Gly Glu Pro Ala
                    195                 200                 205

Tyr Phe His Gln Ile Gln Ser Ala Ala Ser Glu Leu Leu Arg Gln Leu
                210                 215                 220

Asn Arg Thr Ala Ala Asp Phe Thr Tyr Ala Val Phe His Gln Pro Asn
225                 230                 235                 240

Ala Lys Phe Pro Gln Thr Val Ala Lys Arg Leu Gly Phe Thr Asp Ala
                245                 250                 255

Gln Ile Ala Pro Gly Leu Leu Ser Pro Gln Ile Gly Asn Thr Tyr Ser
            260                 265                 270

Gly Ala Ala Leu Leu Gly Leu Cys Ala Ile Leu Asp Val Ala Lys Pro
        275                 280                 285

Gly Asp Thr Ile Phe Val Thr Ser Tyr Gly Ser Gly Ala Gly Ser Asp
    290                 295                 300

Ala Tyr Ala Leu Thr Val Thr Glu Ala Ile Val Glu Arg Arg Glu Arg
305                 310                 315                 320

Ala Pro Leu Thr Ala Ala Tyr Leu Ala Arg Lys Val Met Ile Asp Tyr
                325                 330                 335

Ala Met Tyr Ala Lys Trp Arg Gly Lys Leu Val Met Gly
                340                 345

<210> SEQ ID NO 15
<211> LENGTH: 420
<212> TYPE: PRT
<213> ORGANISM: Bacillus subtilis

<400> SEQUENCE: 15

Met Val Ser Ala Gly Ile Glu Ala Met Asn Val Phe Gly Gly Thr Ala
1               5                   10                  15

Tyr Leu Asp Val Met Glu Leu Ala Lys Tyr Arg His Leu Asp Thr Ala
                20                  25                  30

Arg Phe Glu Asn Leu Leu Met Lys Glu Lys Ala Val Ala Leu Pro Tyr
            35                  40                  45

Glu Asp Pro Val Thr Phe Gly Val Asn Ala Ala Lys Pro Ile Ile Asp
        50                  55                  60

Ala Leu Ser Glu Ala Glu Lys Asp Arg Ile Glu Leu Leu Ile Thr Cys
65                  70                  75                  80

Ser Glu Ser Gly Ile Asp Phe Gly Lys Ser Leu Ser Thr Tyr Ile His
                85                  90                  95

Glu Tyr Leu Gly Leu Asn Arg Asn Cys Arg Leu Phe Glu Val Lys Gln
            100                 105                 110

Ala Cys Tyr Ser Gly Thr Ala Gly Phe Gln Met Ala Val Asn Phe Ile
        115                 120                 125

Leu Ser Gln Thr Ser Pro Gly Ala Lys Ala Leu Val Ile Ala Ser Asp
    130                 135                 140

Ile Ser Arg Phe Leu Ile Ala Glu Gly Gly Asp Ala Leu Ser Glu Asp
145                 150                 155                 160

Trp Ser Tyr Ala Glu Pro Ser Ala Gly Ala Gly Ala Val Ala Val Leu
                165                 170                 175

Val Gly Glu Asn Pro Glu Val Phe Gln Ile Asp Pro Gly Ala Asn Gly
            180                 185                 190

Tyr Tyr Gly Tyr Glu Val Met Asp Thr Cys Arg Pro Ile Pro Asp Ser
        195                 200                 205
```

```
Glu Ala Gly Asp Ser Asp Leu Ser Leu Met Ser Tyr Leu Asp Cys Cys
    210                 215                 220

Glu Gln Thr Phe Leu Glu Tyr Gln Lys Arg Val Pro Gly Ala Asn Tyr
225                 230                 235                 240

Gln Asp Thr Phe Gln Tyr Leu Ala Tyr His Thr Pro Phe Gly Gly Met
                245                 250                 255

Val Lys Gly Ala His Arg Thr Met Met Arg Lys Val Ala Lys Val Lys
            260                 265                 270

Thr Ser Gly Ile Glu Thr Asp Phe Leu Thr Arg Val Lys Pro Gly Leu
        275                 280                 285

Asn Tyr Cys Gln Arg Val Gly Asn Ile Met Gly Ala Ala Leu Phe Leu
290                 295                 300

Ala Leu Ala Ser Thr Ile Asp Gln Gly Arg Phe Asp Thr Pro Lys Arg
305                 310                 315                 320

Ile Gly Cys Phe Ser Tyr Gly Ser Gly Cys Cys Ser Glu Phe Tyr Ser
                325                 330                 335

Gly Ile Thr Thr Pro Gln Gly Gln Glu Arg Gln Arg Thr Phe Gly Ile
            340                 345                 350

Glu Lys His Leu Asp Arg Arg Tyr Gln Leu Ser Met Glu Glu Tyr Glu
        355                 360                 365

Leu Leu Phe Lys Gly Ser Gly Met Val Arg Phe Gly Thr Arg Asn Val
370                 375                 380

Lys Leu Asp Phe Glu Met Ile Pro Gly Ile Met Gln Ser Thr Gln Glu
385                 390                 395                 400

Lys Pro Arg Leu Phe Leu Glu Glu Ile Ser Glu Phe His Arg Lys Tyr
                405                 410                 415

Arg Trp Ile Ser
            420

<210> SEQ ID NO 16
<211> LENGTH: 388
<212> TYPE: PRT
<213> ORGANISM: Mycobacterium marinum

<400> SEQUENCE: 16

Met Val Ser Ile Gly Ile His Asp Leu Ser Ile Ala Thr Ala His Tyr
1               5                   10                  15

Val Leu Asp His Ala Thr Leu Ala Glu His His Gly Val Asp Val Asn
            20                  25                  30

Lys Tyr Leu Ile Gly Leu Gly Gln Gln Met Ser Ile Val Ala Pro
        35                  40                  45

Asp Glu Asp Ile Val Thr Leu Ala Ala Ala Ala Asp Pro Ile Ile
50                  55                  60

Lys Arg His Gly Ser Gln Lys Ile Arg Thr Ile Val Ile Gly Thr Glu
65                  70                  75                  80

Thr Gly Val Asp Gln Ser Lys Ser Ala Gly Ile Trp Val Ser Ser Leu
            85                  90                  95

Leu Gly Leu Pro Ser Ser Ala Arg Val Leu Glu Val Lys Gln Ala Cys
        100                 105                 110

Tyr Gly Ala Thr Gly Ala Leu Gln Leu Ala Leu Ala Leu Val His Arg
            115                 120                 125

Asp Pro Thr Gln Gln Val Leu Val Ile Ala Ala Asp Val Ala Arg Tyr
        130                 135                 140

Asp Leu Asp Ser Pro Gly Glu Pro Thr Gln Gly Ala Ala Ala Ala Ala
145                 150                 155                 160
```

```
Met Leu Val Ser Ala Asp Pro Ala Leu Leu Arg Leu Glu Glu Pro Thr
                165                 170                 175

Gly Ile Tyr Thr Ala Asp Ile Met Asp Phe Trp Arg Pro Asn Tyr Arg
            180                 185                 190

Ser Thr Ala Leu Val Asp Gly Lys Ala Ser Val Thr Ala Tyr Met Glu
        195                 200                 205

Ala Ala Ser Gly Ala Trp Lys Asp Tyr Thr Glu Arg Gly Gly Arg Ala
    210                 215                 220

Phe Gly Glu Phe Ala Ala Phe Cys Tyr His Gln Pro Phe Thr Lys Met
225                 230                 235                 240

Ala Tyr Lys Ala His Lys Gln Leu Ala Ala Glu Ala Gly Glu Asp Ala
                245                 250                 255

Ser Gly Ala Ala Val Gln Ala Val Gly Asn Thr Val Glu Tyr Asn
                260                 265                 270

Arg Arg Ile Gly Asn Ser Tyr Thr Ala Ser Leu Tyr Leu Ala Leu Ala
            275                 280                 285

Ala Leu Leu Asp Gln Ala Asp Asp Leu Ser Asp Gln Pro Ile Ala Met
    290                 295                 300

Leu Ser Tyr Gly Ser Gly Cys Val Ala Glu Leu Phe Ala Gly Thr Val
305                 310                 315                 320

Thr Pro Gly Tyr Gln Gln His Leu Arg Thr Asp Gln His Arg Ala Ala
                325                 330                 335

Leu Glu Thr Arg Ile Pro Leu Ser Tyr Glu His Tyr Arg Arg Leu His
            340                 345                 350

Asn Leu Thr Leu Pro Thr Asn Gly Asn His His Ser Leu Pro Val Glu
    355                 360                 365

Thr Ser Arg Pro Phe Arg Leu Thr Ala Ile Ser Glu His Lys Arg Met
370                 375                 380

Tyr Gly Ala Val
385

<210> SEQ ID NO 17
<211> LENGTH: 435
<212> TYPE: PRT
<213> ORGANISM: Zea mays

<400> SEQUENCE: 17

Met Leu Ala Ala Ser Thr Lys Val Gly Ser Arg Leu Ala Ser Pro His
1               5                   10                  15

Ala Ser Leu Ser Ala Gly Ala Ala Ala Leu Ala Ser Ser Pro
            20                  25                  30

Val Leu Gly Ser Gly Met Leu Pro Gly Ala Gly Phe Gly Glu Thr Gly
            35                  40                  45

Asn His His Ala Ala Asp Ala Pro Pro Leu Pro Cys Ser Ser Ser
    50                  55                  60

Gly Asp Ser Arg Glu Tyr Tyr Gln Trp Lys Arg Leu Val Asn Gln Arg
65                  70                  75                  80

Gln Ser Thr Leu His Val Gly Glu Val Pro Ala Ala Leu Gly His His
                85                  90                  95

Val Phe Gly Ala Gly Cys Ser Ser Arg Lys Gln His Ile Tyr Arg Tyr
                100                 105                 110

Phe Ser Ser Ser His Gln Gly Ser Ile Trp Ala Arg Ser Lys Ile
            115                 120                 125

Leu His Asp Leu Pro Gly Tyr Val Lys Ile Val Glu Val Gly Pro Arg
```

```
                130                 135                 140
Asp Gly Leu Gln Asn Glu Lys Asp Ile Val Pro Thr Pro Val Lys Val
145                 150                 155                 160

Glu Leu Ile Arg Arg Leu Ala Thr Ser Gly Leu Pro Val Val Glu Ala
                165                 170                 175

Thr Ser Phe Val Ser Pro Lys Trp Val Pro Gln Leu Ala Asp Ala Lys
                180                 185                 190

Asp Val Met Glu Ala Val Arg Thr Ile Gly Gly Val Arg Phe Pro Val
                195                 200                 205

Leu Thr Pro Asn Leu Lys Gly Phe Glu Ala Ala Ile Ala Ala Gly Ala
                210                 215                 220

Lys Glu Ile Ala Ile Phe Ala Ser Ala Ser Glu Gly Phe Ser Lys Ser
225                 230                 235                 240

Asn Ile Asn Cys Thr Ile Lys Glu Ser Ile Ala Arg Tyr Asn Asp Val
                245                 250                 255

Ala Leu Ala Ala Lys Glu Lys Glu Ile Pro Val Arg Gly Tyr Val Ser
                260                 265                 270

Cys Val Val Gly Cys Pro Val Asp Gly Pro Val Pro Pro Ser Asn Val
                275                 280                 285

Ala Tyr Val Ala Lys Glu Leu Tyr Asp Met Gly Cys Tyr Glu Val Ser
                290                 295                 300

Leu Gly Asp Thr Ile Gly Val Gly Thr Pro Gly Thr Val Val Pro Met
305                 310                 315                 320

Leu Glu Ala Ala Ile Ser Val Val Pro Val Glu Lys Leu Ala Val His
                325                 330                 335

Phe His Asp Thr Tyr Gly Gln Ser Leu Ser Asn Ile Leu Ile Ser Leu
                340                 345                 350

Gln Met Gly Val Ser Val Val Asp Ser Ser Val Ala Gly Leu Gly Gly
                355                 360                 365

Cys Pro Tyr Ala Lys Gly Ala Ser Gly Asn Val Ala Thr Glu Asp Val
                370                 375                 380

Val Tyr Met Leu Asn Gly Leu Gly Val Lys Thr Gly Val Asp Leu Gly
385                 390                 395                 400

Lys Val Met Ala Ala Gly Glu Phe Ile Cys Arg His Leu Gly Arg Gln
                405                 410                 415

Ser Gly Ser Lys Ala Ala Thr Ala Leu Ser Lys Val Thr Ala Asn Ala
                420                 425                 430

Ser Lys Leu
        435

<210> SEQ ID NO 18
<211> LENGTH: 335
<212> TYPE: PRT
<213> ORGANISM: Danio rerio (Brachydanio rerio)

<400> SEQUENCE: 18

Met Gly Asn Val Ser Ser Ala Val Lys His Cys Leu Ser Tyr Glu Thr
1               5                   10                  15

Phe Leu Arg Asp Tyr Pro Trp Leu Pro Arg Leu Leu Trp Glu Glu Lys
                20                  25                  30

Cys Ser Glu Leu Pro Lys Leu Pro Val Tyr Val Lys Ile Val Glu Val
                35                  40                  45

Gly Pro Arg Asp Gly Leu Gln Asn Glu Lys Glu Ile Val Pro Thr Glu
                50                  55                  60
```

-continued

Val Lys Ile Gln Leu Ile Asp Leu Leu Ser Gln Thr Gly Leu Pro Val
 65                  70                  75                  80

Ile Glu Ala Thr Ser Phe Val Ser Ser Lys Trp Val Ala Gln Met Ala
                 85                  90                  95

Asp His Thr Ala Val Leu Lys Gly Ile Lys Arg Ser Pro Asp Val Arg
            100                 105                 110

Tyr Pro Val Leu Thr Pro Asn Ile Gln Gly Phe Gln Ala Ala Val Ala
        115                 120                 125

Ala Gly Ala Asn Glu Val Ala Val Phe Gly Ser Ala Ser Glu Thr Phe
    130                 135                 140

Ser Arg Lys Asn Ile Asn Cys Ser Ile Glu Glu Ser Leu Gln Arg Phe
145                 150                 155                 160

Glu Gln Val Val Ser Ala Ala Lys Gln Glu Gly Ile Pro Val Arg Gly
                165                 170                 175

Tyr Val Ser Cys Ala Leu Gly Cys Pro Tyr Glu Gly Gln Val Lys Pro
            180                 185                 190

Ser Gln Val Thr Lys Val Ala Lys Arg Leu Phe Glu Leu Gly Cys Tyr
        195                 200                 205

Glu Val Ser Leu Gly Asp Thr Ile Gly Val Gly Thr Ala Gly Ser Met
    210                 215                 220

Ala Glu Met Leu Ser Asp Val Leu Thr Glu Val Pro Ala Gly Ala Leu
225                 230                 235                 240

Ala Val His Cys His Asp Thr Tyr Gly Gln Ala Leu Pro Asn Ile Leu
                245                 250                 255

Ile Ala Leu Gln Met Gly Val Ser Val Val Asp Ala Ser Val Ala Gly
            260                 265                 270

Leu Gly Gly Cys Pro Phe Ala Lys Gly Ala Ser Gly Asn Val Ser Thr
        275                 280                 285

Glu Asp Leu Leu Tyr Met Leu His Gly Leu Gly Ile Glu Thr Gly Val
    290                 295                 300

Asp Leu Leu Lys Val Met Glu Ala Gly Asp Phe Ile Cys Lys Ala Leu
305                 310                 315                 320

Asn Arg Lys Thr Asn Ser Lys Val Ser Gln Ala Thr Arg Asn Asn
                325                 330                 335

<210> SEQ ID NO 19
<211> LENGTH: 325
<212> TYPE: PRT
<213> ORGANISM: Bos taurus

<400> SEQUENCE: 19

Met Ala Thr Val Lys Lys Val Leu Pro Arg Arg Leu Val Gly Leu Ala
1               5                   10                  15

Thr Leu Arg Ala Val Ser Thr Ser Ser Val Gly Thr Phe Pro Lys Gln
            20                  25                  30

Val Lys Ile Val Glu Val Gly Pro Arg Asp Gly Leu Gln Asn Glu Lys
        35                  40                  45

Asn Ile Val Pro Thr Pro Val Lys Ile Lys Leu Ile Asp Met Leu Ser
    50                  55                  60

Glu Ala Gly Leu Pro Val Val Glu Ala Thr Ser Phe Val Ser Pro Lys
65                  70                  75                  80

Trp Val Pro Gln Met Ala Asp His Ala Glu Val Leu Lys Gly Ile Gln
                85                  90                  95

Lys Phe Pro Gly Val Asn Tyr Pro Val Leu Thr Pro Asn Phe Lys Gly
            100                 105                 110

```
Phe Gln Ala Ala Val Ala Ala Gly Ala Lys Glu Val Ala Ile Phe Gly
            115                 120                 125
Ala Ala Ser Glu Leu Phe Thr Lys Lys Asn Ile Asn Cys Ser Ile Asp
        130                 135                 140
Glu Ser Leu Gln Arg Phe Asp Glu Ile Leu Lys Ala Ala Arg Ala Ala
145                 150                 155                 160
Gly Ile Ser Val Arg Gly Tyr Val Ser Cys Val Leu Gly Cys Pro Tyr
                165                 170                 175
Glu Gly Lys Ile Ser Pro Ala Lys Val Ala Glu Val Thr Lys Lys Leu
            180                 185                 190
Tyr Ser Met Gly Cys Tyr Glu Ile Ser Leu Gly Asp Thr Ile Gly Val
        195                 200                 205
Gly Thr Pro Gly Ala Met Lys Asp Met Leu Ser Ala Val Leu Gln Glu
    210                 215                 220
Val Pro Val Thr Ala Leu Ala Val His Cys His Asp Thr Tyr Gly Gln
225                 230                 235                 240
Ala Leu Ala Asn Thr Leu Thr Ala Leu Gln Met Gly Val Ser Val Met
                245                 250                 255
Asp Ser Ser Val Ala Gly Leu Gly Gly Cys Pro Tyr Ala Gln Gly Ala
            260                 265                 270
Ser Gly Asn Leu Ala Thr Glu Asp Leu Val Tyr Met Leu Ala Gly Leu
        275                 280                 285
Gly Ile His Thr Gly Val Asn Leu Gln Lys Leu Leu Glu Ala Gly Ala
    290                 295                 300
Phe Ile Cys Gln Ala Leu Asn Arg Arg Thr Asn Ser Lys Val Ala Gln
305                 310                 315                 320
Ala Thr Cys Lys Leu
                325

<210> SEQ ID NO 20
<211> LENGTH: 325
<212> TYPE: PRT
<213> ORGANISM: Homo sapiens

<400> SEQUENCE: 20

Met Ala Ala Met Arg Lys Ala Leu Pro Arg Arg Leu Val Gly Leu Ala
1               5                   10                  15
Ser Leu Arg Ala Val Ser Thr Ser Ser Met Gly Thr Leu Pro Lys Arg
            20                  25                  30
Val Lys Ile Val Glu Val Gly Pro Arg Asp Gly Leu Gln Asn Glu Lys
        35                  40                  45
Asn Ile Val Ser Thr Pro Val Lys Ile Lys Leu Ile Asp Met Leu Ser
    50                  55                  60
Glu Ala Gly Leu Ser Val Ile Glu Thr Thr Ser Phe Val Ser Pro Lys
65                  70                  75                  80
Trp Val Pro Gln Met Gly Asp His Thr Glu Val Leu Lys Gly Ile Gln
                85                  90                  95
Lys Phe Pro Gly Ile Asn Tyr Pro Val Leu Thr Pro Asn Leu Lys Gly
            100                 105                 110
Phe Glu Ala Ala Val Ala Ala Gly Ala Lys Glu Val Val Ile Phe Gly
        115                 120                 125
Ala Ala Ser Glu Leu Phe Thr Lys Lys Asn Ile Asn Cys Ser Ile Glu
    130                 135                 140
Glu Ser Phe Gln Arg Phe Asp Ala Ile Leu Lys Ala Ala Gln Ser Ala
```

```
                145                 150                 155                 160
Asn Ile Ser Val Arg Gly Tyr Val Ser Cys Ala Leu Gly Cys Pro Tyr
                165                 170                 175

Glu Gly Lys Ile Ser Pro Ala Lys Val Ala Glu Val Thr Lys Lys Phe
            180                 185                 190

Tyr Ser Met Gly Cys Tyr Glu Ile Ser Leu Gly Asp Thr Ile Gly Val
        195                 200                 205

Gly Thr Pro Gly Ile Met Lys Asp Met Leu Ser Ala Val Met Gln Glu
    210                 215                 220

Val Pro Leu Ala Ala Leu Ala Val His Cys His Asp Thr Tyr Gly Gln
225                 230                 235                 240

Ala Leu Thr Asn Thr Leu Met Ala Leu Gln Met Gly Val Ser Val Val
                245                 250                 255

Asp Ser Ser Val Ala Gly Leu Gly Gly Cys Pro Tyr Ala Gln Gly Ala
                260                 265                 270

Ser Gly Asn Leu Ala Thr Glu Asp Leu Val Tyr Met Leu Glu Gly Leu
            275                 280                 285

Gly Ile His Thr Gly Val Asn Leu Gln Lys Leu Leu Glu Ala Gly Asn
        290                 295                 300

Phe Ile Cys Gln Ala Leu Asn Arg Lys Thr Ser Ser Lys Val Ala Gln
305                 310                 315                 320

Ala Thr Cys Lys Leu
                325

<210> SEQ ID NO 21
<211> LENGTH: 299
<212> TYPE: PRT
<213> ORGANISM: Pseudomonas putida Q88H25

<400> SEQUENCE: 21

Met Ser Leu Pro Lys His Val Arg Leu Val Glu Val Gly Pro Arg Asp
1               5                   10                  15

Gly Leu Gln Asn Glu Ala Gln Pro Ile Ser Val Ala Asp Lys Val Arg
            20                  25                  30

Leu Val Asn Asp Leu Thr Glu Ala Gly Leu Ala Tyr Ile Glu Val Gly
        35                  40                  45

Ser Phe Val Ser Pro Lys Trp Val Pro Gln Met Ala Gly Ser Ala Glu
    50                  55                  60

Val Phe Ala Gly Ile Gln Gln Arg Pro Gly Val Thr Tyr Ala Ala Leu
65                  70                  75                  80

Ala Pro Asn Leu Arg Gly Phe Glu Asp Ala Leu Ala Ala Gly Val Lys
                85                  90                  95

Glu Val Ala Val Phe Ala Ala Ser Glu Ala Phe Ser Gln Arg Asn
            100                 105                 110

Ile Asn Cys Ser Ile Ser Glu Ser Leu Lys Arg Phe Glu Pro Ile Met
        115                 120                 125

Asp Ala Ala Arg Ser His Gly Met Arg Val Arg Gly Tyr Val Ser Cys
    130                 135                 140

Val Leu Gly Cys Pro Tyr Glu Gly Lys Val Ser Ala Glu Gln Val Ala
145                 150                 155                 160

Pro Val Ala Arg Ala Leu His Asp Met Gly Cys Tyr Glu Val Ser Leu
                165                 170                 175

Gly Asp Thr Ile Gly Thr Gly Thr Ala Gly Asp Thr Arg Arg Leu Phe
            180                 185                 190
```

```
Glu Val Val Ser Ala Gln Val Pro Arg Glu Gln Leu Ala Gly His Phe
            195                 200                 205

His Asp Thr Tyr Gly Gln Ala Leu Ala Asn Val Tyr Ala Ser Leu Leu
    210                 215                 220

Glu Gly Ile Ser Val Phe Asp Ser Ser Val Ala Gly Leu Gly Gly Cys
225                 230                 235                 240

Pro Tyr Ala Lys Gly Ala Thr Gly Asn Ile Ala Ser Glu Asp Val Val
                245                 250                 255

Tyr Leu Leu Gln Gly Leu Gly Ile Glu Thr Gly Ile Asp Leu Gly Leu
                260                 265                 270

Leu Ile Ala Ala Gly Gln Arg Ile Ser Gly Val Leu Gly Arg Asp Asn
            275                 280                 285

Gly Ser Arg Val Ala Arg Ala Cys Ser Ala Gln
    290                 295

<210> SEQ ID NO 22
<211> LENGTH: 312
<212> TYPE: PRT
<213> ORGANISM: Acinetobacter baumannii B7H4C6

<400> SEQUENCE: 22

Met Thr Ala Phe Ser Asp Leu Leu Val Val Gln Glu Val Ser Pro Arg
1               5                   10                  15

Asp Gly Leu Gln Ile Glu Pro Thr Trp Val Pro Thr Asp Lys Lys Ile
            20                  25                  30

Asp Leu Ile Asn Gln Leu Ser Thr Met Gly Phe Ser Arg Ile Glu Ala
        35                  40                  45

Gly Ser Phe Val Ser Pro Lys Ala Ile Pro Asn Leu Arg Asp Gly Glu
    50                  55                  60

Glu Val Phe Thr Gly Ile Thr Arg His Lys Asp Ile Ile Tyr Val Gly
65                  70                  75                  80

Leu Ile Pro Asn Leu Lys Gly Ala Leu Arg Ala Val Glu Ala Asn Ala
                85                  90                  95

Asn Glu Leu Asn Leu Val Leu Ser Ala Ser Gln Thr His Asn Leu Ala
            100                 105                 110

Asn Met Arg Met Thr Lys Ala Gln Ser Phe Ala Gly Phe Thr Glu Ile
        115                 120                 125

Val Glu Gln Leu Gln Gly Lys Thr Gln Phe Asn Gly Thr Val Ala Thr
    130                 135                 140

Thr Phe Gly Cys Pro Phe Glu Gly Lys Ile Ser Glu Arg Glu Val Phe
145                 150                 155                 160

Ser Leu Val Glu His Tyr Leu Lys Leu Gly Ile His Asn Ile Thr Leu
                165                 170                 175

Ala Asp Thr Thr Gly Met Ala Asn Pro Val Gln Val Lys Arg Ile Val
            180                 185                 190

Ser His Val Leu Ser Leu Ile Ser Pro Glu Gln Leu Thr Leu His Phe
        195                 200                 205

His Asn Thr Arg Gly Leu Gly Leu Thr Asn Val Leu Ala Ala Tyr Glu
    210                 215                 220

Val Gly Ala Arg Arg Phe Asp Ala Ala Leu Gly Gly Leu Gly Gly Cys
225                 230                 235                 240

Pro Phe Ala Pro Gly Ala Ser Gly Asn Ile Cys Thr Glu Asp Leu Val
                245                 250                 255

Asn Met Cys Glu Glu Ile Gly Ile Pro Thr Thr Ile Asp Leu Asp Ala
            260                 265                 270
```

Leu Ile Gln Leu Ser Arg Thr Leu Pro Ala Leu Leu Gly His Asp Thr
            275                 280                 285

Pro Ser Gln Leu Ala Lys Ala Gly Arg Asn Thr Asp Leu His Pro Ile
        290                 295                 300

Pro Asp Tyr Ile Lys Ser Leu Asn
305                 310

<210> SEQ ID NO 23
<211> LENGTH: 286
<212> TYPE: PRT
<213> ORGANISM: Thermus thermophilus Q72IH0

<400> SEQUENCE: 23

Met Lys Ala Ser Val Arg Trp Val Glu Cys Pro Arg Asp Ala Trp Gln
1               5                   10                  15

Gly Phe Ser Arg Phe Ile Pro Thr Glu Glu Lys Val Ala Phe Leu Asn
            20                  25                  30

Glu Leu Leu Glu Ala Gly Phe Ala His Leu Asp Leu Thr Ser Phe Val
        35                  40                  45

Ser Pro Lys Trp Val Pro Gln Met Gln Asp Ala Glu Glu Val Leu Lys
    50                  55                  60

Ala Leu Pro Pro Asn Gly Arg Thr Tyr Leu Ala Ile Val Ala Asn
65                  70                  75                  80

Glu Lys Gly Leu Glu Arg Ala Leu Ala Ala Pro Asn Leu Thr His Val
                85                  90                  95

Gly Tyr Pro Phe Ser Leu Ser Glu Thr Phe Gln Gln Arg Asn Thr Asn
            100                 105                 110

Arg Ser Ile Glu Ala Ser Trp Pro Leu Val Gly Ala Met Val Glu Arg
        115                 120                 125

Thr Glu Gly Arg Leu Gly Leu Val Val Tyr Leu Ser Met Ala Phe Gly
    130                 135                 140

Asn Pro Tyr Gly Asp Pro Trp Ser Val Glu Ala Val Leu Glu Ala Leu
145                 150                 155                 160

Ala Arg Leu Lys Glu Met Gly Val Arg Glu Ile Ala Leu Ala Asp Thr
                165                 170                 175

Tyr Gly Val Ala Glu Pro Glu Arg Ile His Glu Val Leu Lys Ala Ala
            180                 185                 190

Val Ala Arg Phe Gly Pro Glu Gly Leu Gly Ala His Leu His Ala Arg
        195                 200                 205

Pro Glu Gly Ala Leu Ala Lys Val Glu Ala Val Leu Ala Ala Gly Val
    210                 215                 220

Thr Trp Leu Glu Gly Ala Leu Ala Gly Val Gly Gly Cys Pro Phe Ala
225                 230                 235                 240

Gly Asp Glu Leu Val Gly Asn Leu Pro Thr Glu Val Val Leu Pro His
                245                 250                 255

Leu Glu Lys Arg Gly Leu Ala Thr Gly Val Asp Leu Ser Arg Leu Pro
            260                 265                 270

Leu Leu Ala Glu Glu Ala Ala Arg Leu Lys Ala Leu Tyr Ala
        275                 280                 285

<210> SEQ ID NO 24
<211> LENGTH: 387
<212> TYPE: PRT
<213> ORGANISM: Lactobacillus delbrueckii

<400> SEQUENCE: 24

```
Met Asp Ile Gly Ile Asp Gln Ile Gly Phe Tyr Thr Pro Asn Lys Phe
1               5                   10                  15

Val Asp Met Val Asp Leu Ala Asn Ala Arg Asn Gln Asp Pro Asn Lys
            20                  25                  30

Phe Leu Ile Gly Ile Gly Gln Asp Arg Met Ala Val Ala Asp Lys Thr
        35                  40                  45

Gln Asp Ala Val Ser Met Gly Ile Asn Ala Thr Ala Glu Tyr Leu Asp
50                  55                  60

Gln Val Asp Leu Glu Gln Leu Gly Leu Leu Ile Phe Ala Thr Glu Ser
65                  70                  75                  80

Gly Ile Asp Gln Ser Lys Ser Ala Ser Leu Phe Val Lys Glu Ala Leu
                85                  90                  95

Asn Leu Pro Ala Arg Ile Arg Thr Phe Glu Ile Lys Glu Ala Cys Phe
                100                 105                 110

Ala Leu Thr Ala Ser Leu Gln Val Ala Arg Asp Tyr Val Arg Ala His
            115                 120                 125

Pro His His Ser Ala Met Ile Ile Gly Ser Asp Ile Ala Arg Tyr Gly
        130                 135                 140

Leu Ala Thr Ala Gly Glu Val Thr Gln Gly Ala Gly Ala Ile Ser Met
145                 150                 155                 160

Leu Ile Lys Glu Asn Pro Ala Ile Ile Ala Leu Glu Asp Gly His Thr
                165                 170                 175

Ser His Ser Glu Asn Ile Asn Asp Phe Trp Arg Pro Asn Asn Leu Ala
                180                 185                 190

Thr Ala Val Val Asp Gly His Tyr Ser Arg Asp Val Tyr Leu Asp Phe
            195                 200                 205

Phe Lys Ser Thr Phe Lys Pro Phe Leu Ala Glu Lys Gln Leu Gln Val
        210                 215                 220

Ser Asp Phe Ala Gly Ile Cys Tyr His Leu Pro Tyr Thr Lys Met Gly
225                 230                 235                 240

Tyr Lys Ala His Lys Ile Ala Ile Glu Gly Gln Asp Asp Glu Thr Val
                245                 250                 255

Lys Arg Leu Ser Asp Asn Phe Gln Leu Ser Ala Lys Tyr Ser Arg Gln
                260                 265                 270

Val Gly Asn Ile Tyr Thr Ala Ser Leu Tyr Met Ser Val Leu Ser Leu
            275                 280                 285

Leu Glu Asn Gly Asp Leu Glu Ala Gly Asp Arg Ile Gly Phe Phe Ser
        290                 295                 300

Tyr Gly Ser Gly Ala Met Ala Glu Phe Phe Ser Gly Lys Val Val Ala
305                 310                 315                 320

Gly Tyr Gln Lys Arg Leu Arg Pro Ala Leu His Ala Arg Met Leu Lys
                325                 330                 335

Glu Arg Ile Arg Leu Gly Val Gly Gln Tyr Glu Asp Ile Phe Thr Glu
            340                 345                 350

Gly Leu Glu Ala Leu Pro Glu Asn Val Glu Phe Thr Ser Asp Ala Asn
        355                 360                 365

His Gly Thr Trp Tyr Leu Ala Gly Gln Glu Gly Tyr Val Arg Gln Tyr
        370                 375                 380

Lys Gln Lys
385
```

<210> SEQ ID NO 25
<211> LENGTH: 388

```
<212> TYPE: PRT
<213> ORGANISM: Staphylococcus haemolyticus

<400> SEQUENCE: 25

Met Ser Ile Gly Ile Asp Lys Ile Asn Phe Tyr Val Pro Lys Tyr Tyr
1               5                   10                  15

Val Asp Met Ala Lys Leu Ala Glu Ala Arg Gln Val Asp Pro Asn Lys
            20                  25                  30

Phe Leu Ile Gly Ile Gly Gln Thr Gln Met Ala Val Ser Pro Val Ser
        35                  40                  45

Gln Asp Ile Val Ser Met Gly Ala Asn Ala Ala Lys Asp Ile Ile Thr
    50                  55                  60

Asp Asp Lys Lys His Ile Gly Met Val Ile Val Ala Thr Glu Ser
65                  70                  75                  80

Ala Ile Asp Asn Ala Lys Ala Ala Val Gln Ile His Asn Leu Leu
                85                  90                  95

Gly Val Gln Pro Phe Ala Arg Cys Phe Glu Met Lys Glu Ala Cys Tyr
            100                 105                 110

Ala Ala Thr Pro Ala Ile Gln Leu Ala Lys Asp Tyr Ile Glu Lys Arg
        115                 120                 125

Pro Asn Glu Lys Val Leu Val Ile Ala Ser Asp Thr Ala Arg Tyr Gly
    130                 135                 140

Ile Gln Ser Gly Gly Glu Pro Thr Gln Gly Ala Gly Ala Val Ala Met
145                 150                 155                 160

Leu Ile Ser Asn Asn Pro Ser Ile Leu Glu Leu Asn Asp Asp Ala Val
                165                 170                 175

Ala Tyr Thr Glu Asp Val Tyr Asp Phe Trp Arg Pro Thr Gly His Lys
            180                 185                 190

Tyr Pro Leu Val Ala Gly Ala Leu Ser Lys Asp Ala Tyr Ile Lys Ser
        195                 200                 205

Phe Gln Glu Ser Trp Asn Glu Tyr Ala Arg Arg Glu Asp Lys Thr Leu
    210                 215                 220

Ser Asp Phe Glu Ser Leu Cys Phe His Val Pro Phe Thr Lys Met Gly
225                 230                 235                 240

Lys Lys Ala Leu Asp Ser Ile Ile Asn Asp Ala Asp Glu Thr Thr Gln
                245                 250                 255

Glu Arg Leu Thr Ser Gly Tyr Glu Asp Ala Val Tyr Tyr Asn Arg Tyr
            260                 265                 270

Val Gly Asn Ile Tyr Thr Gly Ser Leu Tyr Leu Ser Leu Ile Ser Leu
        275                 280                 285

Leu Glu Asn Arg Ser Leu Lys Gly Gly Gln Thr Ile Gly Leu Phe Ser
    290                 295                 300

Tyr Gly Ser Gly Ser Val Gly Glu Phe Phe Ser Ala Thr Leu Val Glu
305                 310                 315                 320

Gly Tyr Glu Lys Gln Leu Asp Ile Glu Gly His Lys Ala Leu Leu Asn
                325                 330                 335

Glu Arg Gln Glu Val Ser Val Glu Asp Tyr Glu Ser Phe Phe Lys Arg
            340                 345                 350

Phe Asp Asp Leu Glu Phe Asp His Ala Thr Glu Gln Thr Asp Asp Asp
        355                 360                 365
```

```
Lys Ser Ile Tyr Tyr Leu Glu Asn Ile Gln Asp Asp Ile Arg Gln Tyr
    370                 375                 380

His Ile Pro Lys
385
```

METHOD FOR THE ENZYMATIC PRODUCTION OF 3-HYDROXY-3-METHYLBUTYRIC ACID FROM ACETONE AND ACETYL-COA

CROSS REFERENCE TO RELATED APPLICATIONS

This application is the U.S. National Phase of International Application PCT/EP2010/063460, which was published in English on Mar. 24, 2011, as WO 2011/032934, and claims the benefit of the filing date of European Patent Application No. 09170312.4, filed Sep. 15, 2009.

FIELD OF THE INVENTION

The present invention relates to a method for the production of 3-hydroxy-3-methylbutyric acid (also referred to as beta-hydroxyisovalerate or HIV) from acetone and a compound which provides an activated acetyl group comprising the enzymatic conversion of acetone and a compound which provides an activated acetyl group into 3-hydroxy-3-methylbutyric acid. The conversion makes use of an enzyme which is capable of catalyzing the formation of a covalent bond between the carbon atom of the oxo (i.e. the C=O) group of acetone and the methyl group of the compound which provides an activated acetyl group. Preferably, the enzyme employed in the process is an enzyme with the activity of a HMG CoA synthase (EC 2.3.3.10) and/or a PksG protein and/or an enzyme with the activity of a C—C bond cleavage/condensation lyase, such as HMG CoA lyase (EC 4.1.3.4). The present invention also relates to organisms able to produce 3-hydroxy-3-methylbutyric acid from acetone and a compound which provides an activated acetyl group and to the use of the above-mentioned enzymes and organisms for the production of 3-hydroxy-3-methylbutyric acid. Finally, the present invention relates to the use of acetone for the production of 3-hydroxy-3-methylbutyric acid.

BACKGROUND 3-hydroxy-3-methylbutyric acid (also referred to as beta-hydroxyisovalerate or HIV; see FIG. 1) is a metabolite of the essential amino acid leucine and is synthesized in the human body. It can be found in small quantities in grapefruit, alfalfa and catfish. It is also known to occur in some metabolic disorders of leucine catabolism, i.e. hypovaleric acidemia. It has been shown that 3-hydroxy-3-methylbutyric acid may have an effect on increasing muscle weight and strength (Nissen et al., J. Appl. Physiol. 81 (1996), 2095-2104). Wilson et al. (Nutrition & Metabolism 5 (2008)) proposes as the mechanisms of action the following:
- increased sarcolemmal integrity via conversion by HMG CoA reductase
- enhanced protein synthesis via the mTOR pathway
- depression of protein degradation through inhibition of the ubiquitin pathway.

3-hydroxy-3-methylbutyric acid is supposed to help muscles combat protein breakdown, assist in muscle repair and support increased endurance. It has been described to help patients with chronic obstructive pulmonary disease in hospital intensive care units, muscle wasting associated with HIV and cancer and trauma victims with severe injuries. Thus, it is of commercial interest because of its use as a muscle enhancer for bodybuilding and as a medicament for avoiding muscle wasting.

U.S. Pat. No. 7,026,507 describes a process for preparing solid formulations of sodium 3-hydroxy-3-methylbutyrate in which, in a first process step, 4,4-dimethyloxetan-2-one is reacted with aqueous sodium hydroxide to form a solution of sodium 3-hydroxy-3-methylbutyrate, and then, if appropriate after concentration, the solution is applied, in a further process step, to synthetic silica, and in which the resultant product is, if appropriate, dried.

It would be desirable to provide a process for the production of 3-hydroxy-3-methylbutyrate which would be independent of inorganic production steps and which could be effected in living organisms thereby being environmentally sound and inexpensive. In this context, Lee et al. (Appl. Environ. Microbiol. 63 (1997), 4191-4195) describes a method for the production of 3-hydroxy-3-methylbutyrate by converting 3-methylbutyric acid to 3-hydroxy-3-methylbutyric acid using the microorganism *Galactomyces reessii*. However, although this process allowed the production of 3-hydroxy-3-methylbutyrate there is still a need to provide alternative efficient and cost effective ways of producing 3-hydroxy-3-methylbutyrate in particular by biological processes.

The present invention meets this demand for an alternative process for the production of 3-hydroxy-3-methylbutyrate and provides a method which is based on biological resources and allows to produce 3-hydroxy-3-methylbutyrate in vitro or in vivo in a microorganism and other species.

DETAILED DESCRIPTION OF THE INVENTION

Method for the Production of 3-hydroxy-3-methylbutyric Acid

In particular, the present invention relates to a method for the production of 3-hydroxy-3-methylbutyric acid (also referred to as beta-hydroxyisovalerate or HIV) from acetone and a compound which provides an activated acetyl group comprising the enzymatic conversion of acetone and a compound which provides an activated acetyl group into 3-hydroxy-3-methylbutyric acid.

Acetone is represented by the following formula: $CH_3$—(C=O)—$CH_3$. In a preferred embodiment the compound which provides an activated acetyl group is characterized by the following formula (I):

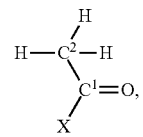

wherein X is selected from the group consisting of S—$CH_2$—$CH_2$—NH—CO—$CH_2$—$CH_2$—NH—CO—CH(OH)—C($CH_3$)$_2$—$CH_2$—O—$PO_2$H—O—$PO_2$H—$C_{10}H_{13}N_5O_7P$ (coenzyme A), S—$CH_2$—$CH_2$—NH—CO—$CH_2$—$CH_2$—NH—CO—CH(OH)—C($CH_3$)$_2$—$CH_2$—O—$PO_2$H-polypeptide (acyl-carrier protein), S—$CH_2$—$CH_2$—NH—CO—$CH_2$—$CH_2$—NH—CO—CH(OH)—C($CH_3$)$_2$—$CH_2$—OH (pantetheine), S—$CH_2$—$CH_2$—NH—CO—$CH_3$ (N-acetyl-cysteamine), S—$CH_3$ (methane thiol), S—$CH_2$—CH($NH_2$)—$CO_2$H (cysteine), S—$CH_2$—$CH_2$—CH($NH_2$)—$CO_2$H (homocysteine), S—$CH_2$—CH(NH—$C_5H_8NO_3$)—CO—NH—$CH_2$—$CO_2$H (glutathione), S—$CH_2$—$CH_2$—$SO_3$H (coenzyme M) and OH (acetic acid).

The conversion makes use of an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group according to formula (I). According to this reaction scheme the oxo group of acetone reacts as an electrophile and the methyl group of the compound which provides an activated acetyl group according to formula (I) reacts as a nucleophile. The general reaction of the conversion of acetone and a compound which provides an activated acetyl group according to formula (I) is shown in FIG. 5.

The reaction can occur in one step, i.e. 3-hydroxy-3-methylbutyrate can be the direct product of a reaction catalyzed by the above described enzyme. Alternatively, the reaction may comprise two steps, in particular in the case where acetyl CoA is used as the compound which provides an activated acetyl group, in the sense that first an adduct of 3-hydroxy-3-methylbutyrate and the compound which provides an activated acetyl group is produced, e.g. 3-hydroxy-3-methylbutyryl-CoA, which is subsequently hydrolyzed, e.g. to 3-hydroxy-3-methylbutyrate and CoA. Thus, in the first alternative the enzyme catalyzes the complete reaction as shown in FIG. 5. In the second alternative, the enzyme catalyzes the formation of a covalent bond between the carbon atom of the oxo (i.e. the C=O) group of acetone and the carbon atom ($C^2$) corresponding to the methyl group of the compound which provides an activated acetyl group but X stays in the molecule. X is then removed subsequently from the molecule by hydrolysis.

The present invention shows for the first time that it is possible to produce 3-hydroxy-3-methylbutyrate by making use of an enzyme which can transfer an activated acetyl group to acetone. In the prior art production of 3-hydroxy-3-methylbutyrate from isovaleric acid through bioconversion using the fungus *Galactomyces reessii* has been reported. However, considering that isovaleric acid is obtained from leucine through decarboxylation and that leucine itself derives in metabolism from the overall condensation of two molecules of pyruvate and one molecule of acetyl CoA, this production process is energetically unfavorable. The process of the present invention avoids this disadvantage.

In general, in the context of the present invention any enzyme could be used which accepts a compound which provides an activated acetyl group as defined above as one substrate as well as a substrate which contains as a component an acetone group. In one preferred embodiment, the enzyme is an enzyme which accepts acetyl CoA as a substrate. Examples for such enzymes are HMG CoA synthase, HMG CoA lyase or other C—C bond cleavage/condensation lyases. However, as will be explained below, also enzymes which normally use in the reaction that they catalyze in nature an acetyl-donor different from acetyl CoA, may use acetyl CoA or analogues thereof, e.g. the PksG protein.

In another preferred embodiment the enzyme is an enzyme which accepts as a substrate a compound which provides an activated acetyl group according to formula (I) in which X is an acyl-carrier-protein, such as the acetyl-S-AcpK protein encoded by the pksX gene cluster for producing bacillaene in *Bacillus subtilis*. An example for such an enzyme is the PksG protein. The PksG protein is one of the proteins encoded by the pksX gene cluster from *Bacillus subtilis*. The PksG protein is capable of catalyzing the transfer of a carboxymethyl group —$CH_2$—$CO_2H$ from acetyl-S-AcpK to a β-ketothioester polyketide intermediate linked to one of the thiolation domains of the PksL protein, in a reaction which is analogous to that catalyzed by HMG CoA synthase. However, it has been shown in the context of the present invention that the PksG protein can also use acetyl CoA instead of the acetyl-S-AcpK protein as a donor of an activated acetyl group.

In one preferred embodiment the compound which provides an activated acetyl group is acetyl CoA. Acetyl CoA (also known as acetyl Coenzyme A) in chemical structure is the thioester between coenzyme A (a thiol) and acetic acid.

In another preferred embodiment the compound which provides an activated acetyl group has the formula (I) in which X is an acyl-carrier-protein, such as the acetyl-S-AcpK protein encoded by the pksX gene cluster for producing bacillaene in *Bacillus subtilis*.

Preferably, the enzyme employed in the process is an enzyme with the activity of a HMG CoA synthase (EC 2.3.3.10) and/or a PksG protein and/or an enzyme with the activity of a C—C bond cleavage/condensation lyase, such as a HMG CoA lyase (EC 4.1.3.4).

In one preferred embodiment, the method according to the present invention comprises the enzymatic conversion of acetone and acetyl CoA into 3-hydroxy-3-methylbutyrate with an enzyme which is capable of catalyzing the formation of a covalent bond between the carbon atom of the oxo (i.e. the C=O) group of acetone and the carbon atom $C^2$ of acetyl CoA according to formula (I).

In a preferred embodiment, the enzyme employed in the process according to the invention is an enzyme which has the activity of a HMG CoA synthase (EC 2.3.3.10) or an enzyme which has the activity of a PksG protein or an enzyme which has the activity of a C—C bond cleavage/condensation lyase, such as a HMG CoA lyase (EC 4.1.3.4).

In particular, it has been shown in the context of the present invention that HMG CoA synthase can accept acetone instead of its normal substrate acetoacetyl-CoA thereby allowing the conversion of acetyl-CoA (or a compound according to formula (I)) and acetone into 3-hydroxy-3-methylbutyrate.

Moreover, it has been shown in the context of the present invention that the PksG protein can use acetyl CoA as a substrate instead of the Ac-S-AcpK protein and can catalyze the reaction which is normally catalyzed by HMG CoA synthase. Thus, it is contemplated that also the PksG protein, which catalyzes a reaction analogous to the reaction of HMG CoA synthase, will be able to catalyze the conversion of acetone and a compound of formula (I) into 3-hydroxy-3-methylbutyrate. Moreover, it is contemplated that C—C bond cleavage/condensation lyases, such as HMG CoA lyase, can catalyze the conversion of acetyl-CoA and acetone into 3-hydroxy-3-methylbutyryl-CoA which in turn can be hydrolysed to 3-hydroxy-3-methylbutyrate and CoA.

HMG CoA Synthase

In the context of the present application the term "HMG CoA synthase" or "a protein/enzyme having the activity of a HMG CoA synthase" refers to any enzyme which is classified in the EC number EC 2.3.3.10 (formerly, HMG-CoA synthase has been classified as EC 4.1.3.5 but has been transferred to EC 2.3.3.10), in particular it refers to any enzyme which is able to catalyze the reaction where acetyl-CoA condenses with acetoacetyl-CoA to form 3-hydroxy-3-methylglutaryl-CoA (HMG-CoA) (see FIG. 2) and the term also refers to any enzyme which is derived from such a HMG CoA synthase and which is capable of catalyzing the conversion of acetone and a compound which provides an activated acetyl group as defined above, preferably acetyl CoA, into 3-hydroxy-3-methylbutyrate.

The enzymatic activity of condensing acetyl-CoA with acetoacetyl-CoA to form 3-hydroxy-3-methylglutaryl-CoA (HMG-CoA) can be measured by methods well known in the art. One possible and preferably used assay is described, e.g., in Clinkenbeard et al. (J. Biol. Chem. 250 (1975), 3108-3116). In this assay HMG-CoA synthase activity is measured by monitoring the decrease in absorbance at 303 nm that accompanies the acetyl-CoA-dependent disappearance of the enolate form of acetoacetyl-CoA. Preferably HMG CoA synthase activity is assayed as described in Example 3.

HMG CoA synthase is part of the mevalonate pathway. Two pathways have been identified for the synthesis of isopentenyl pyrophosphate (IPP), i.e. the mevalonate pathway and the glyceraldehyde 3-phosphate-pyruvate pathway. HMG CoA synthase catalyzes the biological Claisen condensation of acetyl-CoA with acetoacetyl-CoA and is a member of a superfamily of acyl-condensing enzymes that includes beta-ketothiolases, fatty acid synthases (beta-ketoacyl carrier protein synthase) and polyketide synthases.

HMG CoA synthase has been described for various organisms. Also amino acid and nucleic acid sequences encoding HMG CoA synthases from numerous sources are available. Generally, the sequences only share a low degree of overall sequence identity. For example, the enzymes from *Staphylococcus* or *Streptococcus* show only about 20% identity to those of human and avian HMG CoA synthase. In some sources it is reported that the bacterial HMG CoA synthases and their animal counterparts exhibit only about 10% overall sequence identity (Sutherlin et al., J. Bacteriol. 184 (2002), 4065-4070). However, the amino acid residues involved in the acetylation and condensation reactions are conserved among bacterial and eukaryotic HMG CoA synthases (Campobasso et al., J. Biol. Chem. 279 (2004), 44883-44888). The three-dimensional structure of three HMG CoA synthase enzymes has been determined and the amino acids crucial for the enzymatic reaction are in principle well characterized (Campobasso et al., loc. cit.; Chun et al., J. Biol. Chem. 275 (2000), 17946-17953; Nagegowda et al., Biochem. J. 383 (2004), 517-527; Hegardt, Biochem. J. 338 (1999), 569-582). In eukaryotes there exist two forms of the HMG CoA synthase, i.e. a cytosolic and a mitochondrial form. The cytosolic form plays a key role in the production of cholesterol and other isoprenoids and the mitochondrial form is involved in the production of ketone bodies.

In principle any HMG CoA synthase enzyme can be used in the context of the present invention, in particular from prokaryotic or eukaryotic organisms.

Prokaryotic HMG CoA synthases are described, e.g., from *Staphylococcus aureus* (Campobasso et al., loc. cit.; Uniprot accession number Q9FD87), *Staphylococcus epidermidis* (Uniprot accession number Q9FD76), *Staphylococcus haemolyticus* (Uniprot accession number Q9FD82), *Enterococcus faecalis* (Sutherlin et al., loc. cit.; Uniprot accession number Q9FD7), *Enterococcus faecium* (Uniprot accession number Q9FD66), *Streptococcus pneumonia* (Uniprot accession number Q9FD56), *Streptococcus pyogenes* (Uniprot accession number Q9FD61) and *Methanobacterium thermoautotrophicum* (accession number AE000857), *Borrelia burgdorferi* (NCBI accession number BB0683).

Moreover, the following Table A lists some known HMG CoA synthases from prokaryotes:

TABLE A

| Swissprot/TrEmbl Accession number | Organism |
|---|---|
| Q9YAS0 | *Aeropyrum pernix* |
| A7Z4Y2 | *Bacillus amyloliquefaciens* |
| P40830\|2874037340 | *Bacillus subtilis* |
| B8G795 | *Chloroflexus aggregans* |

TABLE A-continued

| Swissprot/TrEmbl Accession number | Organism |
|---|---|
| A5EUV4 | *Dichelobacter nodosus* |
| A5FM54 | *Flavobacterium johnsoniae* |
| Q18GC4 | *Haloquadratum walsbyi* |
| B9LS15 | *Halorubrum lacusprofundi* |
| A9B8F0 | *Herpetosiphon aurantiacus* |
| A2BMY8 | *Hyperthermus butylicus* |
| Q5FLB7 | *Lactobacillus acidophilus* |
| Q03QR0 | *Lactobacillus brevis* |
| Q1GAH5 | *Lactobacillus delbrueckii* |
| B2GBL1 | *Lactobacillus fermentum* |
| B1MZ51 | *Leuconostoc citreum* |
| Q03WZ0 | *Leuconostoc mesenteroides* |
| A4YH99 | *Metallosphaera sedula* |
| A5UNI8 | *Methanobrevibacter smithii* |
| Q58941 | *Methanocaldococcus jannaschii* |
| Q12UR3 | *Methanococcoides burtonii* |
| A6USZ1 | *Methanococcus aeolicus* |
| A4FWW6 | *Methanococcus maripaludis* |
| A6UPL1 | *Methanosarcina mazei* |
| A2STY2 | *Methanocorpusculum labreanum* |
| Q8TVL0 | *Methanopyrus_andleri* |
| Q8PYJ0 | *Methanosarcina mazei* |
| Q2NHU7 | *Methanosphaera stadtmanae* |
| Q2FPH4 | *Methanospirillum hungatei* |
| B2HGT6 | *Mycobacterium marinum* |
| Q3IMZ7 | *Natronomonas pharaonis* |
| Q8EP69 | *Oceanobacillus iheyensis* |
| Q04F95 | *Oenococcus oeni* |
| Q03FU5 | *Pediococcus pentosaceus* |
| Q6L233 | *Picrophilus torridus* |
| A6G7N7 | *Plesiocystis pacifica* |
| A4WJ12 | *Pyrobaculum arsenaticum* |
| A7NHZ7 | *Roseiflexus castenholzii* |
| Q8CN06 | *Staphylococcus epidermidis* |
| Q4L958 | *Staphylococcus haemolyticus* |
| Q4A0D6 | *Staphylococcus saprophyticus* |
| B4U364 | *Streptococcus equi* |
| Q8DUI5 | *Streptococcus mutans* |
| Q4J933 | *Sulfolobus acidocaldarius* |
| Q971K8 | *Sulfolobus tokodaii* |
| Q9HI87 | *Thermoplasma acidophilum* |
| Q31EW2 | *Thiomicrospira crunogena* |
| Q51798 | *Pyrococcus furiosus* |
| A5VJB7 | *Lactobacillus reuteri* |
| Q7CF79 | *Streptococcus pyogenes* |
| Q9UWU0 | *Sulfolobus solfataricus* |

Eukaryotic HMG CoA synthases are described, e.g., from fungi, such as *Schizosaccharomyces pombe* (accession numbers U32187 and P54874), *Saccharomyces cerevisiae* (accession number P54839), plants, such as *Arabidopsis thaliana* (accession numbers X83882 and P54873), *Pinus sylvestris* (accession number X96386) and animals, such as *Caenorhabditis elegans* (accession number P54871), *Mus musculus* (mitochondrial; accession number P54869 and Hegardt, Biochem. J. 338 (1999), 569-582), *Rattus norvegicus* (mitochondrial: accession number P22791 and Hegardt, Biochem. J. 338 (1999); cytosolic: accession number P17425), 569-582), Chinese hamster (*Cricetulus griseus*: accession number P13704), *Sus scrofa* (mitochondrial; accession number U90884 and Hegardt, Biochem. J. 338 (1999), 569-582), *Homo sapiens* (mitochondrial: accession number P54868 and Hegardt, Biochem. J. 338 (1999), 569-582; cytosolic: accession number Q01581), *Blattella germanica* (cytosolic form 1; accession number P54961), *Blattella germanica* (cytosolic form 2; accession number P54870) and *Gallus gallus* (cytosolic; accession number P23228).

Examples of HMG CoA synthases from different organisms are given in SEQ ID NO: 1 to 14. SEQ ID NO: 1 shows the sequence of the cytoplasmic HMG CoA synthase of *Caenorhabditis elegans* (P54871, gene bank F25B4.6), SEQ ID NO: 2 shows the sequence of the cytoplasmic HMG CoA synthase of *Schizosaccharomyces pombe* (fission yeast; P54874), SEQ ID NO: 3 shows the sequence of the cytoplasmic HMG CoA synthase of *Saccharomyces cerevisiae* (baker's yeast; P54839, gene bank CAA65437.1), SEQ ID NO: 4 shows the sequence of the cytoplasmic HMG CoA synthase of *Arabidopsis thaliana* (Mouse-ear cress; P54873), SEQ ID NO: 5 shows the sequence of the cytoplasmic HMG CoA synthase of *Dictyostelium discoideum* (Slime mold; P54872, gene bank L2114), SEQ ID NO: 6 shows the sequence of the cytoplasmic HMG CoA synthase of *Blattella germanica* (German cockroach; P54961, gene bank X73679), SEQ ID NO: 7 shows the sequence of the cytoplasmic HMG CoA synthase of *Gallus gallus* (Chicken; P23228, gene bank CHKHMGCOAS), SEQ ID NO: 8 shows the sequence of the cytoplasmic HMG CoA synthase of *Homo sapiens* (Human; Q01581, gene bank X66435), SEQ ID NO: 9 shows the sequence of the mitochondrial HMG CoA synthase of *Homo sapiens* (Human; P54868, gene bank X83618), SEQ ID NO: 10 shows the sequence of the mitochondrial HMG CoA synthase of *Dictyostelium discoideum* (Slime mold; Q86HL5, gene bank XM_638984), SEQ ID NO: 11 shows the sequence of the HMG CoA synthase of *Staphylococcus epidermidis* (Q9FD76), SEQ ID NO: 12 shows the sequence of the HMG CoA synthase of *Lactobacillus fermentum*(B2 GBL1), SEQ ID NO: 13 shows the sequence of the HMG CoA synthase of *Hyperthermus butylicus* (A2BMY8), SEQ ID NO: 14 shows the sequence of the HMG CoA synthase of *Chloroflexus aggregans* (B8G795), SEQ ID NO: 24 shows the sequence of the HMG CoA synthase of *Lactobacillus delbrueckii* (Q1GAH5) and SEQ ID NO: 25 shows the sequence of the HMG CoA synthase of *Staphylococcus haemolyticus* Q4L958 (I98>V difference compared to wild type protein).

In a preferred embodiment of the present invention the HMG CoA synthase is an enzyme comprising an amino acid sequence selected from the group consisting of SEQ ID NOs: 1 to 14 or a sequence which is at least n % identical to any of SEQ ID NOs: 1 to 14 and having the activity of a HMG CoA synthase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

The HMG CoA synthase employed in the process according to the invention can be a naturally occurring HMG CoA synthase or it can be a HMG CoA synthase which is derived from a naturally occurring HMG CoA synthase, e.g. by the introduction of mutations or other alterations which, e.g., alter or improve the enzymatic activity, the stability, etc.

The term "HMG CoA synthase" or "a protein/enzyme having the activity of a HMG CoA synthase" in the context of the present application also covers enzymes which are derived from a HMG CoA synthase, which are capable of producing 3-hydroxy-3-methylbutyrate by an enzymatic conversion of acetone and a compound which provides an activated acetyl group as defined above, preferably acetyl-CoA, but which only have a low affinity to acetoacetyl-CoA as a substrate or do no longer accept acetoacetyl-CoA as a substrate. Such a modification of the preferred substrate of a HMG CoA synthase allows to improve the conversion of acetone into 3-hydroxy-3-methylbutyrate and to reduce the production of the by-product, e.g. HMG-CoA. Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution".

For example, for genetic engineering in prokaryotic cells, a nucleic acid molecule encoding HMG CoA synthase can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting HMG CoA synthase variants are then tested for their enzymatic activity and in particular for their capacity to prefer acetone as a substrate rather than acetoacetylCoA. An assay for measuring the capacity of a HMG CoA synthase to use acetone as a substrate is described in Example 5. The formation of 3-hydroxy-3-methylbutyrate can be detected by comparison with standard compound, e.g. after separation by thin-layer chromatography, LC/MS and colorimetric assay after its derivatization or by mass spectrometry.

In particular, a reaction is carried out in a reaction mixture containing 40 mM Tris-HCl pH 8, 5 to 50 mM acetyl-CoA, 100 to 500 mM acetone, 1 $MgCl_2$ (except for mitochondria HMG-CoA synthase), 0.5 mM DTT (dithiothreitol) and enzyme varying in the range from 0.2 to 8 mg/ml. Control reactions are carried in the absence of enzyme and one of the substrates.

The progress of synthesis is followed by analyzing aliquots taken after increasing period of incubation at 30 or 37° C. Typically, an aliquot of 50 μl is removed after 48 h of incubation, heated for 1 min at 100° C. to eliminate the proteins, centrifuged and the supernatant is transferred to a clean vial for HIV detection by mass spectrometry. A solution of 3-hydroxy-3-methylbutyrate is prepared in 40 mM Tris-HCl pH 8, 1 mM $MgCl_2$, 0.5 mM DTT, heated as described above and used as reference.

The samples are analyzed on a PE SCIEX® API 2000 triple quadrupole mass spectrometer (mass spectrometer, Perkin-Elmer) in negative ion mode with $H_2O$/acetonitrile=60/40 containing 0.1% triethylamine as mobile phase, flow rate was 40 μl/min. 10 μl of each supernatant are mixed with an equal quantity of mobile phase and directly injected into the mass spectrometer. The presence of [3-hydroxy-3-methylbutyrate-H]$^-$ ion is monitored.

3-hydroxy-3-methylbutyrate synthesis can also be carried out in the presence of radiolabeled [2-$^{14}$C] acetone. The formation of product is analyzed after separation of the reaction mixture by TLC or HPLC.

In a preferred embodiment the HMG CoA synthase employed in the present invention is an enzyme which has a $K_M$ value for acetone of 300 mM or lower, preferably of 250 mM or lower even more preferably of 200 mM or lower and particularly preferred of 150 mM or lower. It is preferred that the $K_M$ value is determined under the conditions described in Example 7. In another preferred embodiment the HMG CoA synthase employed in the present invention has a $k_{cat}$ value for the described reaction of at least $0.1 \times 10^{-4}$ sec$^{-1}$, preferably at least $0.2 \times 10^{-4}$ sec$^{-1}$, even more preferably at least $0.5 \times 10^{-4}$ sec$^{-1}$ and particularly preferred at least $1 \times 10^{-4}$ sec$^{-1}$, at least $2 \times 10^{-4}$ sec$^{-1}$, at least $3 \times 10^{-4}$ sec$^{-1}$ or at least $5 \times 10^{-4}$ sec$^{-1}$. It is preferred that the $k_{cat}$ value is determined under the conditions described in Example 7

It is known in the art that His264 of avian HMG CoA synthase plays a role in the interaction of the enzyme with acetoacetyl-CoA and that the Ala264 variant lacks interaction with the oxygen of the thioester moiety of acetoacetyl-CoA (Misraa et al., Biochem. 35 (1996), 9610-9616). Thus, in order to develop variants of HMG CoA synthase which show a lower acceptance of acetoacetyl-CoA as a substrate but which accept acetone as a substrate, it is conceivable to systematically mutate in a HMG CoA synthase the histidine residue which corresponds to His264 of the avian HMG CoA synthase described in Misraa et al. (loc. cit.) so as to reduce or disable the acceptance of acetoacetyl-CoA as substrate.

In addition, HMG CoA synthase variants can be provided which show an increased activity. Steussy et al. (Biochemistry 45 (2006), 14407-14414), for example, describe a mutant of the *Enterococcus faecalis* HMG CoA synthase in which Ala110 was changed to Gly110 and which shows an 140-fold increase of the overall reaction rate.

Methods for identifying variants with improved enzymatic properties as regards the production of 3-hydroxy-3-methylbutyrate may also be carried out in the presence of a cofactor which allows for a steric and/or electronic complementation in the catalytic site of the enzyme/enzymes due to the fact that the substrate acetone is shorter than the natural substrate acetoacetyl-CoA of, HMG CoA synthase. One example of such a cofactor would be coenzyme A or a structurally closely related molecule such as S-nitroso-CoA.

The modified version of the HMG CoA synthase accepting acetone as a substrate but having a low affinity to acetoacetyl-CoA as a substrate or no longer accepting acetoacetyl-CoA as a substrate may be derived from a naturally occurring HMG CoA synthase or from an already modified, optimized or synthetically synthesized HMG CoA synthase.

PksG Protein

Another example for a protein which can be used in a method according to the invention is a PksG protein. In the context of the present application the term "PksG protein" or "a protein/enzyme having the activity of a PksG protein" refers to any enzyme which is able to catalyze the reaction which is naturally catalyzed by the PksG protein, i.e the transfer of —CH$_2$COO$^-$ from acetyl-S-AcpK (Ac-S-AcpK) to a β-ketothioester polyketide intermediate linked to one of the thiolation domains of the PksL protein. This is a reaction which is analogous to that catalyzed by HMG CoA synthase with the difference that the acetyl-thioester of the phosphopantetheyl moiety is attached to a carrier protein rather than to part of Coenzyme A. Although the PksG protein in the reaction which it naturally catalyzes transfers the acetyl group from acetyl-S-AcpK to an acceptor, it has been shown in the context of the present invention that the PksG protein can also effect the reaction which is normally catalyzed by HMG CoA synthase, i.e. the synthesis of HMG CoA starting from acetoacetyl CoA and acetyl CoA (see Example 3 where it is shown in Table 1 that the enzyme from *Mycobacterium marinum* (B2HGT6) can act on acetoacetyl CoA and acetyl CoA).

The enzymatic activity of the PksG protein can be measured by methods known in the art. One possible and preferably used assay is described, e.g., in Calderone et al. (Proc. Natl. Acad. Sci. USA 103 (2006), 8977-8982). In this assay acetoacetyl (Acac)-S-PksL-T2 is used as a model substrate and is incubated together with Ac-S-AcpK and the PksG protein. The formation of HMG-S-PksL-T2 indicates that the PksG protein is capable of transferring the carboxymethyl group —CH$_2$—CO$_2$H from Ac-S-AcpK to (Acac)-S-PksL-T2. The formation of HMG-S-PksL-T2 can be determined either by electrospray ionization (ESI)-FTMS or in an autoradiography. In a preferred embodiment the corresponding assays are carried out as described on page 8982 of Calderone et al. (Proc. Natl. Acad. Sci. USA 103 (2006), 8977-8982).

The PksG protein is part of the pksX pathway in *Bacillus subtilis* which encodes the enzymes responsible for the biosynthesis of bacillaene (Butcher et al., Proc. Natl. Acad. Sci. USA 104 (2007), 1506-1509). The encoded proteins are AcpK, PksC, PksL, PksF, PksG, PksH and PksI. According to Calderone et al. (Proc. Natl. Acad. Sci. USA 103 (2006), 8977-8982) these enzymes act to incorporate an acetate derived β-methyl branch on an acetoacetyl-S-carrier protein.

In a preferred embodiment of the present invention the PksG protein is an enzyme comprising an amino acid sequence as shown in SEQ ID NO: 15 or 16 or a sequence which is at least n % identical to SEQ ID NO: 15 or 16 and having the activity of a PksG protein with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

SEQ ID NO: 15 shows the amino acid sequence of the PksG protein of *Bacillus subtilis* (P40830) and SEQ ID NO: 16 shows the amino acid sequence of the PksG protein of *Mycobacterium marinum* (B2HGT6).

As regards the determination of the degree of sequence identity the same applies as has been set forth above in connection with HMG CoA synthase.

The PksG protein employed in the process according to the invention can be a naturally occurring PksG protein or it can be a PksG protein which is derived from a naturally occurring PksG protein, e.g. by the introduction of mutations or other alterations which, e.g., alter or improve the enzymatic activity, the stability, etc.

The term "PksG protein" or "a protein/enzyme having the activity of a PksG protein" in the context of the present application also covers enzymes which are derived from a PksG protein, which are capable of producing 3-hydroxy-3-methylbutyrate by an enzymatic conversion of acetone and a compound which provides an activated acetyl group as defined above, preferably acetyl-CoA, but which only have a low affinity to their natural substrate or do no longer accept their natural substrate. Such a modification of the preferred substrate of a PksG protein allows to improve the conversion of acetone into 3-hydroxy-3-methylbutyrate and to reduce the production of unwanted by-product. Methods for modifying and/or improving the desired enzymatic activities of proteins are well-known to the person skilled in the art and have been described above. The resulting PksG protein variants are then tested for their enzymatic activity and in particular for their capacity to prefer acetone as a substrate. An assay for measuring the capacity of a PksG protein to use acetone as a substrate is the one described in Example 5 for HMG-CoA synthase. The formation of 3-hydroxy-3-methylbutyrate can be detected as described above.

Such methods for identifying variants with improved enzymatic properties as regards the production of 3-hydroxy-3-methylbutyrate may also be carried out in the presence of a cofactor which allows for a steric and/or electronic complementation in the catalytic site of the enzyme/enzymes due to the fact that the substrate acetone is shorter than the natural substrate of the PksG protein.

The modified version of the PksG protein accepting acetone as a substrate but having a low affinity to or no longer accepting its natural substrate may be derived from a naturally occurring PksG protein or from an already modified, optimized or synthetically synthesized PksG protein.

C—C Bond Cleavage/Condensation Lyase, HMG CoA Lyase

In the context of the present invention the term "C—C bond cleavage/condensation lyase" or "a protein/enzyme having the activity of a C—C bond cleavage/condensation lyase" refers to an enzyme which is capable of cleaving or forming by condensation a C—C bond and which contains a so-called TIM (triose-phosphate isomerase) barrel domain. This TIM barrel domain is found in a number of pyruvate binding enzymes and acetyl-CoA dependent enzymes (Forouhar et al. J. Biol. Chem. 281 (2006), 7533-7545). The TIM barrel domain has the classification lineage 3.20.20.150 in the CATH protein classification database (www.cathdb.info/cathnode/3.20.20.150).

The term "C—C bond cleavage/condensation lyases" in particular includes enzymes which are classified as isopropylmalate synthase (EC 2.3.3.13), as homocitrate synthase (EC 2.3.3.14) or as 4-hydroxy-2-ketovalerate aldolase (EC 4.1.3.39). Isopropylmalate synthase catalyzes the following reaction: acetyl-CoA+3-methyl-2-oxobutanoate+ $H_2O \rightleftharpoons$ (2S)-2-isopropylmalate+CoA. Examples for such enzymes are the corresponding enzyme from *Brucella abortus* (strain 2308; Q2YRT1) and the corresponding enzyme from *Hahella chejuensis* (strain KCTC 2396; Q2SFA7).

A homocitrate synthase (EC 2.3.3.14) is an enzyme that catalyzes the chemical reaction acetyl-CoA+$H_2O$+2-oxoglutarate $\rightleftharpoons$ (R)-2-hydroxybutane-1,2,4-tricarboxylate+CoA. The 4-hydroxy-2-ketovalerate aldolase catalyzes the chemical reaction 4-hydroxy-2-oxopentanoate $\rightleftharpoons$ acetaldehyde+pyruvate.

In the context of the present invention the term "HMG CoA lyase" or "a protein/enzyme having the activity of a HMG CoA lyase" refers to any enzyme which is classified in the EC number EC 4.1.3.4, in particular it refers to any enzyme which is able to catalyze the cleavage of HMG CoA into acetyl CoA and acetoacetate (see FIG. 3) or the reverse of this reaction, i.e. the production of HMG CoA through the condensation of acetyl CoA and acetoacetate, and the term also refers to any enzyme which is derived from such a HMG CoA lyase and which is capable of catalyzing the conversion of acetone and a compound providing an activated acetyl group as defined above, preferably acetyl CoA, into 3-hydroxy-3-methylbutyryl-CoA. In the context of the present invention the produced 3-hydroxy-3-methylbutyryl-CoA can then be hydrolyzed to produce 3-hydroxy-3-methylbutyrate. This could be achieved by measures known to the person skilled in the art, e.g. by making use of an acyl-CoA hydrolase (EC 3.1.2.20) or an acyl-CoA transferase (EC 2.8.3.8).

The enzymatic activity of HMG CoA lyase can be measured by methods well known in the art. One possible assay is described, e.g., in Mellanby et al. (Methods of Enzymatic Analysis; Bergmeyer Ed. (1963), 454-458). In particular, the enzyme activity is measured by a spectrophotometric assay using the NADH-dependent reduction of acetoacetate by 3-hydroxybutyrate dehydrogenase.

Preferably HMG CoA lyase activity is assayed as described in Example 4. In such an assay the reaction mixture (1 ml) contains 40 mM Tris-HCl pH 8, 1 mM $MgCl_2$, 0.5 mM DTT, 0.4 mM HMG-CoA, 0.2 mM NADH, 5 units of 3-hydroxybutyrate dehydrogenase and is incubated for 5 min before adding 0.005 mg/ml of HMG-CoA lyase and then the progress of the reaction is monitored by the decrease in absorbance at 340 nm.

The reaction catalyzed by HMG CoA lyase is described in some instances to require the presence of a divalent cation, such as $Mg^{2+}$ or $Mn^{2+}$. Thus, it is preferred that an assay for determining the activity of HMG CoA lyase includes such divalent cations and that the method according to the invention for the production of 3-hydroxy-3-methylbutyric acid, if it makes use of HMG CoA lyase, is carried out in the presence of such cations.

HMG CoA lyase is part of the hepatic ketogenesis. It catalyses the terminal reaction in the hepatic ketogenesis which is a key step of this pathway. The reaction is also an important step in leucine catabolism.

HMG CoA lyase has been described for various organisms. Amino acid and nucleic acid sequences encoding HMG CoA lyases are available from numerous sources. Generally, the sequences only share an intermediate degree of overall sequence identity. For example, the enzymes from *Bacillus subtilis* or *Brucella melitensis* show only about 45% identity to those of human HMG CoA lyase (Forouhar et al., J. Biol. Chem. 281 (2006), 7533-7545). The three-dimensional structure of various HMG CoA lyase enzymes has been determined and the amino acids crucial for the enzymatic reaction are in principle well characterized (Forouhar et al., loc. cit.; Fu et al., J. Biol. Chem. 281 (2006), 7526-7532). In eukaryotes the HMG CoA lyase is located in the mitochondrial matrix.

In principle any HMG CoA lyase enzyme can be used in the context of the present invention, in particular from prokaryotic or eukaryotic organisms.

Prokaryotic HMG CoA lyases are described, e.g., from *Brucella abortus* (UniProt accession numbers Q2YPL0 and B2S7S2), *Bacillus subtilis* (UniProt accession number O34873), *Bacillus licheniformis* (Fu et al., loc. cit.), *Pseudomonas syringae* (UniProt accession numbers Q4ZTL2 and Q4ZRW6), *Pseudomonas mevalonii* (UniProt accession number P13703), *Shewanella piezotolerans* (UniProt accession number B8CRY9), *Cellvibrio japonicus* (UniProt accession number B3PCQ7), *Azotobacter vinelandii* (UniProt accession numbers C1DJK8 and C1DL53), *Herminiimonas arsenicoxydans* (UniProt accession number A4G1F2) and *Burkholderia cenocepacia* (UniProt accession number A2VUW7).

Moreover, the following Table B lists some known HMG CoA lyases from prokaryotes:

TABLE B

| Swissprot/TrEmbl Accession number | Organism |
|---|---|
| Q6MHG9 | *Bdellovibrio bacteriovorus* |
| A2TNG9 | *Dokdonia donghaensis* |

TABLE B-continued

| Swissprot/TrEmbl Accession number | Organism |
|---|---|
| Q0C392 | *Hyphomonas neptunium* |
| B2HGF8 | *Mycobacterium marinum* |
| Q0K3L2 | *Ralstonia eutropha* |
| A9IB40 | *Bordetella petrii* |
| Q0B1Z9 | *Burkholderia ambifaria* |
| A5FHS2 | *Flavobacterium johnsoniae* |
| Q5X487 | *Legionella pneumophila* |
| A1VJH1 | *Polaromonas naphthalenivorans* |
| Q5WKL8 | *Bacillus clausii* |
| A9IFQ7 | *Bordetella petrii* |
| A6H0L4 | *Flavobacterium psychrophilum* |
| Q8F7U7 | *Leptospira interrogans* |
| A1VLB1 | *Polaromonas naphthalenivorans* |
| A9IR28 | *Bordetella petrii* |
| B1HZX7 | *Lysinibacillus sphaericus* |
| A1VT25 | *Polaromonas naphthalenivorans* |
| Q9KDS7 | *Bacillus halodurans* |
| A9HXH6 | *Bordetella petrii* |
| Q39QG8 | *Geobacter metallireducens* |
| Q2GBZ7 | *Novosphingobium aromaticivorans* |
| Q0KC96 | *Ralstonia eutropha* |
| Q7CSK6 | *Agrobacterium tumefaciens* |
| Q65IT6 | *Bacillus licheniformis* |
| Q7NX69 | *Chromobacterium violaceum* |
| B9LMV8 | *Halorubrum lacusprofundi* |
| A6F2L0 | *Marinobacter algicola* |
| Q8ERF9 | *Oceanobacillus iheyensis* |
| Q88HG4 | *Pseudomonas putida* |
| Q0KF83 | *Ralstonia eutropha* |
| Q0VL35 | *Alcanivorax borkumensis* |
| B2JST8 | *Burkholderia phymatum* |
| A9AXJ6 | *Herpetosiphon aurantiacus* |
| B1ML74 | *Mycobacterium abscessus* |
| Q88H25 | *Pseudomonas putida* |
| Q11V59 | *Cytophaga hutchinsonii* |
| Q0BWU6 | *Hyphomonas neptunium* |
| A1BBP4 | *Paracoccus denitrificans* |
| Q3IGB2 | *Pseudoalteromonas haloplanktis* |
| Q21QR6 | *Rhodoferax ferrireducens* |
| Q21RT0 | *Rhodoferax ferrireducens* |
| A4CMM6 | *Robiginitalea biformata* |
| A7NGX6 | *Roseiflexus castenholzii* |
| A7NPP8 | *Roseiflexus castenholzii* |
| A7NPR9 | *Roseiflexus castenholzii* |
| Q163P7 | *Roseobacter denitrificans* |
| A4X0W1 | *Salinispora tropica* |
| A9KVP4 | *Shewanella baltica* |
| Q12LZ6 | *Shewanella denitrificans* |
| A8FT92 | *Shewanella sediminis* |
| Q82CR7 | *Streptomyces avermitilis* |
| Q72IH0 | *Thermus thermophilus* |
| A9WGE2 | *Chloroflexus aurantiacus* |
| B7H4C6 | *Acinetobacter baumannii* |

Eukaryotic HMG CoA lyases are described, e.g., from plants, such as radish (*Raphanus sativus*) and *Zea mays* (Accession number B6U7B9, gene bank ACG45252) and animals, such as human (*Homo sapiens*; UniProt accession number P35914), Cynomolgus monkey (UniProt accession number Q8XZ6), Sumatran orangutan (*Pongo abelii*; UniProt accession number Q5R9E1), rat (*Rattus norvegicus*; UniProt accession number P97519; Fu et al., loc. cit.), *Mus musculus* (UniProt accession number P38060), duck (*Anas* spec.), cattle (*Bos taurus*; UniProt accession number Q29448), goat (*Capra hircus*), pigeon (*Columba livia*), chicken (*Gallus gallus*; UniProt accession number P35915), sheep (*Ovis aries*), pig (*Sus scrofa*), *Danio rerio* (Brachydanio rerio; A8WG57, gene bank BC154587) and from the protozoa *Tetrahymena pyriformis*.

Examples of HMG CoA lyases from different organisms are given in SEQ ID NOs: 17 to 23. SEQ ID NO: 17 shows the sequence of the HMG CoA lyase of *Zea mays* (Accession number B6U7B9, gene bank ACG45252), SEQ ID NO: 18 shows the sequence of the HMG CoA lyase of *Danio rerio* (Brachydanio rerio; A8WG57, gene bank BC154587), SEQ ID NO: 19 shows the sequence of the HMG CoA lyase of *Bos taurus* (Uniprot accession number Q29448) and SEQ ID NO: 20 shows the sequence of the HMG CoA lyase of *Homo sapiens* (mitochondrial, Uniprot accession number P35914, gene bank HUMHYMEGLA), SEQ ID NO: 21 shows the sequence of the HMG CoA lyase of *Pseudomonas putida* (Q88H25), SEQ ID NO: 22 shows the sequence of the HMG CoA lyase of *Acinetobacter baumannii* (B7H4C6) and SEQ ID NO: 23 shows the sequence of the HMG CoA lyase of *Thermus thermophilus* (Q72IH0).

In a preferred embodiment of the present invention the HMG CoA lyase is an enzyme comprising an amino acid sequence selected from the group consisting of SEQ ID NOs: 17 to 23 or a sequence which is at least n % identical to any of SEQ ID NOs: 17 to 23 and having the activity of a HMG CoA lyase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

As regards the determination of the degree of sequence identity the same applies as has been set forth above in connection with HMG CoA synthase.

The HMG CoA lyase employed in the process according to the invention can be a naturally occurring HMG CoA lyase or it can be a HMG CoA lyase which is derived from a naturally occurring HMG CoA lyase, e.g. by the introduction of mutations or other alterations which, e.g., alter or improve the enzymatic activity, the stability, etc.

The term "HMG CoA lyase" or "a protein/enzyme having the activity of a HMG CoA lyase" in the context of the present application also covers enzymes which are derived from a HMG CoA lyase, which are capable of producing 3-hydroxy-3-methylbutyryl-CoA by a condensation of acetone and a compound which provides an activated acetyl group as defined above, preferably acetyl-CoA but which only have a low affinity to acetoacetate as a substrate or do no longer accept acetoacetate as a substrate. Such a modification of the preferred substrate of a HMG CoA lyase allows to improve the conversion of acetone into 3-hydroxy-3-methylbutyryl-CoA and to reduce the production of the by-product HMG-CoA. Methods for modifying and/or improving the desired enzymatic activities of proteins are well-known to the person skilled in the art and have been described above.

The capacity of a given enzyme to catalyze the production of 3-hydroxy-3-methylbutyryl-CoA can be determined in an assay as described in Example 6.

The modified version of the HMG CoA lyase accepting acetone as a substrate but having a low affinity to acetoacetate as a substrate or no longer accepting acetoacetate as a substrate may be derived from a naturally occurring HMG CoA lyase or from an already modified, optimized or synthetically synthesized HMG CoA lyase.

Reactions May Conducted in Cellulo or in vitro

In the process according to the invention it is possible to employ only one enzyme as defined above, e.g. only a HMG CoA synthase or only a HMG CoA lyase or only a PksG protein. However, it is of course also possible to employ more than one activity, i.e. different enzymes, in particular any combination of a HMG CoA synthase and a HMG CoA lyase and a PksG protein. E.g., in the case of an in vitro method, more than one enzyme activity can be added to the reaction mixture, either simultaneously or subsequently in any possible order. In an in vivo method employing organisms, in particular microorganisms, it is, e.g., possible to use an organism, in particular microorganism, expressing an enzyme as defined above. However, it is also conceivable to use an organism/microorganism expressing any possible combination of the above mentioned enzymes. Moreover, it is also possible to use a mixture of two or more types of organisms/microorganisms with one type expressing one enzyme and another expressing another enzyme. These different types can then be cocultivated.

The enzyme, e.g. the HMG CoA synthase and/or PksG protein and/or a C—C bond cleavage/condensation lyase, such as a HMG CoA lyase, employed in the process according to the present invention can be a natural version of the protein or a synthetic protein as well as a protein which has been chemically synthesized or produced in a biological system or by recombinant processes. The enzyme, e.g. the HMG CoA synthase and/or PksG protein and/or a C—C bond cleavage/condensation lyase, such as a HMG CoA lyase, may also be chemically modified, for example in order to improve its/their stability, resistance, e.g. to temperature, for facilitating its/their purification or its immobilization on a support. The enzyme/enzymes may be used in isolated form, purified form, in immobilized form, as a crude or partially purified extract obtained from cells synthesizing the enzyme/enzymes, as chemically synthesized enzyme(s), as recombinantly produced enzyme(s), in the form of microorganisms producing them etc.

The process according to the present invention may be carried out in vitro or in vivo. An in vitro reaction is understood to be a reaction in which no cells are employed, i.e. an acellular reaction.

For carrying out the process in vitro the substrates for the reaction and the enzyme/enzymes are incubated under conditions (buffer, temperature, cofactors etc.) allowing the enzyme/enzymes to be active and the enzymatic conversion to occur. The reaction is allowed to proceed for a time sufficient to produce 3-hydroxy-3-methylbutyrate. The production of 3-hydroxy-3-methylbutyrate and/or 3-hydroxy-3-methylbutyryl-CoA can be detected by comparison with standard compound after separation by thin-layer chromatography, LC/MS and colorimetric assay after its derivatization.

The enzyme/enzymes may be in any suitable form allowing the enzymatic reaction to take place. It/they may be purified or partially purified or in the form of crude cellular extracts or partially purified extracts. It is also possible that the enzyme/enzymes is immobilized on a suitable carrier.

Since the substrate acetone is in general shorter than the natural substrate used by the enzyme, e.g. acetoacetyl-CoA/acetoacetate used by HMG CoA synthase and HMG CoA lyase, respectively, it may be advantageous to add to the reaction mixture a cofactor which allows for a steric and/or electronic complementation in the catalytic site of the enzyme/enzymes. One example of such a cofactor, in the case of HMG CoA synthase, would be coenzyme A or a structurally closely related molecule such as S-nitroso-CoA.

For carrying out the process in vivo use is made of a suitable organism/microorganism(s) which is/are capable of providing the substrates, i.e. acetone and a compound which provides an activated acetyl group as defined above, and an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group. In a preferred embodiment said enzyme is a HMG CoA synthase and/or PksG protein and/or a C—C bond cleavage/condensation lyase, such as a HMG CoA lyase.

Recombinant Microorganisms

Thus, in the case of this embodiment the method according to the invention is characterised in that the conversion of acetone and a compound which provides an activated acetyl group is realized in the presence of an organism, preferably a microorganism capable of producing acetone and expressing an enzyme which is capable of the formation of a covalent bond between the carbon atom of the oxo (i.e. the C=O) group of acetone and the carbon atom ($C^2$) corresponding to the methyl group of the compound which provides an activated acetyl group, preferably expressing an enzyme with the activity of a HMG CoA synthase (EC 2.3.3.10) and/or expressing a PksG protein and/or expressing an enzyme with the activity of a C—C bond cleavage/condensation lyase, such as a HMG CoA lyase (EC 4.1.3.4).

The term "which is capable of producing acetone" in the context of the present invention means that the organism/microorganism has the capacity to produce acetone within the cell due to the presence of enzymes providing enzymatic activities allowing the production of acetone from metabolic precursors.

Acetone is produced by certain microorganisms, such as *Clostridium acetobutylicum*, *Clostridium beijerinckii*, *Clostridium cellulolyticum*, *Bacillus polymyxa* and *Pseudomonas putida*. The synthesis of acetone is best characterized in *Clostridium acetobutylicum*. It starts out with a reaction (reaction step 1) in which two molecules of acetyl-CoA are condensed into acetoacetyl-CoA. This reaction is catalyzed by acetyl-CoA acetyltransferase (EC 2.3.1.9). Acetoacetyl-CoA is then converted into acetoacetate by a reaction with acetic acid or butyric acid resulting also in the production of acetyl-CoA or butyryl-CoA (reaction step 2). This reaction is catalyzed e.g. by acetoacetylCoA transferase (EC 2.8.3.8). AcetoacetylCoA transferase is known from various organisms, e.g. from *E. coli* in which it is encoded by the atoAD gene or from *Clostridium acetobutylicum* in which it is encoded by the ctfAB gene. However, also other enzymes can catalyze this reaction, e.g. 3-oxoacid CoA transferase (EC 2.8.3.5) or succinate CoA ligase (EC 6.2.1.5).

Finally, acetoacetate is converted into acetone by a decarboxylation step (reaction step 3) catalyzed by acetoacetate decarboxylase (EC 4.1.1.4).

The above described reaction steps 1 and 2 and the enzymes catalyzing them are not characteristic for the acetone synthesis and can be found in various organism. In contrast, reaction step 3 which is catalyzed by acetoacetate decarboxylase (EC 4.1.1.4) is only found in those organisms which are capable of producing acetone.

In one preferred embodiment the organism employed in the method according to the invention is an organism, preferably a microorganism, which naturally has the capacity to produce acetone. Thus, preferably the microorganism belongs to the genus *Clostridium*, *Bacillus* or *Pseudomonas*, more preferably to the species *Clostridium acetobutylicum*, *Clostridium beijerinckii*, *Clostridium cellulolyticum*, *Bacillus polymyxa* or *Pseudomonas putida*.

In a further preferred embodiment, the organism employed in the method according to the invention is an organism, preferably a microorganism, which naturally has the capacity to produce acetone and which is recombinant in the sense that it has further been genetically modified so as to express an enzyme as defined above. The term "recombinant" in one embodiment means that the organism is genetically modified so as to contain a foreign nucleic acid molecule encoding an enzyme as defined above. In a preferred embodiment the organism has been genetically modified so as to contain a foreign nucleic acid molecule encoding an enzyme as defined above, e.g. a HMG CoA synthase, a C—C bond cleavage/condensation lyase, such as a HMG CoA lyase, or a PksG protein or a foreign nucleic acid sequence encoding any possible combination of such proteins. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme, e.g. a HMG CoA synthase and/or a C—C bond cleavage/condensation lyase, such as HMG CoA lyase, and/or a PksG protein, in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does not naturally occur in the respective organism/microorganism. Even more preferably, the promoter is an inducible promoter. Promoters for driving expression in different types of organisms, in particular in microorganisms, are well known to the person skilled in the art.

In another preferred embodiment the nucleic acid molecule is foreign to the organism/microorganism in that the encoded enzyme(s), e.g. the HMG CoA synthase and/or the encoded C—C bond cleavage/condensation lyase, such as HMG CoA lyase, and/or PksG protein, is/are not endogenous to the organism/microorganism, i.e. are naturally not expressed by the organism/microorganism when it is not genetically modified. In other words, the encoded HMG CoA synthase and/or the encoded C—C bond cleavage/condensation lyase, such as HMG CoA lyase, and/or PksG protein is/are heterologous with respect to the organism/microorganism.

The term "recombinant" in another embodiment means that the organism is genetically modified in the regulatory region controlling the expression of an enzyme as defined above which naturally occurs in the organism so as to lead to an increase in expression of the respective enzyme in comparison to a corresponding non-genetically modified organism. The meaning of the term high "higher expression" is described further below.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

The foreign nucleic acid molecule may be present in the organism/microorganism in extrachromosomal form, e.g. as plasmid, or stably integrated in the chromosome. A stable integration is preferred.

In a further preferred embodiment the organism/microorganism is characterized in that the expression/activity of an enzyme as defined above, e.g. of a HMG CoA synthase and/or a C—C bond cleavage/condensation lyase, such as HMG CoA lyase, and/or a PksG protein, is higher in the organism/microorganism genetically modified with the foreign nucleic acid molecule in comparison to the corresponding non-genetically modified organism/microorganism. A "higher" expression/activity means that the expression/activity of the enzyme, in particular of the HMG CoA synthase and/or a C—C bond cleavage/condensation lyase, such as HMG CoA lyase, and/or a PksG protein, in the genetically modified microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%. In particularly preferred embodiments the expression is at least 10-fold, more preferably at least 100-fold and even more preferred at least 1000-fold higher than in the corresponding non-genetically modified organism/microorganism.

The term "higher" expression/activity also covers the situation in which the corresponding non-genetically modified organism/microorganism does not express a corresponding enzyme, e.g. a HMG CoA synthase and/or a C—C bond cleavage/condensation lyase, such as a HMG CoA lyase, and/or a PksG protein, so that the corresponding expression/activity in the non-genetically modified organism/microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the above-mentioned enzymes, in particular HMG CoA synthase and/or a C—C bond cleavage/condensation lyase, such as a HMG CoA lyase, and/or a PksG protein, respectively, are known in the art and have already been described above.

In another preferred embodiment, the organism employed in the method according to the invention is a genetically modified organism, preferably a microorganism, derived from an organism/microorganism which naturally does not produce acetone but which has been genetically modified so as to produce acetone, i.e. by introducing the gene(s) necessary for allowing the production of acetone in the organism/microorganism. In principle any microorganism can be genetically modified in this way. The enzymes responsible for the synthesis of acetone have been described above. Genes encoding corresponding enzymes are known in the art and can be used to genetically modify a given microorganism so as to produce acetone. As described above, the reaction steps 1 and 2 of the acetone synthesis occur naturally in most organisms. However, reaction step 3 is characteristic and crucial for acetone synthesis. Thus, in a preferred embodiment, a genetically modified organism/microorganism derived from an organism/microorganism which naturally does not produce acetone is modified so as to contain a nucleotide sequence encoding an enzyme catalyzing the conversion of acetoacetate into acetone by decarboxylation, e.g. an acetoacetate decarboxylase (EC 4.1.1.4). Nucleotide sequences from several organisms encoding this enzyme are known in the art, e.g. the adc gene from *Clostridium acetobutylicum* (Uniprot accession numbers P23670 and P23673), *Clostridium beijerinckii* (Clostridium MP; Q9RPK1), *Clostridium pasteurianum* (Uniprot accession number P81336), *Bradyrhizobium* sp. (strain BTAi1/ATCC BAA-1182; Uniprot accession number A5EBU7), *Burkholderia mallei* (ATCC 10399 A9LBS0), *Burkholderia mallei* (Uniprot accession number A3MAE3), *Burkholderia mallei* FMH A5XJB2, *Burkholderia cenocepacia* (Uniprot accession number A0B471), *Burkholderia ambifaria* (Uniprot accession number Q0b5P1), *Burkholderia phytofirmans* (Uniprot accession number B2T319), *Burkholderia* spec. (Uniprot accession number Q38ZU0), *Clostridium botulinum* (Uniprot accession number B2TLN8), *Ralstonia pickettii* (Uniprot accession number B2UIG7), *Streptomyces nogalater* (Uniprot accession number Q9EYI7), *Streptomyces avermitilis* (Uniprot accession number Q82NF4), *Legionella pneumophila* (Uniprot accession number Q5ZXQ9), *Lactobacillus salivarius* (Uniprot accession number Q1WVG5), *Rhodococcus* spec. (Uniprot accession number Q0S7W4), *Lactobacillus plantarum* (Uniprot accession number Q890G0), *Rhizobium leguminosarum* (Uniprot accession number Q1M911), *Lactobacillus casei* (Uniprot accession number Q03B66), *Francisella tularensis* (Uniprot accession number Q0BLC9), *Saccharopolyspora erythreae* (Uniprot accession number A4FKR9), *Korarchaeum cryptofilum* (Uniprot accession number B1L3N6), *Bacillus amyloliquefaciens* (Uniprot accession number A7Z8K8), *Cochliobolus heterostrophus* (Uniprot accession number Q8NJQ3), *Sulfolobus islandicus* (Uniprot accession number C3ML22) and *Francisella tularensis* subsp. *holarctica* (strain OSU18).

More preferably, the organism, preferably microorganism, is genetically modified so as to be transformed with a nucleic acid molecule encoding an enzyme capable of catalyzing the above mentioned reaction step 2 of the acetone synthesis, i.e. the conversion of acetoacetyl CoA into acetoacetate.

Even more preferably, the organism, preferably microorganism, is genetically modified so as to be transformed with a nucleic acid molecule encoding an enzyme capable of catalyzing the above mentioned reaction step 1 of the acetone synthesis, i.e. the condensation of two molecules of acetyl CoA into acetoacetatyl CoA.

In a particularly preferred embodiment the organism/microorganism is genetically modified so as to be transformed with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis.

Methods for preparing the above mentioned genetically modified organism, preferably microorganisms, are well known in the art. Thus, generally, the organism/microorganism is transformed with a DNA construct allowing expression of the respective enzyme in the microorganism. Such a construct normally comprises the coding sequence in question linked to regulatory sequences allowing transcription and translation in the respective host cell, e.g. a promoter and/or enhancer and/or transcription terminator and/or ribosome binding sites etc. The prior art already describes microorganisms which have been genetically modified so as to be able to produce acetone. In particular genes from, e.g., *Clostridium acetobutylicum* have been introduced into *E. coli* thereby allowing the synthesis of acetone in *E. coli*, a bacterium which naturally does not produce acetone (Bermejo et al., Appl. Environ. Microbiol. 64 (1998); 1079-1085; Hanai et al., Appl. Environ. Microbiol. 73 (2007), 7814-7818). In particular Hanai et al. (loc. cit.) shows that it is sufficient to introduce a nucleic acid sequence encoding an acetoacetate decarboxylase (such as that from *Clostridium acetobutylicum*) in order to achieve acetone production in *E. coli* indicating that the endogenous enzymes in *E. coli* catalyzing the above-mentioned reaction steps 1 and 2 (i.e. the expression products of the *E. coli* atoB and atoAD genes) are sufficient to provide substrate for the acetone production.

In a particularly preferred embodiment the organism, preferably a microorganism, employed in the method according to the invention is a recombinant organism/microorganism derived from an organism/microorganism which naturally does not produce acetone but which has been genetically modified, as described above, so as to produce acetone and which expresses an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group as defined above. The term "recombinant" in this context preferably means that the organism is recombinant in the sense that it has further been genetically modified so as to express an enzyme as defined above. The term "recombinant" in one embodiment means that the organism is genetically modified so as to contain a foreign nucleic acid molecule encoding an enzyme as defined above, e.g. a HMG CoA synthase or a C—C bond cleavage/condensation lyase, such as a HMG CoA lyase, or a PksG protein, or a foreign nucleic acid molecule encoding any possible combination of the above defined enzymes.

As regards the definition of the term "foreign nucleic acid molecule" the same applies what has already been set forth above.

The term "recombinant" in another embodiment means that the organism is genetically modified in the regulatory region controlling the expression of an enzyme as defined above which naturally occurs in the organism so as to lead to an increase in expression of the respective enzyme in comparison to a corresponding non-genetically modified organism. The meaning of the term high "higher expression" is described further below.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

Preferably such an organism/microorganism is characterized in that the expression/activity of said enzyme, e.g. the HMG CoA synthase and/or a C—C bond cleavage/condensation lyase, such as a HMG CoA lyase, and/or a PksG protein, is higher in the recombinant organism/microorganism in comparison to the corresponding non-genetically modified organism/microorganism. A "higher" expression/activity means that the expression/activity of the enzyme, e.g. the HMG CoA synthase and/or a C—C bond cleavage/condensation lyase, such as HMG CoA lyase, and/or a PksG protein, in the genetically modified organism/microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%. In particularly preferred embodiments the expression is at least 10-fold, more preferably at least 100-fold and even more preferred at least 1000-fold higher than in the corresponding non-genetically modified organism/microorganism.

The term "higher" expression/activity also covers the situation in which the corresponding non-genetically modified organism/microorganism does not express said enzyme, e.g. a HMG CoA synthase and/or a C—C bond cleavage/condensation lyase, such as a HMG CoA lyase, and/or a PksG protein, so that the corresponding expression/activity in the non-genetically modified organism/microorganism is zero.

As regards the methods for measuring the level of expression or activity, the same applies what has already been said above.

The term "organism" as used in the context of the present invention refers in general to any possible type of organism, in particular eukaryotic organisms, prokaryotic organisms and archaebacteria. The term includes animal, plants, fungi, bacteria and archaebacteria. The term also includes isolated cells or cell aggregates of such organisms, like tissue or calli.

In one preferred embodiment, the organism is a microorganism. The term "microorganism" in the context of the present invention refers to prokaryotic cells, in particular bacteria, as well as to fungi, such as yeasts, and also to algae and archaebacteria. In one preferred embodiment, the microorganism is a bacterium. In principle any bacterium can be used. Preferred bacteria to be employed in the process according to the invention are bacteria of the genus *Bacillus, Clostridium, Pseudomonas* or *Escherichia*. In a particularly preferred embodiment the bacterium belongs to the genus *Escherichia* and even more preferred to the species *Escherichia coli*.

In another preferred embodiment the microorganism is a fungus, more preferably a fungus of the genus *Saccharomyces, Schizosaccharomyces, Aspergillus* or *Trichoderma* and even more preferably of the species *Saccharomyces cerevisiae, Schizosaccharomyces pombe, Aspergillus niger* or of the species *Trichoderma reesei*.

In still another preferred embodiment the microorganism is a photosynthetically active microorganism such as bacteria which are capable of carrying out photosynthesis or microalgae.

In a particularly preferred embodiment the microorganism is an algae, more preferably an algae belonging to the diatomeae.

If microorganism are used in the context of the method of the present invention, it is also conceivable to carry out the method according to the invention in a manner in which two types of microorganisms are employed, i.e. one type which produces acetone and one type which uses the acetone produced by the first type of microorganisms to convert it with the help of an enzyme as defined herein above.

When the process according to the invention is carried out in vivo by using microorganisms providing the respective enzyme activity/activities, the microorganisms are cultivated under suitable culture conditions allowing the occurrence of the enzymatic reaction(s). The specific culture conditions depend on the specific microorganism employed but are well known to the person skilled in the art. The culture conditions are generally chosen in such a manner that they allow the expression of the genes encoding the enzymes for the respective reactions. Various methods are known to the person skilled in the art in order to improve and fine-tune the expression of certain genes at certain stages of the culture such as induction of gene expression by chemical inducers or by a temperature shift.

In another preferred embodiment the organism employed in the method according to the invention is an organism which is capable of photosynthesis, such as a plant or microalgae. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as eucalyptus, poplar or rubber tree (*Hevea brasiliensis*).

The present invention also relates to an organism, preferably a microorganism, which is characterized by the following features:
(a) it is capable of producing acetone; and
(b) it expresses an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group as defined above, preferably an enzyme with the activity of a HMG CoA synthase (EC 2.3.3.10) and/or an enzyme with the activity of a C—C bond cleavage/condensation lyase, such as a HMG CoA lyase (EC 4.1.3.4) and/or a PksG protein.

As regards the source, nature, properties, sequence etc. of the enzyme, in particular the HMG CoA synthase, the C—C bond cleavage/condensation lyase, such as HMG CoA lyase, and/or a PksG protein expressed in the organism according to the invention, the same applies as has been set forth above in connection with the method according to the invention.

In one preferred embodiment, the organism according to the invention is an organism, preferably a microorganism which naturally has the capacity to produce acetone, i.e., feature (a) mentioned above is a feature which the organism, preferably microorganism, shows naturally. Thus, preferably the organism is a microorganism which belongs to the genus *Clostridium, Bacillus* or *Pseudomonas*, more preferably to the species *Clostridium acetobutylicum, Clostridium beijerinckii, Clostridium cellulolyticum, Bacillus polymyxa* or *Pseudomonas putida*.

In another preferred embodiment, the organism, preferably microorganism, according to the invention is a genetically modified organism/microorganism derived from an organism/microorganism which naturally does not produce acetone but which has been genetically modified so as to produce acetone, i.e. by introducing the gene(s) necessary for allowing the production of acetone in the organism/microorganism. In principle any organism/microorganism can be genetically modified in this way. The enzymes responsible for the synthesis of acetone have been described above. Genes encoding corresponding enzymes are known in the art and can be used to genetically modify a given organism, preferably microorganism so as to produce acetone.

In a preferred embodiment, a genetically modified organism/microorganism derived from an organism/microorganism which naturally does not produce acetone is modified so as to contain a nucleotide sequence encoding an enzyme catalyzing the conversion of acetoacetate into acetone by decarboxylation, e.g. an acetoacetate decarboxylase (EC 4.1.1.4). Nucleotide sequences from several organisms encoding this enzyme are known in the art, e.g. the adc gene from *Clostridium acetobutylicum*. More preferably, the organism/microorganism is genetically modified so as to be transformed with a nucleic acid molecule encoding an enzyme capable of catalyzing the above mentioned reaction step 2 of the acetone synthesis, i.e. the conversion of acetoacetyl CoA into acetoacetate.

Even more preferably, the organism/microorganism is genetically modified so as to be transformed with a nucleic acid molecule encoding an enzyme capable of catalyzing the above mentioned reaction step 1 of the acetone synthesis, i.e. the condensation of two molecules of acetyl CoA into acetoacetatyl CoA.

In a particularly preferred embodiment the organism/microorganism is genetically modified so as to be transformed with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis or with a nucleic acid molecule encoding an enzyme capable of catalyzing the above mentioned reaction step 1 of the acetone synthesis and with a nucleic acid molecule encoding an enzyme capable of catalyzing the above mentioned reaction step 2 of the acetone synthesis and with a nucleic acid molecule encoding an enzyme capable of catalyzing the above mentioned reaction step 3 of the acetone synthesis.

Methods for preparing the above mentioned genetically modified organisms/microorganisms are well known in the art. Thus, generally, the organism/microorganism is transformed with a DNA construct allowing expression of the respective enzyme in the organism/microorganism. Such a construct normally comprises the coding sequence in question linked to regulatory sequences allowing transcription and translation in the respective host cell, e.g. a promoter and/ or enhancer and/or transcription terminator and/or ribosome binding sites etc. The prior art already describes organism, in particular microorganisms which have been genetically modified so as to be able to produce acetone. In particular genes from, e.g., *Clostridium acetobutylicum* have been introduced into *E. coli* thereby allowing the synthesis of acetone in *E. coli*, a bacterium which naturally does not produce acetone (Bermejo et al., Appl. Environ. Microbiol. 64 (1998); 1079-1085; Hanai et al., Appl. Environ. Microbiol. 73 (2007), 7814-7818). In particular Hanai et al. (loc. cit.) shows that it is sufficient to introduce a nucleic acid sequence encoding an acetoacetate decarboxylase (such as that from *Clostridium acetobutylicum*) in order to achieve acetone production in *E. coli* indicating that the endogenous enzymes in *E. coli* catalyzing the above-mentioned reaction steps 1 and 2 (i.e. the expression products of the *E. coli* atoB and atoAD genes) are sufficient to provide substrate for the acetone production.

In a further preferred embodiment the organism, preferably a microorganism, according to the invention is genetically modified so as to express an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group. In this context, the term "recombinant" means in a first aspect that the organism contains a foreign nucleic acid molecule encoding an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group, preferably a foreign nucleic acid molecule encoding a HMG CoA synthase or a foreign nucleic acid molecule encoding a C—C bond cleavage/condensation lyase, such as a HMG CoA lyase, or a foreign nucleic acid molecule encoding a PksG protein or a foreign nucleic acid molecule encoding any possible combination of the enzymes having the above-mentioned property. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding said enzyme, e.g. the HMG CoA synthase and/or a C—C bond cleavage/condensation lyase, such as a HMG CoA lyase, and/or a PksG protein, in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular microorganisms, are well known to the person skilled in the art.

In another preferred embodiment the nucleic acid molecule is foreign to the organism/microorganism in that the encoded enzyme(s), e.g. the HMG CoA synthase and/or the encoded C—C bond cleavage/condensation lyase, such as a HMG CoA lyase, and/or the encoded PksG protein, is/are not endogenous to the organism/microorganism, i.e. are naturally not expressed by the organism/microorganism when it is not genetically modified. In other words, the encoded enzyme(s), e.g. the HMG CoA synthase and/or the encoded C—C bond cleavage/condensation lyase, such as HMG CoA lyase, and/ or the encoded PksG protein, is/are heterologous with respect to the organism/microorganism.

The term "recombinant" in another aspect means that the organism is genetically modified in the regulatory region controlling the expression of an enzyme as defined above which naturally occurs in the organism so as to lead to an increase in expression of the respective enzyme in comparison to a corresponding non-genetically modified organism.

The meaning of the term high "higher expression" is described further below.

Such a modification of a regulatory region can be achieved by methods known to the person skilled in the art. One example is to exchange the naturally occurring promoter by a promoter which allows for a higher expression or to modify the naturally occurring promoter so as to show a higher expression. Thus, in this embodiment the organism contains in the regulatory region of the gene encoding an enzyme as defined above a foreign nucleic acid molecule which naturally does not occur in the organism and which leads to a higher expression of the enzyme in comparison to a corresponding non-genetically modified organism.

In a further preferred embodiment the organism/microorganism is characterized in that the expression/activity of said enzyme, e.g. the HMG CoA synthase and/or a C—C bond cleavage/condensation lyase, such as HMG CoA lyase, and/or the PksG protein, is higher in the organism/microorganism genetically modified with the foreign nucleic acid molecule in comparison to the corresponding non-genetically modified organism/microorganism. A "higher" expression/activity means that the expression/activity of the enzyme, e.g. the HMG CoA synthase and/or a C—C bond cleavage/condensation lyase, such as HMG CoA lyase, and/or the PksG protein, in the genetically modified organism/microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%. In particularly preferred embodiments the expression is at least 10-fold, more preferably at least 100-fold and even more preferred at least 1000-fold higher than in the corresponding non-genetically modified organism/microorganism.

The term "higher" expression/activity also covers the situation in which the corresponding non-genetically modified organism/microorganism does not express a corresponding enzyme, e.g. a HMG CoA synthase and/or a C—C bond cleavage/condensation lyase, such as a HMG CoA lyase, and/or a PksG protein, so that the corresponding expression/activity in the non-genetically modified organism/microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the above-mentioned enzyme, in particular of a HMG CoA synthase and/or a HMG CoA lyase and/or a PksG protein, respectively, are known in the art and have already been described above.

The term "organism" as used in the context of the present invention refers in general to any possible type of organism, in particular eukaryotic organisms, prokaryotic organisms and archaebacteria. The term includes animal, plants, fungi, bacteria and archaebacteria. The term also includes isolated cells or cell aggregates of such organisms, like tissue or calli.

In one preferred embodiment, the organism is a microorganism. The term "microorganism" in the context of the present invention refers to prokaryotic cells, in particular bacteria, as well as to fungi, such as yeasts, and also to algae and archaebacteria. In one preferred embodiment, the microorganism is a bacterium. In principle any bacterium can be used. Preferred bacteria to be employed in the process according to the invention are bacteria of the genus *Bacillus, Clostridium, Pseudomonas* or *Escherichia*. In a particularly preferred embodiment the bacterium belongs to the genus *Escherichia* and even more preferred to the species *Escherichia coli*.

In another preferred embodiment the microorganism is a fungus, more preferably a fungus of the genus *Saccharomyces, Schizosaccharomyces, Aspergillus* or *Trichoderma* and even more preferably of the species *Saccharomyces cerevisiae, Schizosaccharomyces pombe, Aspergillus niger* or of the species *Trichoderma reesei*.

In still another preferred embodiment the microorganism is a photosynthetically active microorganism such as bacteria which are capable of carrying out photosynthesis or micro-algae.

In a particularly preferred embodiment the microorganism is an algae, more preferably an algae from the genus belonging to the diatomeae.

In another preferred embodiment the organism according to the invention is an organism which is capable of photosynthesis, such as a plant or micro-algae. In principle, it can be any possible plant, i.e. a monocotyledonous plant or a dicotyledonous plant. It is preferably a plant which can be cultivated on an agriculturally meaningful scale and which allows to produce large amounts of biomass. Examples are grasses like *Lolium*, cereals like rye, barley, oat, millet, maize, other starch storing plants like potato or sugar storing plants like sugar cane or sugar beet. Conceivable is also the use of tobacco or of vegetable plants such as tomato, pepper, cucumber, egg plant etc. In another preferred embodiment the plant is an oil storing plants such as rape seed, olives etc. Also conceivable is the use of trees, in particular fast growing trees such as eucalyptus, poplar or rubber tree (*Hevea brasiliensis*).

The present invention also relates to the use of an organism, preferably a microorganism, which is characterized by the following features:
 (a) it is capable of producing acetone; and
 (b) it expresses an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group as defined herein above, preferably an enzyme with the activity of a HMG CoA synthase (EC 2.3.3.10) and/or an enzyme with the activity of a C—C bond cleavage/condensation lyase, such as a HMG CoA lyase (EC 4.1.3.4), and/or a PksG protein for the production of 3-hydroxy-3-methylbutyric acid.

I.e., the present invention also relates to the use of an organism/microorganism according to the invention for the production of 3-hydroxy-3-methylbutyric acid.

The present invention also relates to a composition comprising an organism according to the present invention.

Moreover, the present invention also relates to a composition comprising (i) acetone; and (ii) a compound which provides an activated acetyl group as defined herein above; and (iii) an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group as defined herein above.

For the preferred embodiments of the enzyme the same applies as has already been set forth above in connection with the method and the organism according to the invention.

Moreover, the present invention also relates to the use of an enzyme which is capable of catalyzing the formation of a covalent bond between the carbon atom of the oxo (i.e. the C=O) group of acetone and the carbon atom ($C^2$) corresponding to the methyl group of the compound which provides an activated acetyl group as defined herein above for the production of 3-hydroxy-3-methylbutyric acid.

For the preferred embodiments of the enzyme the same applies as has already been set forth above in connection with the method and the organism according to the invention.

Finally, the present invention also relates to the use of acetone for the production of 3-hydroxy-3-methylbutyric acid, comprising the enzymatic conversion of acetone and a compound which provides an activated acetyl group as defined herein above. In a preferred embodiment the enzymatic conversion is achieved by an enzyme as described above in connection with the method according to the invention, more preferably with an enzyme having the enzymatic activity of a HMG CoA synthase and/or with an enzyme having the enzymatic activity of a C—C bond cleavage/condensation lyase, such as a HMG CoA lyase, and/or a PksG protein, and most preferably the conversion is achieved by the use of an organism according to the invention.

EXAMPLES

Figure 1:
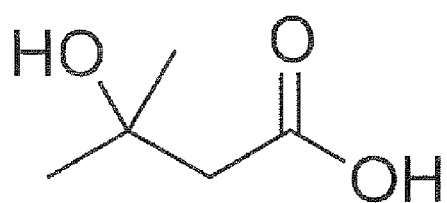
FIG. 1: Chemical structure of 3-hydroxy-3-methylbutyric acid (also referred to as beta-hydroxyisovalerate)
Figure 2:
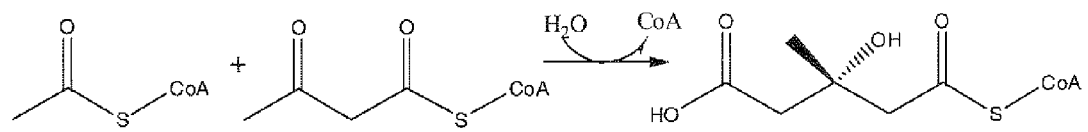
FIG. 2: Reaction scheme of the reaction catalysed by HMG-CoA synthase
Figure 3:
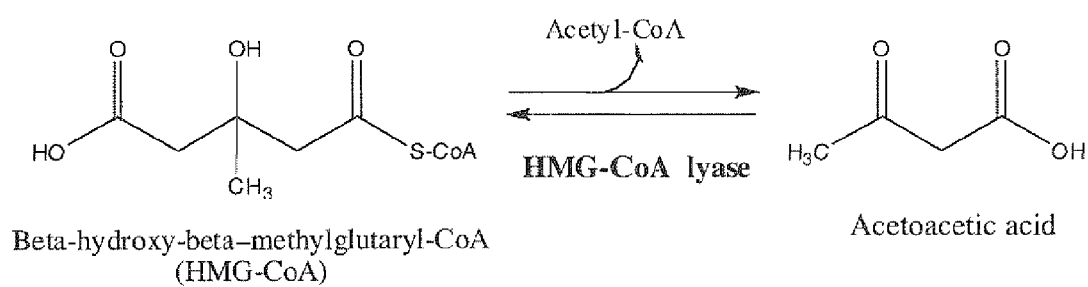
FIG. 3: Reaction scheme of the reaction catalysed by HMG-CoA lyase
Figure 4:
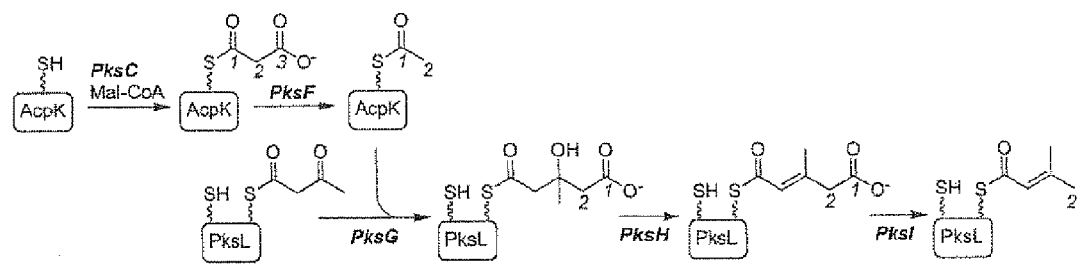
FIG. 4: Reaction schemes of the reactions of the pksX pathway including the reaction catalysed by the PksG protein
Figure 5:
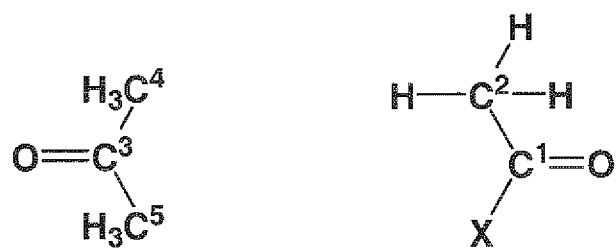
FIG. 5: Reaction scheme of the reaction of the conversion of acetone and a compound containing an activated acetyl group into 3-hydroxy-3-methylbutyric acid X stands for S—$CH_2$—$CH_2$—NH—CO—$CH_2$—$CH_2$—NH—CO—CH(OH)—C($CH_3$)$_2$—$CH_2$—O—$PO_2$H—O—$PO_2$H—$C_{10}H_{13}N_5O_7P$ (coenzyme A), S—$CH_2$—$CH_2$—NH—CO—$CH_2$—$CH_2$—NH—CO—CH(OH)—C($CH_3$)$_2$—$CH_2$—O—$PO_2$H-polypeptide (acyl-carrier protein), S—$CH_2$—$CH_2$—NH—CO—$CH_2$—$CH_2$—NH—CO—CH(OH)—C($CH_3$)$_2$—$CH_2$—OH (pantetheine), S—$CH_2$—$CH_2$—NH—CO—$CH_3$ (N-acetyl-cysteamine), S—$CH_3$ (methane thiol), S—$CH_2$—CH($NH_2$)—$CO_2$H (cysteine), S—$CH_2$—$CH_2$—CH($NH_2$)—$CO_2$H (homocysteine), S—$CH_2$—CH(NH—$C_5H_8NO_3$)—CO—NH—$CH_2$—$CO_2$H (glutathione), S—$CH_2$—$CH_2$—$SO_3$H (coenzyme M) and OH (acetic acid).
Figure 5:
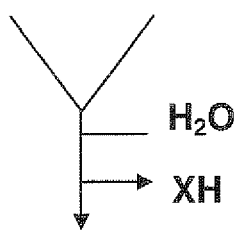
Figure 5:
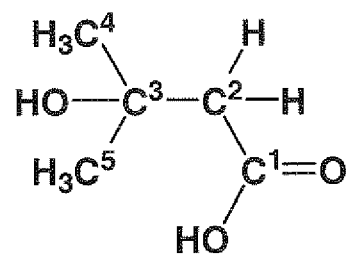

The following examples serve to illustrate the invention.

Example 1

Bioinformatic Method Used to Create HMG-CoA Synthases and HMG-CoA Lyases Database A panel of 12 HMG-CoA synthases and 8 HMG-CoA lyases were selected to create a non-redundant set of proteins aiming to represent the diversity of these enzyme classes as found across eukaryotic organisms. These proteins were identified by performing multiple sequence-based and text-based searches on the Universal Protein Resource Database Uniprot (www.uniprot.org/). They all contain unique features such as conserved protein domains and motifs characteristic to the enzyme class of interest. In order to effectively cover the sequence diversity without having to screen a large set of proteins, the initial pool of enzymes was narrowed down by grouping them into clusters of sequences with more than 85% homology and then selecting one single candidate sequence representative of each cluster. Protein sequence identity ranged from 30% to 80% and from 50% to 80% between any two proteins from the HMG-CoA synthases panel and the lyases panel respectively.

The same approach was applied to select the HMG-CoA synthases and HMG-CoA lyases from prokaryotic organisms. The created set contained 50 proteins homologues to HMG-CoA synthases, including pksG proteins, and 59 proteins homologues to HMG-CoA lyases.

Example 2

Cloning, Expression and Purification of a Collection of HMG-CoA Lyases and HMG-CoA Synthases Gene Cloning:

The nucleic acid sequences coding for HMG-CoA synthase and lyase from eukaryotic organism were optimized for *E. coli* codon preference and the genes were obtained by chemical synthesis (GeneArt®, reagents).

The genes encoding for HMG-CoA synthases and lyases from prokaryotic organisms were cloned from genomic DNA of different origins by routine recombinant techniques. These genes were then inserted in a His-tag containing pET 25b and pET 22b vectors (Novagen, Inc.), respectively, for eukaryotic and prokaryotic organisms.

Overexpression in *E. Coli*:

Plasmids are electroporated into *E. coli* BL21 bacteria (Novagen) that are then spread on an ampicillin containing LB-Agar Petri dish. The cultures are grown at 30° C. on TB medium, containing 0.5 M sorbitol, 5 mM betaine, 100 µg/ml ampicillin under moderate shaking. When OD (600 nm) reached 0.8, IPTG is added to a final concentration of 1 mM, and expression is run for 16 hours at 20° C. under moderated shaking. The bacteria cells are then harvested by centrifugation at 4° C., 10.000 rpm, 20 minutes and frozen at −80° C.

Cell Extract Preparation:

Cell extracts are prepared by resuspending 1.6 g of cell pellet in 5 ml 50 mM $Na_2HPO_4$ buffer, containing 300 mM NaCl, 5 mM $MgCl_2$, 1 mM DTT pH 8. 20 µl lysonase (Novagen) is then added to the preparations, which are incubated for 10 min at room temperature and 20 min on ice. The cell lysis is achieved by triple sonication treatment of 5 minutes in ultrasonic water-bath on ice and homogenization of extract between each pulse. The crude extracts are then clarified by centrifugation at 4° C., 10.000 rpm, 20 minutes.

Protein Purification:

The clear supernatants are loaded onto the PROTINO-1000® Ni-IDA column (columns for the purification of proteins, Macherey-Nagel) which enables the specific immobilisation of proteins carrying 6-histidine tails. The columns are washed and the enzymes are eluted with 4 ml 50 mM $Na_2HPO_4$ buffer, containing 300 mM NaCl, 5 mM $MgCl_2$, 1 mM DTT, 250 mM imidazole pH 8. The enzyme containing fractions are then concentrated and desalted on Amicon® Ultra-4 10 kDa filter unit (membranes for filtration, dialysis; Millipore) and resuspended in 250 µl 40 mM Tris-HCl pH8, containing 0.5 mM DTT. The protein concentration is determined by the Bradford method.

The homogeneity of purified enzymes varied from 20% to 75%.

Example 3

Measure of the HMG-CoA Synthase Activity Using Natural Substrates Acetoacetyl-CoA and Acetyl-CoA The HMG-CoA synthase activity is measured according to Clinkenbeard et al. (J. Biol. Chem. 250 (1975), 3108-3116). The standard assay medium mixture for HMG-CoA synthases contains 40 mM Tris-HCl pH 8, 1 mM $MgCl_2$, 100 µM acetoacetyl-CoA, 200 µM acetyl-CoA, 0.5 mM DTT in a total volume of 1 ml. Mitochondria HMG-CoA synthases are assayed in the absence of $MgCl_2$ to avoid the inhibition observed for this enzyme (Reed et al., J. Biol. Chem. 250 (1975), 3117-3123). Reaction is initiated by addition of 0.02 mg/mL enzyme.

A Control assay was carried out in the absence of enzyme. HMG-CoA synthase activity was measured by monitoring the decrease in absorbance at 303 nm that accompanies the acetyl-CoA-dependent disappearance of the enolate form of acetoacetyl-CoA. To account for non-specific disappearance of acetoacetyl-CoA, results obtained in a control assay lacking enzyme were subtracted from results obtained in test samples. The apparent absorption coefficient for acetoacetyl-CoA under the assay conditions was $5600\ M^{-1}\cdot cm^{-1}$. One enzyme unit represented the disappearance in 1 min of 1 µmol of acetoacetyl-CoA.

TABLE 1

Physiological activity of some purified HMG-CoA synthases or enzymes homologous to HMG CoA synthases

| Uniprot Accession number | Organism | Physiological activity µmol/min · mg protein |
|---|---|---|
| P54961 | Blattella germanica (German cockroach) | 0.02 |
| P23228 | Gallus gallus (Chicken) | 0.02 |
| Q01581 | Homo sapiens (Human) | 0.03 |
| P54873 | Arabidopsis thaliana | 1.19 |
| P54871 | Caenorhabditis elegans | 0.23 |
| P54874 | Schizosaccharomyces pombe (Fission yeast) | 0.61 |
| P54839 | Saccharomyces cerevisiae (Baker's yeast) | 0.28 |
| P54872 | Dictyostelium discoideum (Slime mold) | 0.09 |
| Q86HL5 | Dictyostelium discoideum (Slime mold) | 0.02 |
| Q9M6U3 | Brassica juncea | 0.02 |
| A5FM54 | Flavobacterium johnsoniae | 0.02 |
| Q03WZ0 | Leuconostoc mesenteroides | 0.28 |
| Q2NHU7 | Methanosphaera stadtmanae | 0.02 |
| Q8CN06 | Staphylococcus epidermidis | 0.07 |
| Q03QR0 | Lactobacillus brevis | 0.18 |
| A6UPL1 | Methanosarcina mazei | 0.01 |

TABLE 1-continued

Physiological activity of some purified HMG-CoA synthases or enzymes homologous to HMG CoA synthases

| Uniprot Accession number | Organism | Physiological activity µmol/min · mg protein |
|---|---|---|
| B2HGT6 | Mycobacterium marinum | 0.01 |
| Q4L958 | Staphylococcus haemolyticus | 0.18 |
| Q4A0D6 | Staphylococcus saprophyticus | 0.08 |
| Q1GAH5 | Lactobacillus delbrueckii | 0.32 |

Example 4

Measuring of the HMG-CoA Lyase Activity Using Natural Substrate HMG-CoA

HMG-CoA lyase activity is measured according to Mellanby J et al. (Methods of Enzymatic Analysis; Bergmeyer Ed. (1963), 454-458). The complete reaction mixture (1 ml) containing 40 mM Tris-HCl pH 8, 1 mM $MgCl_2$, 0.5 mM DTT, 0.4 mM HMG-CoA, 0.2 mM NADH, 5 units of 3-hydroxybutyrate dehydrogenase is incubated for 5 min before adding 0.005 mg/ml of HMG-CoA lyase and then the progress of the reaction is monitored by the decrease in absorbance at 340 nm. A control assay was carried out in the absence of enzyme.

To account for non-specific disappearance of NADH, results obtained in a control assay lacking enzyme were subtracted from results obtained in test samples. Specific activities were calculated as Δµmol NADH/min·mg protein.

TABLE 2

Physiological activity of some purified HMG-CoA lyases

| Uniprot Accession number | Organism | Physiological activity µmol/min · mg protein |
|---|---|---|
| A8WG57 | Danio rerio (Zebrafish) (Brachydanio rerio) | 4.05 |
| Q29448 | Bos taurus (Bovine) | 5.79 |
| B6U7B9 | Zea mays | 13.31 |
| A5FHS2 | Flavobacterium johnsoniae | 2.89 |
| A1VJH1 | Polaromonas naphthalenivorans | 34.92 |
| A9IFQ7 | Bordetella petrii | 9.84 |
| A9IR28 | Bordetella petrii | 1.74 |
| A1VT25 | Polaromonas naphthalenivorans | 0.39 |

Example 5

3-hydroxy-3-methylbutyrate Production

The complete reaction for 3-hydroxy-3-methylbutyrate synthesis contained 40 mM Tris-HCl pH 8, 5 to 50 mM acetyl-CoA, 100 to 500 mM acetone, 1 $MgCl_2$ (except for mitochondria HMG-CoA synthase), 0.5 mM DTT and enzyme varying in the range from 0.2 to 8 mg/ml. Control reactions were carried in the absence of enzyme and one of the substrates.

The progress of synthesis was followed by analyzing aliquots taken after increasing period of incubation at 30 or 37° C. Typically, an aliquot of 50 µl was removed after 48 h of incubation, heated for 1 min at 100° C. to eliminate the proteins, centrifuged and the supernatant was transferred to a clean vial for HIV detection by mass spectrometry. A solution of 3-hydroxy-3-methylbutyrate was prepared in 40 mM Tris-HCl pH 8, 1 mM MgCl$_2$, 0.5 mM DTT, heated as described early and used as reference.

The samples were analyzed on a PE SCIEX® API 2000 triple quadrupole mass spectrometer (mass spectrometer, Perkin-Elmer) in negative ion mode with H$_2$0/acetonitrile=60/40 containing 0.1% triethylamine as mobile phase, flow rate was 40 µl/min. 10 µl of each supernatant were mixed with an equal quantity of mobile phase and directly injected into the mass spectrometer. The presence of [3-hydroxy-3-methylbutyrate-H]$^-$ ion was monitored.

A peak corresponding to 3-hydroxy-3-methylbutyrate was observed for the following enzymes:
*Blattella germanica* (German cockroach) P54961 (SEQ ID NO: 6)
*Gallus gallus* (Chicken) P23228 (SEQ ID NO: 7)
*Homo sapiens* (Human) Q01581 (SEQ ID NO: 8)
*Arabidopsis thaliana* P54873 (CAA58763) (SEQ ID NO: 4)
*Caenorhabditis elegans* P54871 (SEQ ID NO: 1)
*Schizosaccharomyces pombe* (Fission yeast) P54874 (SEQ ID NO: 2)
*Saccharomyces cerevisiae* (Baker's yeast) P54839 (SEQ ID NO: 3)
*Dictyostelium discoideum* (Slime mold) Q86HL5 (SEQ ID NO: 10)
*Leuconostoc mesenteroides* Q03WZ0 (SEQ ID NO:)
*Staphylococcus epidermidis* Q8CN06 (SEQ ID NO: 11)
*Lactobacillus delbrueckii* Q1GAH5 (SEQ ID NO: 24)
*Staphylococcus haemolyticus* Q4L958 (I98>V difference compared to wild type protein) (SEQ ID NO: 25)

Figure 6:
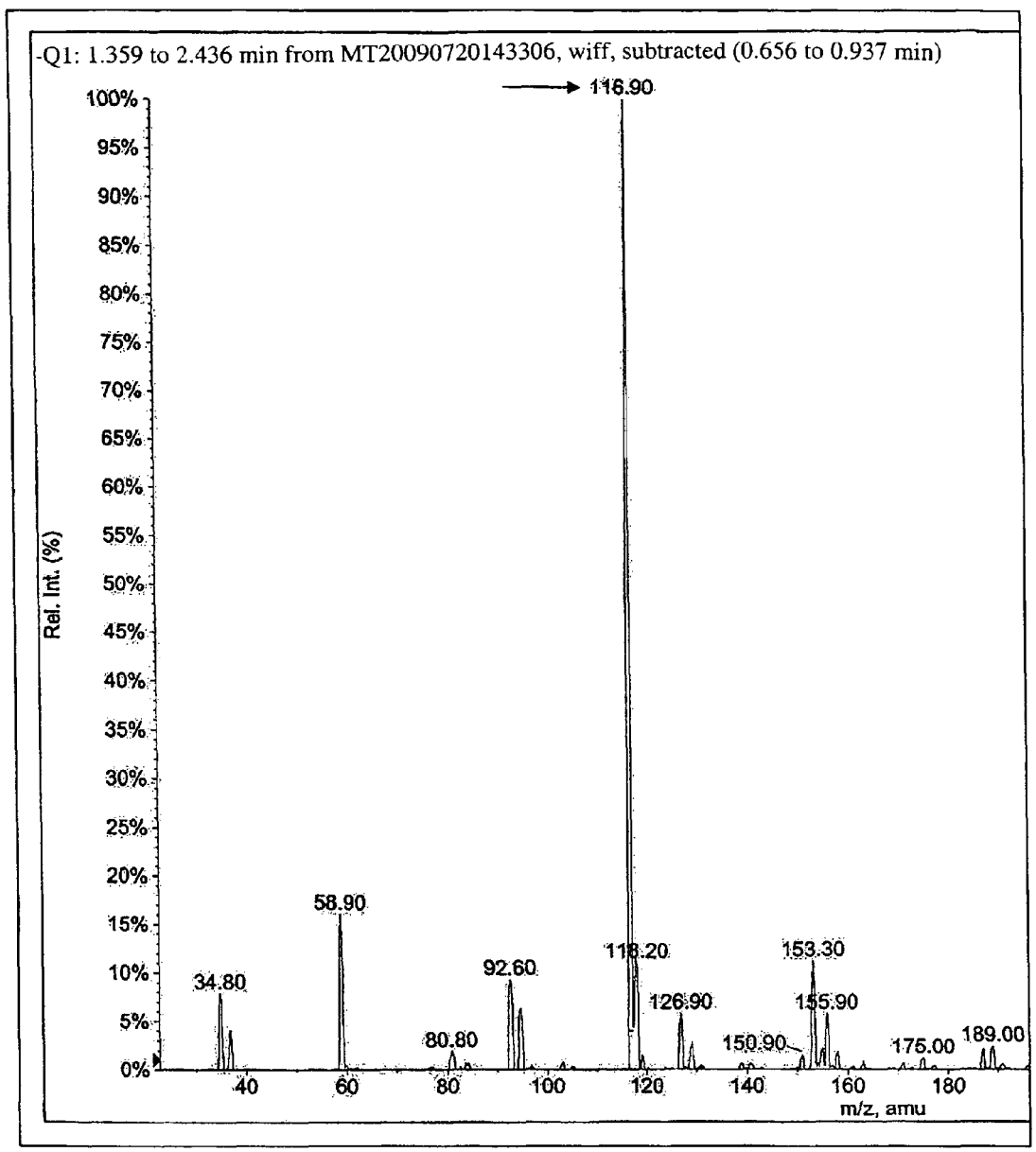
FIG. 6: Mass spectra of commercial available 3-hydroxy-3-methylbutyrate
Figure 7:
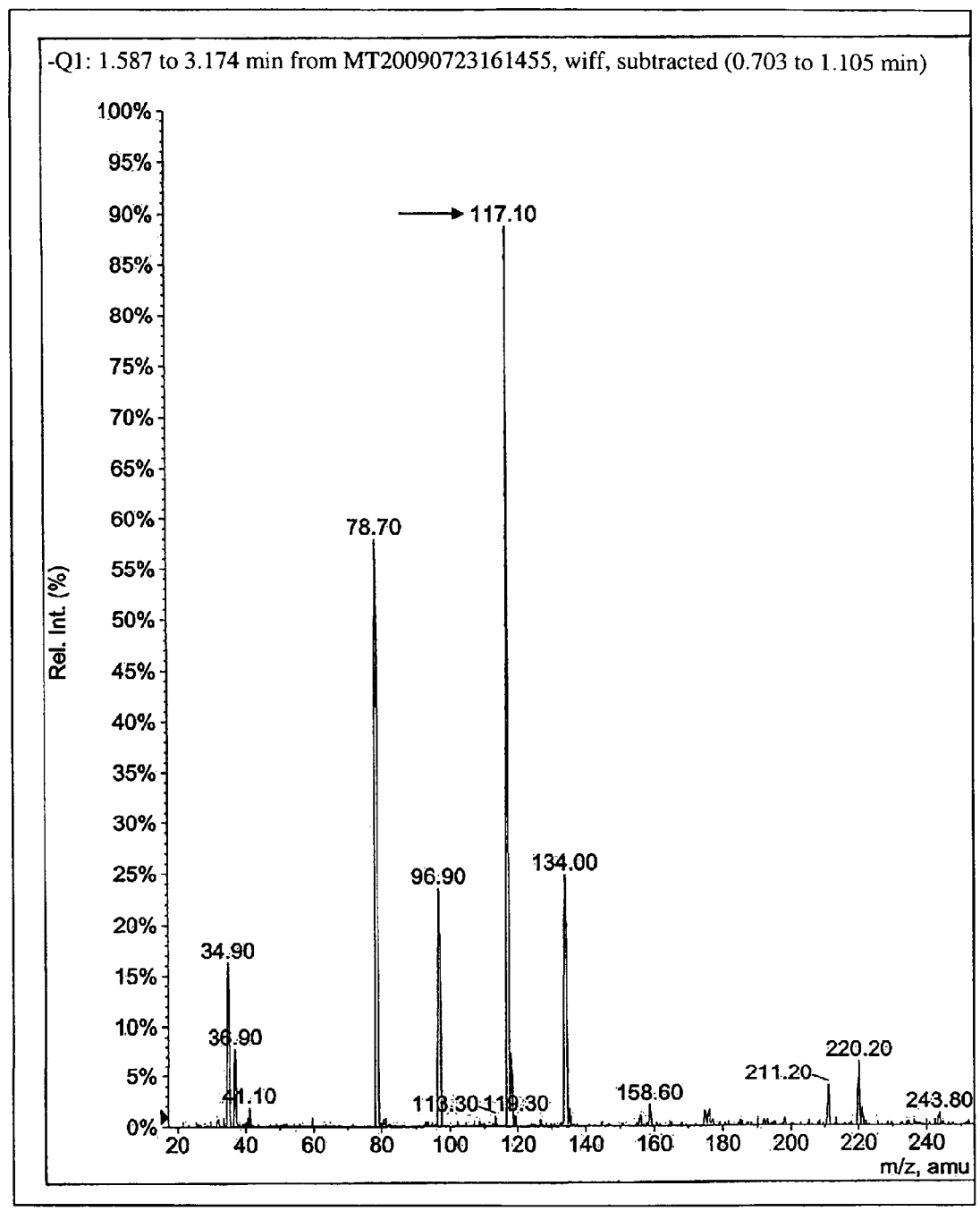
FIG. 7: Mass spectra of formation of 3-hydroxy-3-methylbutyrate from acetyl-CoA and acetone in the presence of Hmg-CoA synthase from *Gallus gallus* (P23228).
Figure 8:
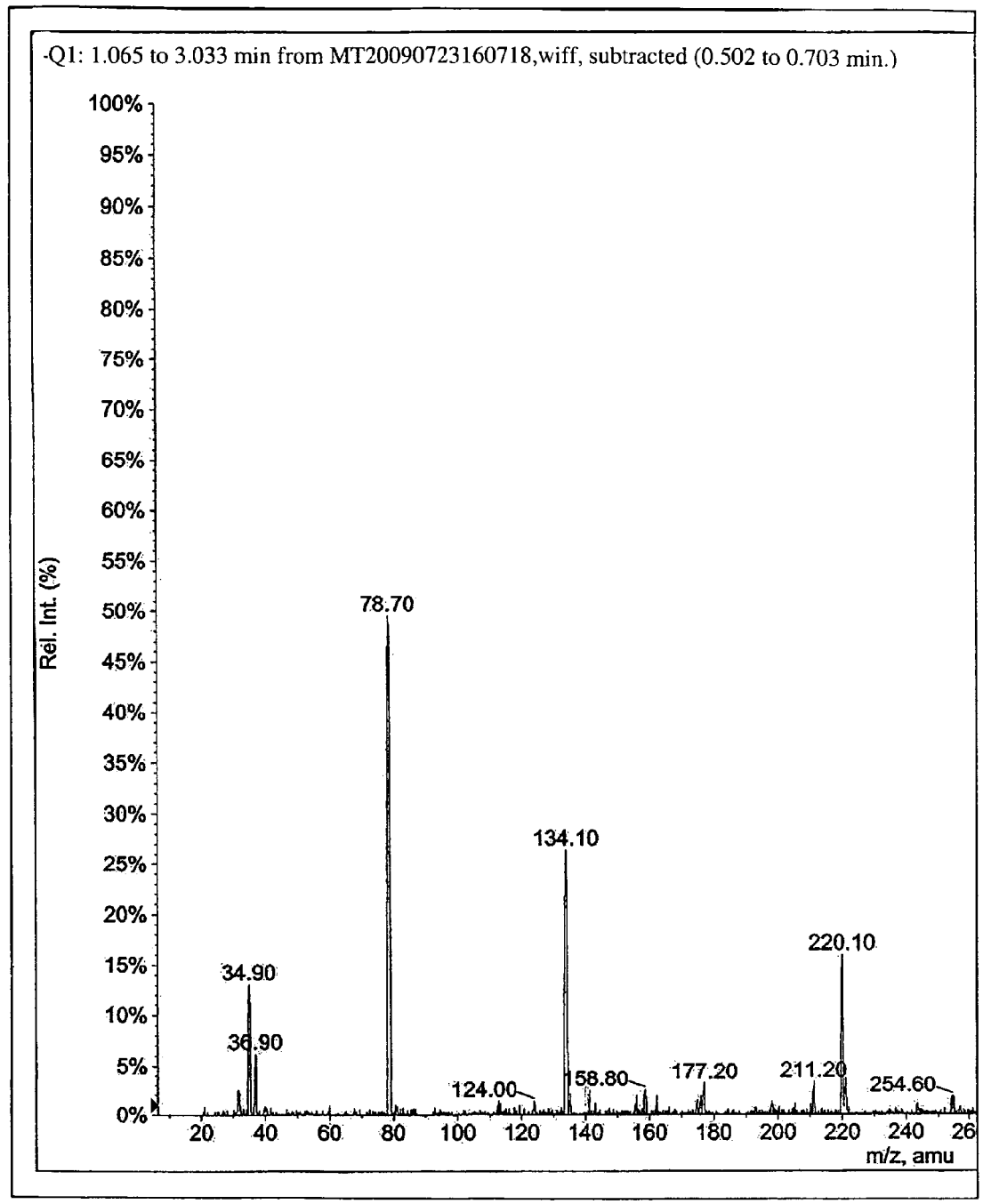
FIG. 8: Mass spectra of the control assay without enzyme.

FIGS. 6 to 8 show representative results for commercially available 3-hydroxy-3-methylbutyrate, for the reaction using the HMG CoA synthase from *Gallus gallus* (P23228) and for the control assay without enzyme.

Example 6

3-hydroxy-3-methylbutyryl-CoA Production Using Lyases 3-hydroxy-3-methylbutyryl-CoA synthesis is carried out in the presence of radiolabeled [2-$^{14}$C] acetone. The complete reaction for 3-hydroxy-3-methylbutyryl-CoA synthesis contains 40 mM Tris-HCl pH 8, 5 to 50 mM acetyl-CoA, 100 to 500 mM acetone, 1 to 10 mM MgCl$_2$, 0.5 mM DTT and enzyme varying in the range from 0.5 to 7 mg/ml. The formation of product is analyzed after separation of reaction mixture by TLC or HPLC.

3-hydroxy-3-methylbutyryl-CoA is also analyzed by TLC method (Stadtman E. R., J. Biol. Chem. 196 (1952), 535-546). An aliquot of reaction is deposited on a cellulose plate and chromatographied in the following solvent system: ethanol/0.1 M sodium acetate pH 4.5 (1/1). Co-A and acetyl-CoA are used as internal standards. $R_f$ reported for 3-hydroxy-3-methylbutyryl-CoA is 0.88.

Example 7

Kinetic Parameters for the Enzymatic Reaction Between Acetyl-CoA and Acetone in the Case of HMG Synthases The kinetic parameters were measured using a variable concentration of acetone and a constant concentration of acetyl-CoA (10 mM) in following conditions:
40 mM Tris-HCl pH 8
2 mM MgCl$_2$
0-1 M acetone The final pH was adjusted to 8.

The reaction was initiated by the addition of 3 mg of purified enzyme to the 1 ml reaction mixture. The mixture was then incubated without shaking at 37° C. for 40 h.

Analysis of 3-hydroxy-3-methylbutyrate Production

Thermochemical conditions leading to the decomposition of 3-hydroxy-3-methylbutyrate into isobutene were applied (Pressman et al., JACS, 1940, 2069-2080): the pH of the reaction mixtures was first adjusted to pH 4 using 6N HCl and the samples were then transferred into gas chromatography vials (Interchim). The vials were sealed and incubated at 110° C. for 4 hours, thus leading to the decomposition of 3-hydroxy-3-methylbutyrate into isobutene.

The calibration curve was prepared in the same conditions using commercial 3-hydroxy-3-methylbutyrate.

One milliliter of headspace gas was collected and injected into a HP5890 gas chromatograph (HP) equipped with a FID detector and a CP SilicaPlot® column (chromatography column; Varian). Commercial isobutene was used as reference. From the isobutene signal the amount of 3-hydroxy-3-methylbutyrate initially present in the sample was calculated.

The kinetics parameters for several of the studied HMG-CoA synthases are presented in the following Table.

| Organism | $K_M$ for acetone, mM | $k_{cat} \times 10^{-4}$, sec$^{-1}$ | $k_{cat}/K_M \times 10^{-6}$, mM$^{-1} \times$ sec$^{-1}$ |
|---|---|---|---|
| *Gallus gallus* | 250 | 5 | 2 |
| *Staphylococcus epidermidis* | 200 | 0.6 | 0.3 |
| *Schizosaccharomyces pombe* | 200 | 0.2 | 0.1 |

Figure 9:
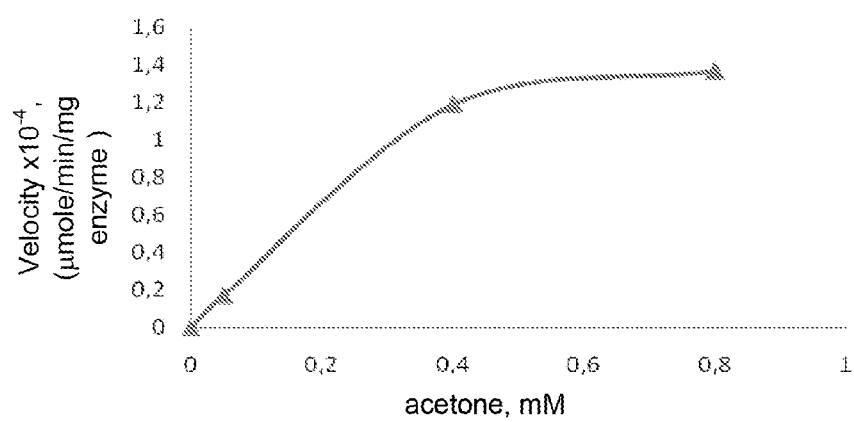
FIG. 9: Michaelis-Menten plot for the reaction with the HMG CoA synthase of *S. epidermidis* described in Example 7

For the enzyme from *S. epidermidis* FIG. 9 shows a corresponding Michaelis-Menten plot.

The invention claimed is:

1. A method for the production of 3-hydroxy-3-methylbutyric acid consisting essentially of:

(a) providing a recombinant microorganism which has been transformed with a polynucleotide encoding 3-hydroxy-3-methylglutaryl-CoA (HMG CoA) synthase and a polynucleotide encoding acetoacetate decarboxylase, wherein at least one of the polynucleotides is heterologous to the recombinant microorganism; and (b) incubating, in the recombinant microorganism (i) acetone and (ii) a compound of formula (I) which provides an activated acetyl group:

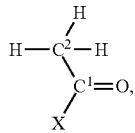

wherein X is S—CH$_2$—CH$_2$—NH—CO—CH$_2$—CH$_2$—NH—CO—CH(OH)—C(CH$_3$)$_2$—CH$_2$—O—PO$_2$H—PO$_2$H—C$_{10}$H$_{13}$N$_5$O$_7$P (coenzyme A),
with (c) the HMG CoA synthase,
under conditions in which the recombinant microorganism produces acetone and expresses the HMG CoA synthase,
thereby producing 3-hydroxy-3-methylbutyric acid.

2. The method of claim 1, wherein the microorganism naturally has the capacity to produce acetone.

3. The method of claim 2, wherein the microorganism is of the genus *Clostridium, Bacillus* or *Pseudomonas*.

4. The method of claim 3, wherein the microorganism is selected from the species *Clostridium acetobutylicum, Clostridium beijerinckii, Clostridium cellulolyticum, Bacillus polymyxa*, and *Pseudomonas putida*.

5. The method of claim 1, wherein the microorganism is of a species which naturally does not produce acetone.

6. The method of claim 5, wherein the microorganism is capable of photosynthesis.

7. The method of claim 1, wherein the microorganism is *Escherichia coli*.

8. The method of claim 1, wherein the microorganism is selected from *Saccharomyces, Schizosaccharomyces, Aspergillus* and *Trichoderma*.

* * * * *